United States Patent
Murphy et al.

(10) Patent No.: US 11,396,544 B2
(45) Date of Patent: Jul. 26, 2022

(54) BISPECIFIC ANTI-CD28 × ANTI-CD22 ANTIBODIES AND USES THEREOF

(71) Applicant: Regeneron Pharmaceuticals, Inc., Tarrytown, NY (US)

(72) Inventors: Andrew J. Murphy, Croton-on-Hudson, NY (US); Dimitris Skokos, New York, NY (US); Janelle Waite, Bronx, NY (US); Erica Ullman, Yorktown Heights, NY (US); Aynur Hermann, New York, NY (US); Eric Smith, New York, NY (US); Kara Olson, White Plains, NY (US); Joyce Wei, New York, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 180 days.

(21) Appl. No.: 16/719,015

(22) Filed: Dec. 18, 2019

(65) Prior Publication Data

US 2020/0239576 A1     Jul. 30, 2020

Related U.S. Application Data

(60) Provisional application No. 62/781,689, filed on Dec. 19, 2018.

(51) Int. Cl.
| | |
|---|---|
| *C07K 16/28* | (2006.01) |
| *A61P 35/00* | (2006.01) |
| *C12N 15/63* | (2006.01) |
| *A61K 39/00* | (2006.01) |

(52) U.S. Cl.
CPC .......... *C07K 16/2818* (2013.01); *A61P 35/00* (2018.01); *C12N 15/63* (2013.01); *A61K 2039/505* (2013.01); *C07K 2317/31* (2013.01); *C07K 2317/565* (2013.01); *C07K 2317/92* (2013.01)

(58) Field of Classification Search
CPC combination set(s) only.
See application file for complete search history.

(56) References Cited

FOREIGN PATENT DOCUMENTS

| EP | 3228325 A1 | 10/2017 |
|---|---|---|
| WO | WO-2018093821 A1 | 5/2018 |
| WO | WO-2020028444 A1 | 2/2020 |
| WO | WO-2020132066 A1 | 6/2020 |

OTHER PUBLICATIONS

Cytolysis of Leukemic B-Cells by T-cells Activated via Two Bispecific Antibodies, Cancer Research, vol. 53, Issue 18, Sep. 15, 1993. Bohlen et al (Year: 1993).*
Bohlen et al (1993) (Cytolysis of Leukemic B-cells by T-cells Activated via Two Bispecific Antibodies, Cancer Research, vol. 53, Issue 18, Sep. 15, 1993). (Year: 1993).*
Bohlen et al., "Cytolysis of leukemic B-cells by T-cells activated via two bispecific antibodies", Cancer Res. Sep. 15, 1993;53(18):4310-4.
J M PéRez De La Lastra et al., "Epitope mapping of 10 monoclonal antibodies against the pig analogue of human membrane cofactor protein (MCP)", Immunology. Apr. 1999; 96(4): 663-670.
International Preliminary Report on Patentability from PCT/US2019/067173 dated Jul. 1, 2021.
Suntharalingam et al., "Cytokine Storm in a Phase 1 Trial of the Anti-CD28 Monoclonal Antibody TGN1412", N Engl J Med 2006;355:1018-28.
Grant et al., "A Phase 2 Trial of Extended Induction Epratuzumab and Rituximab for Previously Untreated Follicular Lymphoma: CALGB 50701", Cancer 2013;119:3797-804.

\* cited by examiner

*Primary Examiner* — Laura B Goddard
*Assistant Examiner* — Sarah A Alsomairy
(74) *Attorney, Agent, or Firm* — McCarter & English, LLP; Marcie B. Clarke; Deborah L. Nagle

(57) ABSTRACT

The present invention provides bispecific antigen-binding molecules comprising a first antigen-binding domain that specifically binds human CD28, and a second antigen-binding molecule that specifically binds human CD-22. In certain embodiments, the bispecific antigen-binding molecules of the present invention are capable of inhibiting the growth of tumors expressing CD-22, such as B-cell lymphomas. The antibodies and bispecific antigen-binding molecules of the invention are useful for the treatment of diseases and disorders in which an up-regulated or induced targeted immune response is desired and/or therapeutically beneficial.

10 Claims, 15 Drawing Sheets

Specification includes a Sequence Listing.

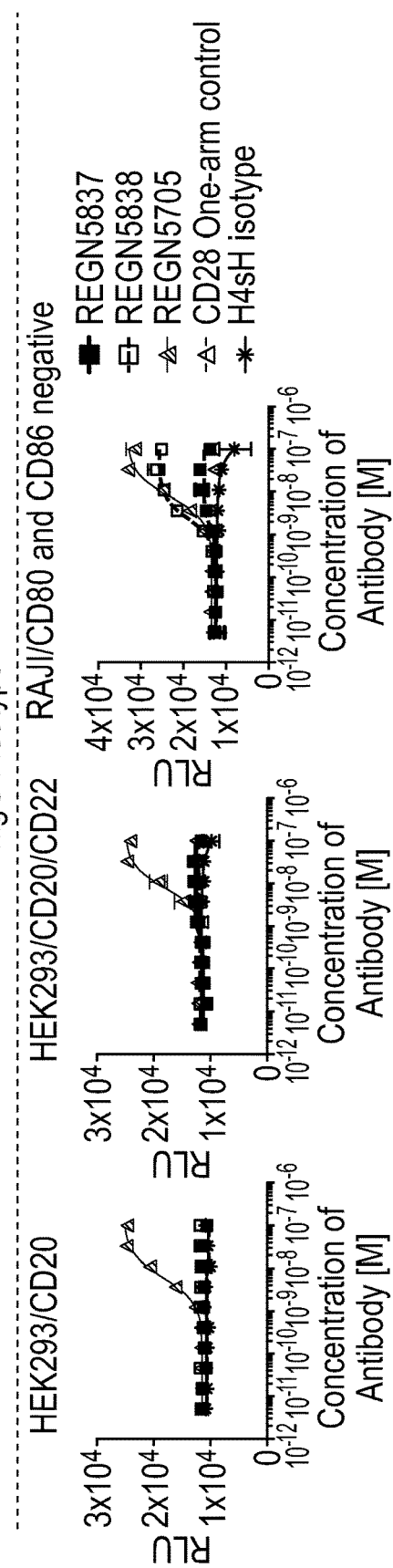
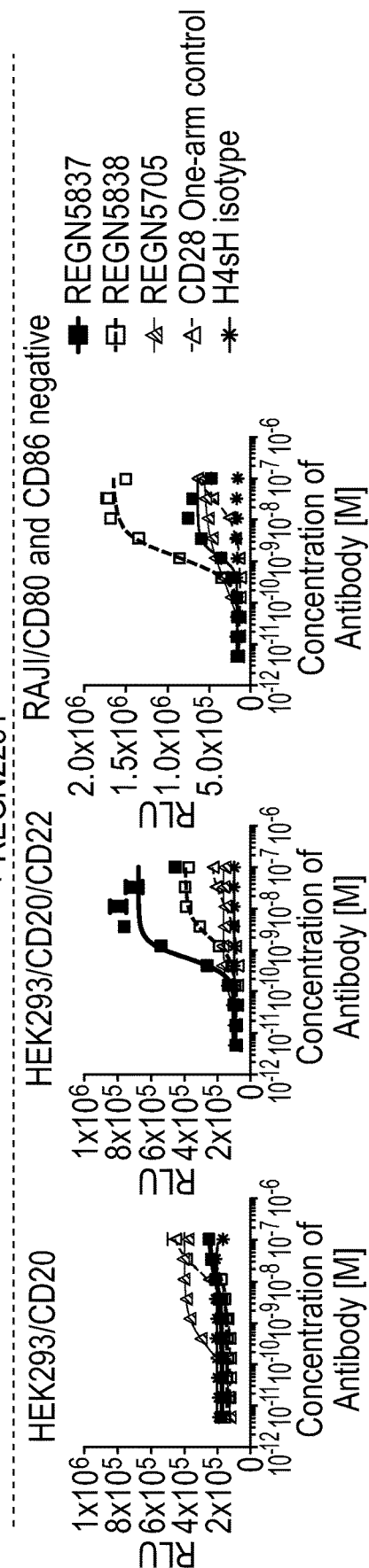
FIG. 2A
FIG. 2B

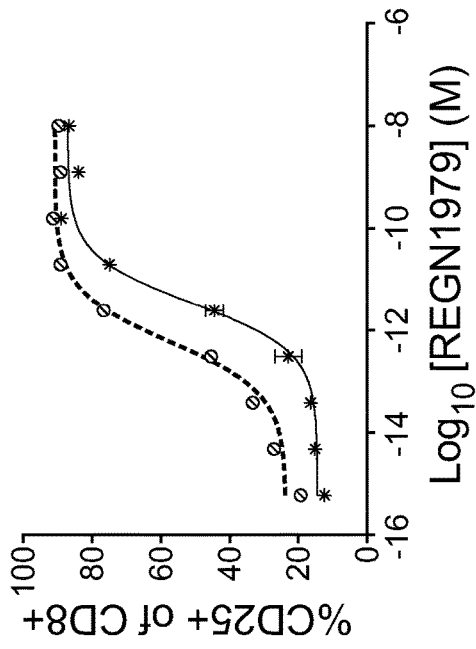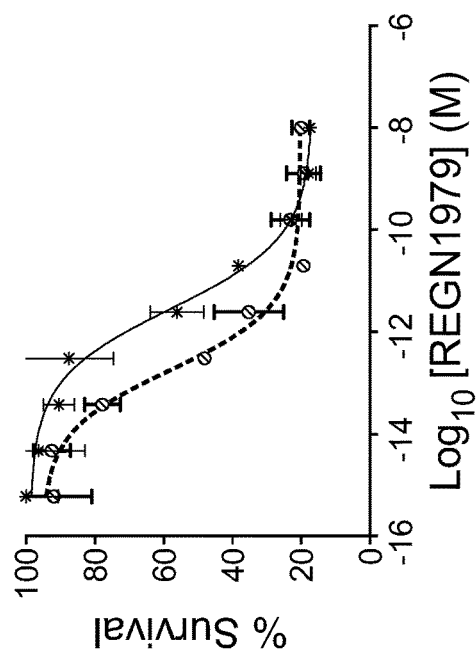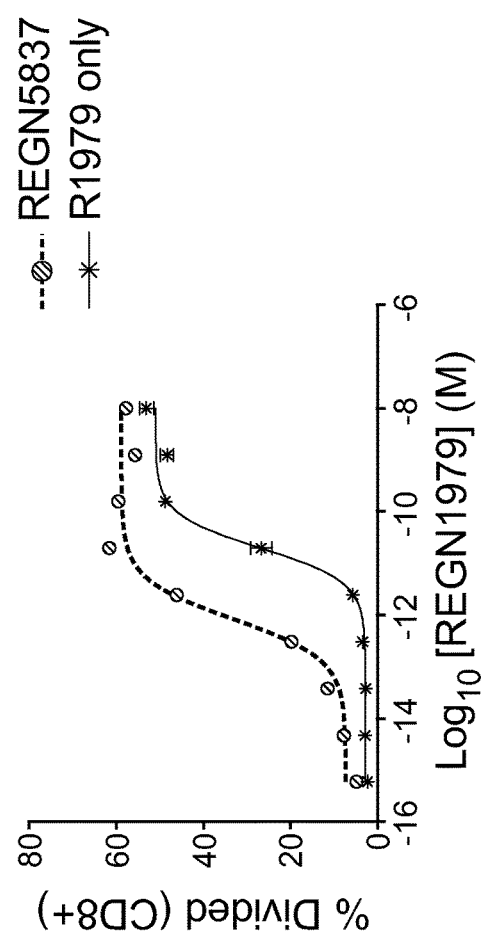
FIG. 8A
FIG. 8B
FIG. 8C
Cytotoxicity and T cell activation – WSU-DLCL2 Targets (representative of 2 experiments)

Cytokine release from WSU-DLCL2 cytotoxicity assay (representative of 2 experiments)

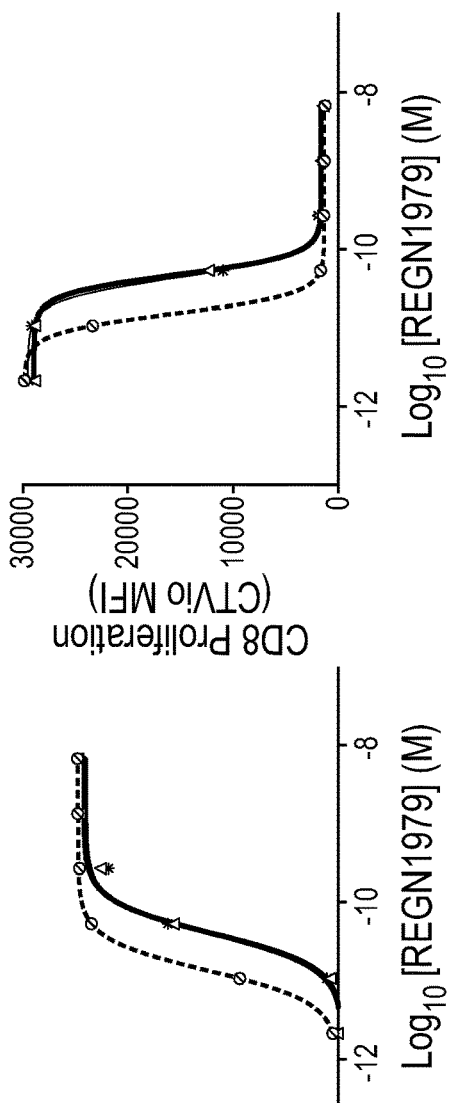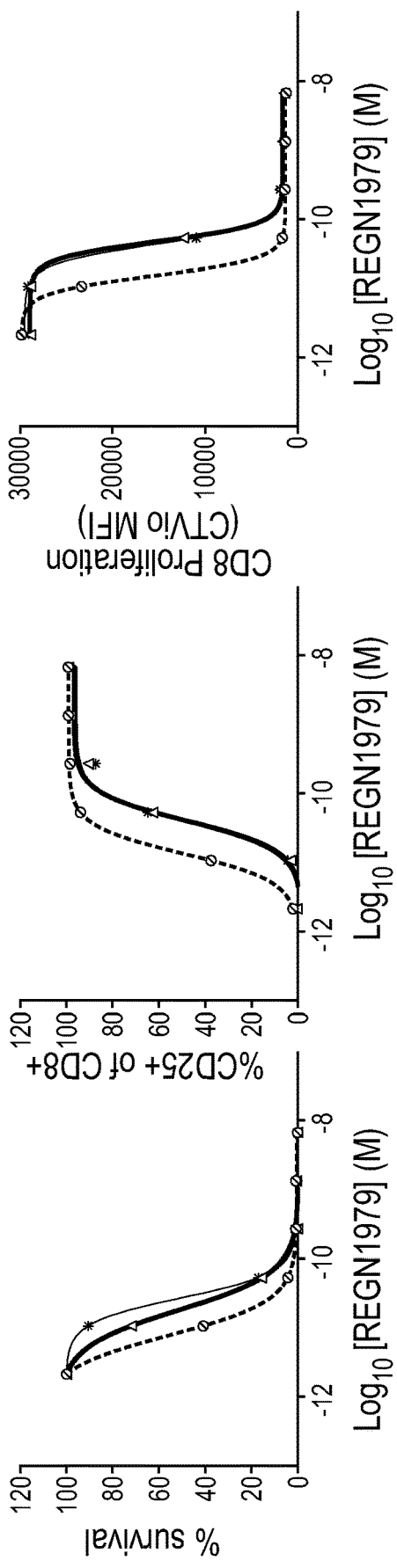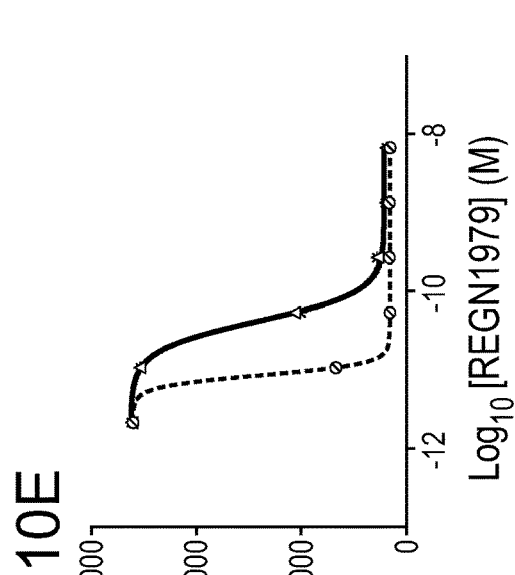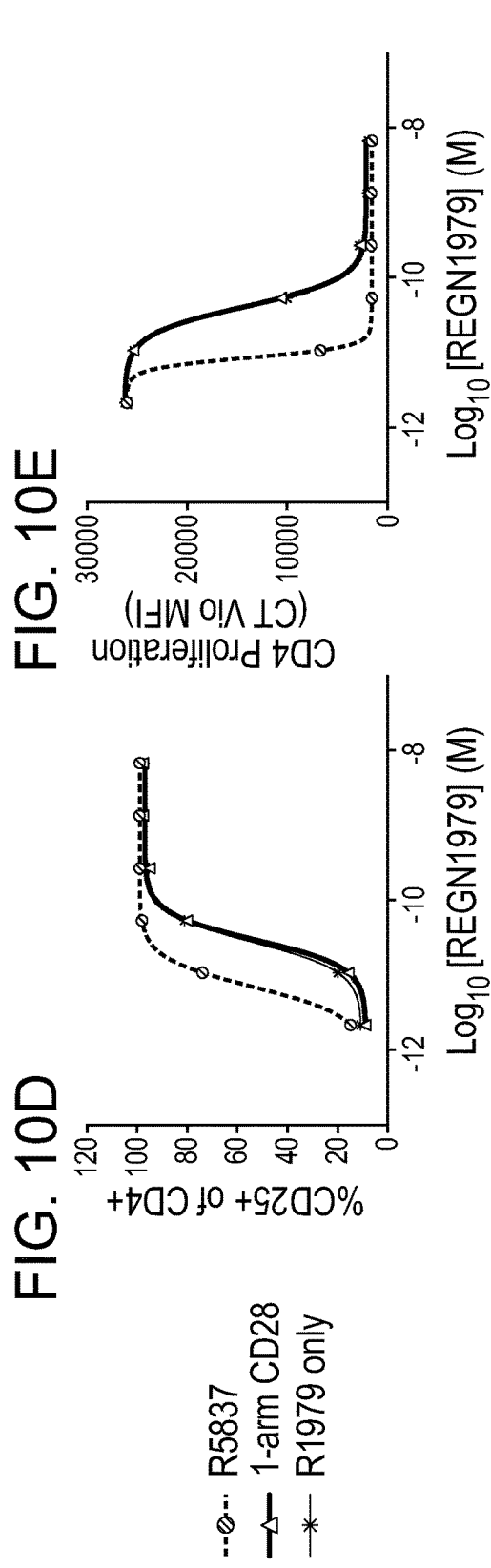
FIG. 10A  FIG. 10B  FIG. 10C  FIG. 10D  FIG. 10E
Cytotoxicity, T cell activation and proliferation

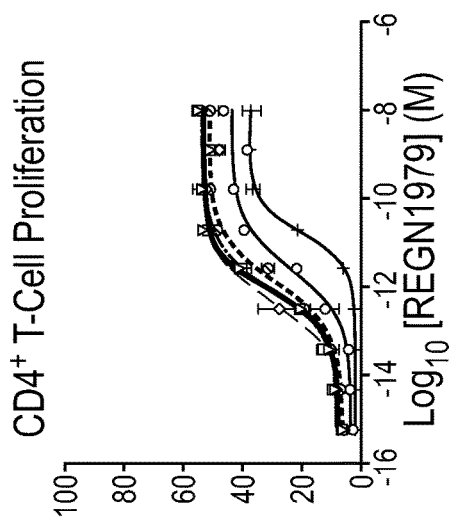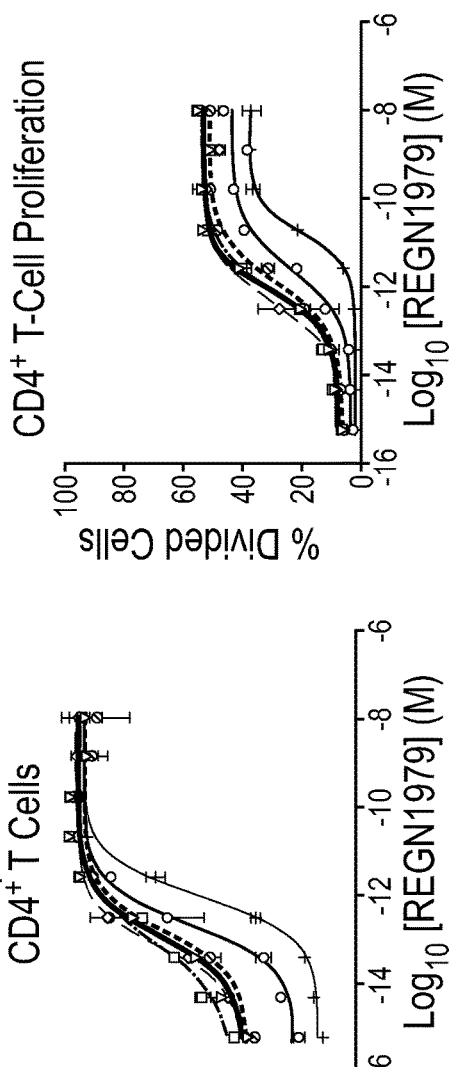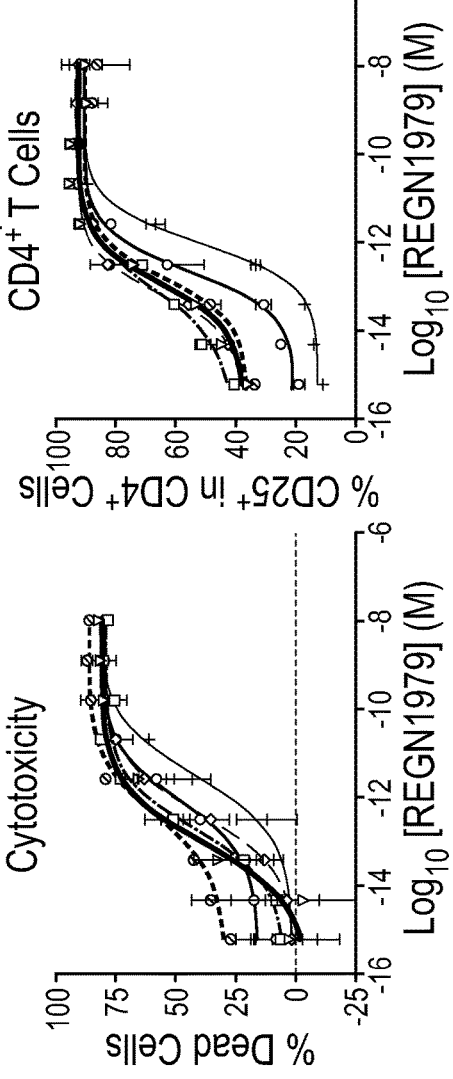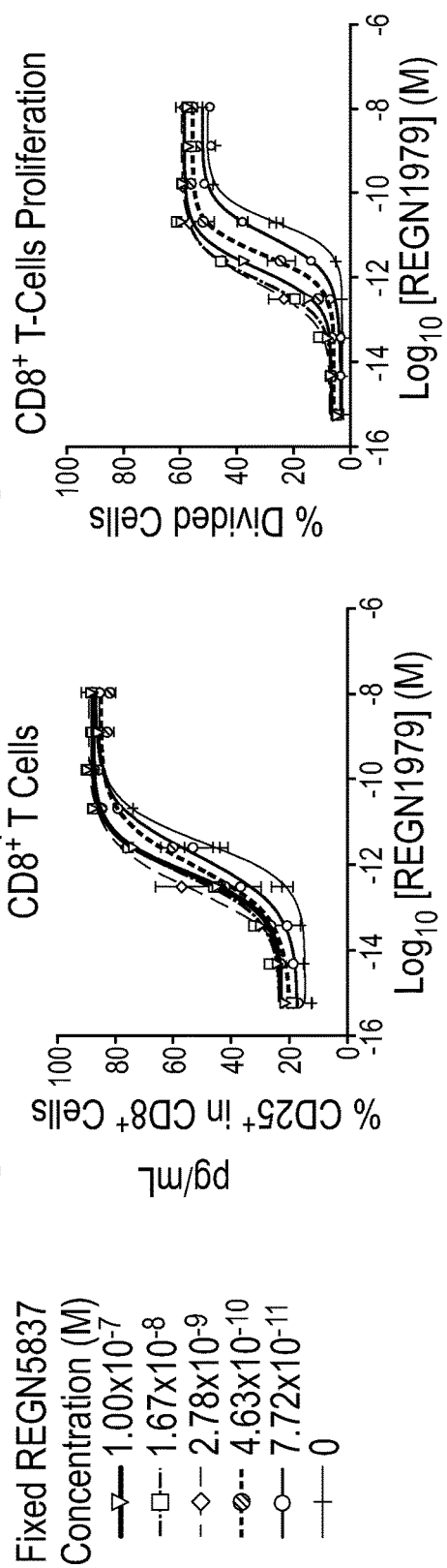

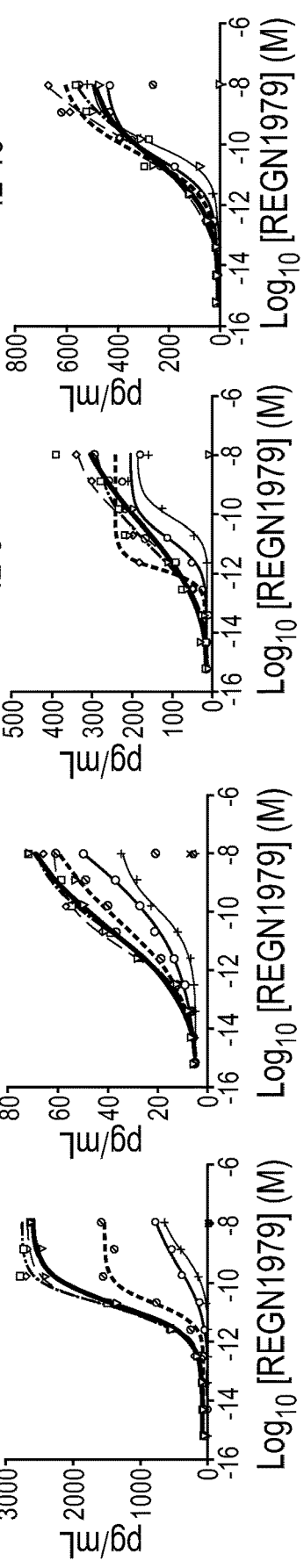
FIG. 12A–12G. REGN5837 Enhances the Potency and Maximal Levels of REGN1979-Mediated Cytokine Release from Human T Cells in a Concentration-Dependent Manner in the Presence of WSU-DLCL2 B-Cell Lymphoma Cells Treatment of NSG Mice Bearing WSU-DLCL2 Tumors with REGN5837 in the Presence of Sub-Efficacious Doses of REGN1979 is Associated with Significant Tumor Suppression

```
                        SEQUENCE LISTING

<160> NUMBER OF SEQ ID NOS: 74

<210> SEQ ID NO 1
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
gaggtgcagc tggtgcagtc tggagcagag gtgaaaaagc ccggggagtc tctgaagatc      60
tcctgtaagg gttctggata caactttgcc acgtactgga ttgcctgggt gcgccagatg     120
cccgggaaag gcctggagtt gatgggaatc atctatcctg gtgactctga gaccacatac     180
aacccgtcct tccaaggcca ggtcaccatc tcagccgaca gtccatcag taacgcctac     240 ctgcagtgga gcagcctgaa ggcctcggac accgccatgt attattgtgc gagagtagga     300
ggatattgta gtggtaccag ttgccacaac tggttcgacc cctggggcct gggaaccctg     360
gtcaccgtct cctca                                                     375

<210> SEQ ID NO 2
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Ala Thr Tyr
            20                  25                  30

Trp Ile Ala Trp Val Arg Gln Met Pro Gly Lys Gly Leu Glu Leu Met
        35                  40                  45

Gly Ile Ile Tyr Pro Gly Asp Ser Glu Thr Thr Tyr Asn Pro Ser Phe
    50                  55                  60

Gln Gly Gln Val Thr Ile Ser Ala Asp Lys Ser Ile Ser Asn Ala Tyr
65                  70                  75                  80

Leu Gln Trp Ser Ser Leu Lys Ala Ser Asp Thr Ala Met Tyr Tyr Cys
                85                  90                  95
```

Ala Arg Val Gly Gly Tyr Cys Ser Gly Thr Ser Cys His Asn Trp Phe
            100                 105                 110

Asp Pro Trp Gly Leu Gly Thr Leu Val Thr Val Ser Ser
        115                 120                 125

<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ggatacaact ttgccacgta ctgg                                            24

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Asn Phe Ala Thr Tyr Trp
1               5

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
atctatcctg gtgactctga gacc                                            24

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Tyr Pro Gly Asp Ser Glu Thr
1               5

<210> SEQ ID NO 7
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gcgagagtag gaggatattg tagtggtacc agttgccaca actggttcga cccc           54

```
<210> SEQ ID NO 8
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Arg Val Gly Gly Tyr Cys Ser Gly Thr Ser Cys His Asn Trp Phe
1               5                   10                  15

Asp Pro

<210> SEQ ID NO 9
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccttg gacgttcggc   300
caagggacca aggtggaaat caaa                                          324

<210> SEQ ID NO 10
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 11
<211> LENGTH: 21
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic oligonucleotide"

<400> SEQUENCE: 11
cagagtgtta gcagcagcta c                                             21

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Ser Val Ser Ser Ser Tyr
1               5

<210> SEQ ID NO 13
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13 ggtgcatcc                                                            9

<210> SEQ ID NO 14
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Ala Ser
1

<210> SEQ ID NO 15
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cagcagtatg gtagctcacc ttggacg                                       27

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Tyr Gly Ser Ser Pro Trp Thr
```

<210> SEQ ID NO 17
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
gaggtgcagc tggtggagtc tgggggaggc ttggtccagc cggggggtc cctgaaactc      60 tcctgtgcag cctctgggtt caccttcagt ggctctgata tgcactgggt ccgccaggct     120
tccgggaaag gctggagtg gttggccgt attagaaacc aacctaatag ttacgcgaca       180
gcatatgctg cgtcggtgaa aggcaggttc accatctcca gagatgattc aaagaacacg    240
gcgcatttgc aaatgaacag cctgaaaacc gaggacacgg ccgtgtattt ttgtactaga    300
caaaagcagg tcgtttataa ttaccatcac tactacggta tggacgtctg gggccaaggg   360
accacggtca ccgtctcctc a                                               381
```

<210> SEQ ID NO 18
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Asp Met His Trp Val Arg Gln Ala Ser Gly Lys Gly Leu Glu Trp Val
        35                  40                  45

Gly Arg Ile Arg Asn Gln Pro Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala His Leu Gln Met Asn Ser Leu Lys Thr Glu Asp Thr Ala Val Tyr
                85                  90                  95

Phe Cys Thr Arg Gln Lys Gln Val Val Tyr Asn Tyr His His Tyr Tyr
            100                 105                 110

Gly Met Asp Val Trp Gly Gln Gly Thr Thr Val Thr Val Ser Ser
        115                 120                 125

<210> SEQ ID NO 19
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19

```
gggttcacct tcagtggctc tgat                                            24
```

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Phe Thr Phe Ser Gly Ser Asp
1               5

<210> SEQ ID NO 21
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
attagaaacc aacctaatag ttacgcgaca                                      30

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ile Arg Asn Gln Pro Asn Ser Tyr Ala Thr
1               5                   10

<210> SEQ ID NO 23
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
actagacaaa agcaggtcgt ttataattac catcactact acggtatgga cgtc          54

<210> SEQ ID NO 24
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Thr Arg Gln Lys Gln Val Val Tyr Asn Tyr His His Tyr Tyr Gly Met
1               5                   10                  15

Asp Val

<210> SEQ ID NO 25
<211> LENGTH: 366
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic CD28-HCVR-NA"

<400> SEQUENCE: 25
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggatcac ccactacaac     180
ccctccctca agagtcgagt caccatatca gtagacacgt ccaagatcca gttctccctg     240
aagctgagtt ctgtgaccgc tgcggacacg gccgtgtatt actgtgcgag atggggggtt     300
cggagggact actactacta cggtatggac gtctggggcc aagggaccac ggtcaccgtc     360
tcctca                                                               366

<210> SEQ ID NO 26
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CD28-HCVR-AA"

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ile Thr His Tyr Asn Pro Ser Leu Lys
    50                  55                  60

Ser Arg Val Thr Ile Ser Val Asp Thr Ser Lys Ile Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Val Arg Arg Asp Tyr Tyr Tyr Tyr Gly Met Asp Val Trp
            100                 105                 110

Gly Gln Gly Thr Thr Val Thr Val Ser Ser
        115                 120

<210> SEQ ID NO 27
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CD28-HCDR1-NA"

<400> SEQUENCE: 27
ggtggctcca tcagtagtta ctac                                            24

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic CD28-HCDR1-AA"

<400> SEQUENCE: 28

Gly Gly Ser Ile Ser Ser Tyr Tyr
1               5

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CD28-HCDR2-NA"

<400> SEQUENCE: 29
atctattaca gtgggatcac c                                              21

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CD28-HCDR2-AA"

<400> SEQUENCE: 30

Ile Tyr Tyr Ser Gly Ile Thr
1               5

<210> SEQ ID NO 31
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CD28- HCDR3-NA"

<400> SEQUENCE: 31
cgagatgggg ggttcggagg gactactact actacggtat ggacgtc                  47

<210> SEQ ID NO 32
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CD28- HCDR3-AA"

<400> SEQUENCE: 32

Ala Arg Trp Gly Val Arg Arg Asp Tyr Tyr Tyr Gly Met Asp Val
1               5                   10                  15

<210> SEQ ID NO 33
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10369N_VH(mouse).mIgG1"

<400> SEQUENCE: 33

Glu Val Gln Leu Gln Gln Ser Gly Ala Glu Val Val Lys Pro Gly Ala
1               5                   10                  15

```
Ser Val Lys Leu Ser Cys Thr Thr Ser Gly Phe Asn Ile Lys Asp Thr
            20                  25                  30

Tyr Ile His Trp Val Arg Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
50                  55                  60

Gln Gly Lys Ala Thr Ile Thr Ser Asp Thr Ser Ser Asn Thr Ala Tyr
65                  70                  75                  80

Leu Gln Phe Thr Ser Leu Thr Ser Glu Asp Ser Ala Val Tyr Tyr Cys
                85                  90                  95

Ala Ile Asn Phe Gly Ser Asn Tyr Asp Ala Ile Asp Tyr Trp Gly Gln
                100                 105                 110

Gly Thr Ser Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430
```

His Thr Glu Lys Ser Leu Ser His Ser Pro Gly Lys
          435                 440

<210> SEQ ID NO 34
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10369N_VK(mouse).mKappa"

<400> SEQUENCE: 34

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Ile
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ile Ile Asn Ser Val Glu Thr
65                  70                  75                  80

Glu Asp Phe Gly Met Tyr Phe Cys Gln Gln Ser Asp Ser Trp Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Gly Glu Cys
    210

<210> SEQ ID NO 35
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 14226P2_VH(human).hIgG4 stealth/star"

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ile Thr His Tyr Asn Pro Ser Leu Lys

Ser Arg Val Thr Ile Ser Val Asp Thr Ser Lys Ile Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Val Arg Arg Asp Tyr Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn Arg Phe Thr Gln Lys Ser Leu Ser Leu Ser Pro Gly Lys
                435                 440                 445

<210> SEQ ID NO 36
<211> LENGTH: 214
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic 3-20 GL VK.hKappa"

<400> SEQUENCE: 36
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu
    210

```
<210> SEQ ID NO 37
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10154P_VH(human).hIgG4 stealth"

<400> SEQUENCE: 37
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Thr Tyr
            20                  25                  30

Ala Met Thr Trp Val Arg Gln Ala Pro Gly Lys Gly Leu Glu Trp Val
        35                  40                  45

Ser Ala Ile Asn Tyr Arg Ala Ala Asn Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Gln Asp Arg Val Ile Ile Lys Asp Tyr Tyr Val Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 38
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 1-39 GL (PP) VK.hKappa"

<400> SEQUENCE: 38

Asp Ile Gln Met Thr Gln Ser Pro Ser Ser Leu Ser Ala Ser Val Gly

-continued

```
1               5                   10                  15
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 39
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence: Synthetic VAC3B9_VH(human).hIgG4"

<400> SEQUENCE: 39

```
Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
            35                  40                  45

Ser Val Ile Ser Trp Asn Ser Asp Ser Ile Gly Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
            85                  90                  95

Ala Lys Asp Asn His Tyr Gly Ser Gly Ser Tyr Tyr Tyr Gln Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
            130                 135                 140
```

```
Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 40
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic FAAR9F07_VH(human).hIgG4 star"

<400> SEQUENCE: 40

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Asn Ser Gly Tyr Gly His Tyr Tyr Gly Met Asp Val
                100                 105                 110

Trp Gly Gln Gly Thr Thr Val Thr Val Ala Ser Ala Ser Thr Lys Gly
                115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn Arg Phe Thr Gln Lys Ser Leu Ser Leu Ser Pro
        435                 440                 445

Gly Lys
```

-continued

450

<210> SEQ ID NO 41
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic FAAR9F07_VK(human).hKappa"

<400> SEQUENCE: 41

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic VAC3B9_VH(human).hIgG4 stealth"

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
            85                  90                  95

Ala Lys Asp Asn His Tyr Gly Ser Gly Ser Tyr Tyr Tyr Gln Tyr
                100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
        130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Lys Thr Tyr
        195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
        450

<210> SEQ ID NO 43
<211> LENGTH: 449

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic FAAR9F07_VH(human).hIgG4 stealth/star"

<400> SEQUENCE: 43

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
                    370                 375                 380
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Arg Leu Thr Val Asp Lys
                    405                 410                 415

Ser Arg Trp Gln Glu Gly Asn Val Phe Ser Cys Ser Val Met His Glu
                420                 425                 430

Ala Leu His Asn Arg Phe Thr Gln Lys Ser Leu Ser Leu Ser Leu Gly
            435                 440                 445

Lys
```

<210> SEQ ID NO 44
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic FAAR9F07_VK(human).hKappa"

<400> SEQUENCE: 44

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic 1238N_VH(human).hIgG4"

<400> SEQUENCE: 45

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Arg Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Ile Tyr Tyr Cys Ala
                85                  90                  95
Arg His Arg Val Thr Arg Thr Ala Asp Ser Phe Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
```

```
                        405                 410                 415
Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
        435                 440                 445

<210> SEQ ID NO 46
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 1238N VK(human).hKappa"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Thr Gly Lys Ala Pro Lys Phe Leu Ile
        35                  40                  45

Tyr Asp Ala Ser Asn Leu Glu Thr Gly Val Ser Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Gly Thr Tyr Tyr Cys His Gln Tyr Gly Asp Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 11838P2_VH(human).hIgG4 stealth (PSMA)"

<400> SEQUENCE: 47

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
         35                  40                  45

Ala Phe Met Ser Tyr Asp Gly Ser Asn Lys Phe Tyr Ser Asp Ser Val
 50                  55                  60

Lys Gly Arg Phe Thr Ile Ser Arg Asp Asn Ser Arg Lys Met Leu Phe
 65                  70                  75                  80

Leu Gln Met Asn Asn Leu Arg Ala Glu Asp Thr Ala Val Tyr Tyr Cys
                 85                  90                  95

Ala Arg Asp Gln Tyr Tyr Asp Phe Leu Thr Asp His Gly Val Phe Asp
                100                 105                 110

Tyr Trp Gly Gln Gly Thr Leu Val Thr Val Ser Ser Ala Ser Thr Lys
             115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445
```

Gly Lys
    450

<210> SEQ ID NO 48
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 14226P2_VH(human).hIgG4 stealth/star (CD28)"

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ile Thr His Tyr Asn Pro Ser Leu Lys
    50                  55                  60

Ser Arg Val Thr Ile Ser Val Asp Thr Ser Lys Ile Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Val Arg Arg Asp Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu

```
                   340                 345                 350
Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn Arg Phe Thr Gln Lys Ser Leu Ser Leu Ser Pro Gly Lys
        435                 440                 445

<210> SEQ ID NO 49
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 3-20 GL VK.hKappa"

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 50
<211> LENGTH: 696
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic REGN5140 hCD22 ecto (D20-R687).mmH"

<400> SEQUENCE: 50

Asp Ser Ser Lys Trp Val Phe Glu His Pro Glu Thr Leu Tyr Ala Trp
1               5                   10                  15

Glu Gly Ala Cys Val Trp Ile Pro Cys Thr Tyr Arg Ala Leu Asp Gly
            20                  25                  30

Asp Leu Glu Ser Phe Ile Leu Phe His Asn Pro Glu Tyr Asn Lys Asn
        35                  40                  45

Thr Ser Lys Phe Asp Gly Thr Arg Leu Tyr Glu Ser Thr Lys Asp Gly
    50                  55                  60

Lys Val Pro Ser Glu Gln Lys Arg Val Gln Phe Leu Gly Asp Lys Asn
65                  70                  75                  80

Lys Asn Cys Thr Leu Ser Ile His Pro Val His Leu Asn Asp Ser Gly
                85                  90                  95

Gln Leu Gly Leu Arg Met Glu Ser Lys Thr Glu Lys Trp Met Glu Arg
            100                 105                 110

Ile His Leu Asn Val Ser Glu Arg Pro Phe Pro Pro His Ile Gln Leu
        115                 120                 125

Pro Pro Glu Ile Gln Glu Ser Gln Glu Val Thr Leu Thr Cys Leu Leu
    130                 135                 140

Asn Phe Ser Cys Tyr Gly Tyr Pro Ile Gln Leu Gln Trp Leu Leu Glu
145                 150                 155                 160

Gly Val Pro Met Arg Gln Ala Ala Val Thr Ser Thr Ser Leu Thr Ile
                165                 170                 175

Lys Ser Val Phe Thr Arg Ser Glu Leu Lys Phe Ser Pro Gln Trp Ser
            180                 185                 190

His His Gly Lys Ile Val Thr Cys Gln Leu Gln Asp Ala Asp Gly Lys
        195                 200                 205

Phe Leu Ser Asn Asp Thr Val Gln Leu Asn Val Lys His Thr Pro Lys
210                 215                 220

Leu Glu Ile Lys Val Thr Pro Ser Asp Ala Ile Val Arg Glu Gly Asp
225                 230                 235                 240

Ser Val Thr Met Thr Cys Glu Val Ser Ser Asn Pro Glu Tyr Thr
                245                 250                 255

Thr Val Ser Trp Leu Lys Asp Gly Thr Ser Leu Lys Lys Gln Asn Thr
            260                 265                 270

Phe Thr Leu Asn Leu Arg Glu Val Thr Lys Asp Gln Ser Gly Lys Tyr
        275                 280                 285

Cys Cys Gln Val Ser Asn Asp Val Gly Pro Gly Arg Ser Glu Glu Val
290                 295                 300

Phe Leu Gln Val Gln Tyr Ala Pro Glu Pro Ser Thr Val Gln Ile Leu
305                 310                 315                 320

His Ser Pro Ala Val Glu Gly Ser Gln Val Glu Phe Leu Cys Met Ser
                325                 330                 335

Leu Ala Asn Pro Leu Pro Thr Asn Tyr Thr Trp Tyr His Asn Gly Lys
            340                 345                 350

Glu Met Gln Gly Arg Thr Glu Glu Lys Val His Ile Pro Lys Ile Leu
        355                 360                 365

Pro Trp His Ala Gly Thr Tyr Ser Cys Val Ala Glu Asn Ile Leu Gly
    370                 375                 380
```

Thr Gly Gln Arg Gly Pro Gly Ala Glu Leu Asp Val Gln Tyr Pro Pro
385                 390                 395                 400

Lys Lys Val Thr Thr Val Ile Gln Asn Pro Met Pro Ile Arg Glu Gly
            405                 410                 415

Asp Thr Val Thr Leu Ser Cys Asn Tyr Asn Ser Ser Asn Pro Ser Val
            420                 425                 430

Thr Arg Tyr Glu Trp Lys Pro His Gly Ala Trp Glu Pro Ser Leu
        435                 440                 445

Gly Val Leu Lys Ile Gln Asn Val Gly Trp Asp Asn Thr Thr Ile Ala
        450                 455                 460

Cys Ala Ala Cys Asn Ser Trp Cys Ser Trp Ala Ser Pro Val Ala Leu
465                 470                 475                 480

Asn Val Gln Tyr Ala Pro Arg Asp Val Arg Val Arg Lys Ile Lys Pro
                485                 490                 495

Leu Ser Glu Ile His Ser Gly Asn Ser Val Ser Leu Gln Cys Asp Phe
                500                 505                 510

Ser Ser Ser His Pro Lys Glu Val Gln Phe Phe Trp Glu Lys Asn Gly
            515                 520                 525

Arg Leu Leu Gly Lys Glu Ser Gln Leu Asn Phe Asp Ser Ile Ser Pro
        530                 535                 540

Glu Asp Ala Gly Ser Tyr Ser Cys Trp Val Asn Asn Ser Ile Gly Gln
545                 550                 555                 560

Thr Ala Ser Lys Ala Trp Thr Leu Glu Val Leu Tyr Ala Pro Arg Arg
                565                 570                 575

Leu Arg Val Ser Met Ser Pro Gly Asp Gln Val Met Glu Gly Lys Ser
                580                 585                 590

Ala Thr Leu Thr Cys Glu Ser Asp Ala Asn Pro Pro Val Ser His Tyr
            595                 600                 605

Thr Trp Phe Asp Trp Asn Asn Gln Ser Leu Pro Tyr His Ser Gln Lys
        610                 615                 620

Leu Arg Leu Glu Pro Val Lys Val Gln His Ser Gly Ala Tyr Trp Cys
625                 630                 635                 640

Gln Gly Thr Asn Ser Val Gly Lys Gly Arg Ser Pro Leu Ser Thr Leu
                645                 650                 655

Thr Val Tyr Tyr Ser Pro Glu Thr Ile Gly Arg Arg Glu Gln Lys Leu
                660                 665                 670

Ile Ser Glu Glu Asp Leu Gly Gly Gln Lys Leu Ile Ser Glu Glu
        675                 680                 685

Asp Leu His His His His His His
        690                 695

<210> SEQ ID NO 51
<211> LENGTH: 697
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic REGN5280 mfCD22 ecto (D18-R686).mmH"

<400> SEQUENCE: 51

Asp Ser Ser Lys Trp Asn Ile Glu His Pro Gly Thr Ile Tyr Ala Trp
1               5                   10                  15

Glu Gly Ala Cys Val Trp Val Pro Cys Thr Tyr Arg Val Leu Asp Gly
            20                  25                  30

Ala Leu Glu Thr Phe Ile Leu Phe His Asn Pro Glu Tyr Asn Gln Asn

```
            35                  40                  45
Met Ser Lys Phe Glu Gly Thr Arg Leu Tyr Glu Ser Thr Lys Asp Gly
 50                  55                  60

Lys Val Pro Ser Gly Gln Lys Arg Val Gln Phe Leu Gly Asn Lys Ile
 65                  70                  75                  80

Asn Asn Asn Cys Thr Leu Ser Ile His Pro Val His Val Asn Asp Ser
                     85                  90                  95

Gly Gln Leu Gly Leu Arg Met Val Ser Lys Thr Glu Lys Trp Met Glu
                    100                 105                 110

Arg Ile His Leu Asn Val Ser Glu Arg Pro Phe Pro Pro Arg Ile Gln
                115                 120                 125

Leu Pro Pro Lys Leu Gln Glu Ser Gln Glu Val Thr Leu Thr Cys Leu
    130                 135                 140

Leu Asn Phe Ser Cys Tyr Gly Tyr Gln Ile Gln Leu Gln Trp Leu Leu
145                 150                 155                 160

Glu Gly Ala Pro Met Arg Gln Ala Ala Val Thr Leu Thr Ser Leu Ser
                    165                 170                 175

Thr Lys Ser Val Phe Thr Arg Ser Glu Leu Lys Phe Ser Pro Gln Trp
                180                 185                 190

Ser His His Gly Lys Ile Val Thr Cys Glu Leu His Asp Val Asp Gly
            195                 200                 205

Lys Val Leu Ser Glu Asp Met Val Gln Leu Asn Val Lys His Thr Pro
210                 215                 220

Lys Leu Thr Ile Glu Val Thr Pro Asn Glu Thr Ile Val Arg Lys Gly
225                 230                 235                 240

Asp Ser Val Thr Met Thr Cys Lys Val Asn Ser Ser Asn Pro Glu Tyr
                    245                 250                 255

Thr Thr Val Ser Trp Leu Lys Asp Gly Ile Leu Leu Lys Glu Gln Asn
                260                 265                 270

Thr Leu Met Leu Thr Leu His Lys Val Thr Lys Ser Gln Ser Gly Arg
            275                 280                 285

Tyr Cys Cys Arg Val Ser Asn Asp Val Gly Pro Ala Thr Ser Glu Lys
        290                 295                 300

Val Phe Leu Gln Val Gln Tyr Ala Pro Glu Pro Ser Arg Val Gln Ile
305                 310                 315                 320

Ser Gln Ser Pro Ala Val Glu Gly Ser Glu Val Asn Phe Leu Cys Ile
                    325                 330                 335

Ser Pro Ala Asn Pro Leu Pro Thr Asn Tyr Thr Trp Tyr His Asn Gly
                340                 345                 350

Lys Glu Val Gln Gly Arg Thr Glu Lys Gln Phe Gln Ile Gln Lys Ile
            355                 360                 365

Leu Pro Trp His Ala Gly Thr Tyr Ser Cys Glu Ala Glu Asn Ile Leu
        370                 375                 380

Gly Ile Gly Glu Arg Gly Pro Gly Thr Glu Leu Asp Val Gln Tyr Pro
385                 390                 395                 400

Pro Lys Lys Val Thr Met Val Ile Glu Asn Pro Thr Pro Ile Arg Glu
                    405                 410                 415

Gly Asp Thr Val Thr Leu Ser Cys Asn Tyr Ser Ser Ser Asn Pro Ile
                420                 425                 430

Val Asn His Tyr Glu Trp Arg Pro Arg Gly Ala Trp Glu Glu Pro Ser
            435                 440                 445

Leu Gly Val Leu Lys Ile Gln Asn Ile Gly Trp Asn Asn Thr Ala Val
450                 455                 460
```

Ala Cys Ala Ala Cys Asn Asn Trp Cys Ser Trp Ala Ser Pro Val Thr
465                 470                 475                 480

Leu Asn Val Leu Tyr Ala Pro Arg Gly Val Arg Val Lys Ile Lys
            485                 490                 495

Pro Leu Ser Glu Ile His Ser Gly Asn Ser Val Ser Leu Gln Cys Asp
        500                 505                 510

Phe Ser Ser Ser His Pro Lys Glu Val Gln Phe Phe Trp Glu Lys Asn
        515                 520                 525

Gly Ser Leu Leu Gly Lys Glu Ser Gln Leu Asn Phe Asp Ser Ile Ser
530                 535                 540

Pro Glu Asp Ala Gly Ser Tyr Ser Cys Trp Val Asn Asn Ser Ile Gly
545                 550                 555                 560

Gln Thr Ala Ser Lys Ala Trp Thr Leu Glu Val Leu Tyr Ala Pro Arg
                565                 570                 575

Arg Leu Arg Val Ser Met Ser Gln Gly Asn Gln Val Met Glu Gly Lys
            580                 585                 590

Thr Ala Thr Leu Thr Cys Glu Ser Asp Ala Asn Pro Pro Val Tyr Ser
        595                 600                 605

Tyr Ala Trp Phe Asp Trp Asn Asn Gln Ser Leu Pro Tyr Ser Gly Arg
610                 615                 620

Met Leu Arg Leu Glu Pro Val Lys Val Gln His Ser Gly Ala Tyr Trp
625                 630                 635                 640

Cys Gln Gly Thr Asn Arg Val Gly Lys Gly His Ser Pro Leu Ile Thr
                645                 650                 655

Leu Thr Val Tyr Tyr Ser Pro Gln Thr Ile Gly Arg Arg Glu Gln Lys
            660                 665                 670

Leu Ile Ser Glu Glu Asp Leu Gly Gly Glu Gln Lys Leu Ile Ser Glu
        675                 680                 685

Glu Asp Leu His His His His His His
    690                 695

<210> SEQ ID NO 52
<211> LENGTH: 696
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic REGN5281 mfCD22 ecto (D20-R687).mmH"

<400> SEQUENCE: 52

Asp Ser Ser Lys Trp Asn Ile Glu His Pro Gly Thr Ile Tyr Ala Trp
1               5                   10                  15

Glu Gly Ala Cys Val Trp Val Pro Cys Thr Tyr Arg Val Leu Asp Gly
            20                  25                  30

Ala Leu Glu Thr Phe Ile Leu Phe His Asn Pro Glu Tyr Asn Gln Asn
        35                  40                  45

Met Ser Lys Phe Glu Gly Thr Arg Leu Tyr Glu Asn Thr Lys Asp Gly
    50                  55                  60

Lys Leu Pro Ser Gly Gln Lys Arg Val Gln Phe Leu Gly Asn Lys Ile
65                  70                  75                  80

Asn Asn Cys Thr Leu Ser Ile His Pro Val His Val Asn Asp Ser Gly
                85                  90                  95

Gln Leu Gly Leu Arg Met Val Ser Lys Thr Glu Lys Trp Met Glu Arg
            100                 105                 110

-continued

```
Ile His Leu Asn Val Ser Glu Arg Pro Phe Pro Arg Ile Gln Leu
            115                 120                 125

Pro Pro Lys Leu Gln Glu Ser Gln Glu Val Thr Leu Thr Cys Leu Leu
130                 135                 140

Asn Phe Ser Cys Tyr Gly Tyr Gln Ile Gln Leu Gln Trp Leu Leu Glu
145                 150                 155                 160

Gly Val Pro Met Arg Gln Ala Ala Val Thr Ser Thr Ser Leu Ser Thr
                165                 170                 175

Lys Ser Val Phe Thr Arg Ser Glu Leu Lys Phe Ser Pro Gln Trp Ser
                180                 185                 190

His His Gly Lys Ile Val Thr Cys Glu Leu His Asp Val Asp Gly Lys
                195                 200                 205

Val Leu Ser Glu Asp Met Val Gln Leu Asn Val Lys His Thr Pro Lys
210                 215                 220

Leu Thr Ile Glu Val Thr Pro Asn Glu Thr Thr Val Arg Lys Gly Asp
225                 230                 235                 240

Ser Val Thr Met Thr Cys Lys Val Asn Ser Ser Asn Pro Glu Tyr Thr
                245                 250                 255

Thr Val Ser Trp Leu Lys Asp Gly Ile Pro Leu Lys Glu Gln Asn Thr
                260                 265                 270

Leu Met Leu Thr Leu His Lys Val Thr Lys Ser Gln Ser Gly Arg Tyr
                275                 280                 285

Cys Cys Arg Val Ser Asn Asp Val Gly Pro Ala Thr Ser Glu Lys Val
                290                 295                 300

Phe Leu Gln Val Gln Tyr Ala Pro Glu Ser Ser Arg Val Gln Ile Ser
305                 310                 315                 320

Gln Ser Pro Ala Val Glu Gly Ser Glu Val Asn Phe Leu Cys Ile Ser
                325                 330                 335

Pro Ala Asn Pro Leu Pro Thr Asn Tyr Thr Trp Tyr His Asn Gly Lys
                340                 345                 350

Glu Val Gln Gly Arg Thr Glu Lys Gln Phe Gln Ile Gln Lys Ile Leu
                355                 360                 365

Pro Trp His Ala Gly Thr Tyr Ser Cys Glu Ala Gly Asn Ile Leu Gly
370                 375                 380

Ile Gly Glu Arg Gly Pro Gly Thr Glu Leu Asp Val Gln Tyr Pro Pro
385                 390                 395                 400

Lys Lys Val Thr Met Val Ile Glu Asn Pro Thr Pro Ile Arg Glu Gly
                405                 410                 415

Asp Thr Val Thr Leu Ser Cys Asn Tyr Ser Ser Ser Asn Pro Ile Val
                420                 425                 430

Asn His Tyr Glu Trp Arg Pro Arg Gly Ala Trp Glu Glu Pro Ser Leu
                435                 440                 445

Gly Val Leu Lys Ile Gln Asn Ile Gly Trp Asn Asn Thr Ala Val Ala
                450                 455                 460

Cys Ala Ala Cys Asn Asn Trp Cys Ser Trp Ala Ser Pro Val Thr Leu
465                 470                 475                 480

Asn Val Leu Tyr Ala Pro Arg Gly Val Arg Val Arg Lys Ile Lys Pro
                485                 490                 495

Leu Ser Glu Ile His Ser Gly Asn Ser Val Ser Leu Gln Cys Asp Phe
                500                 505                 510

Ser Ser Ser His Pro Lys Glu Val Gln Phe Phe Trp Glu Lys Asn Gly
                515                 520                 525

Ser Leu Leu Gly Lys Glu Ser Gln Leu Asn Phe Asp Ser Ile Ser Pro
```

```
                    530                 535                 540
Glu Asp Ala Gly Ser Tyr Ser Cys Trp Val Asn Asn Ser Ile Gly Gln
545                 550                 555                 560

Thr Ala Ser Lys Ala Trp Thr Leu Glu Val Leu Tyr Ala Pro Arg Arg
                565                 570                 575

Leu Arg Val Ser Met Ser Gln Gly Asn Gln Val Met Glu Gly Lys Thr
                    580                 585                 590

Ala Thr Leu Ile Cys Glu Ser Asp Ala Asn Pro Pro Val Tyr Ser Tyr
                595                 600                 605

Ala Trp Phe Asp Trp Asn Asn Gln Ser Leu Pro Tyr Ser Gly Arg Met
            610                 615                 620

Leu Arg Leu Glu Pro Val Lys Val Gln His Ser Gly Ala Tyr Trp Cys
625                 630                 635                 640

Gln Gly Thr Asn Arg Val Gly Lys Gly His Ser Pro Leu Ile Thr Leu
                645                 650                 655

Thr Val Tyr Tyr Ser Pro Gln Thr Ile Gly Arg Arg Glu Gln Lys Leu
                660                 665                 670

Ile Ser Glu Glu Asp Leu Gly Gly Glu Gln Lys Leu Ile Ser Glu Glu
            675                 680                 685

Asp Leu His His His His His His
    690                 695

<210> SEQ ID NO 53
<211> LENGTH: 367
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic REGN2012 hCD28 ecto (N19-P152).mFc"

<400> SEQUENCE: 53

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
                100                 105                 110

Thr Ile Ile His Val Lys Gly Lys His Leu Cys Pro Ser Pro Leu Phe
            115                 120                 125

Pro Gly Pro Ser Lys Pro Glu Pro Arg Gly Pro Thr Ile Lys Pro Cys
130                 135                 140

Pro Pro Cys Lys Cys Pro Ala Pro Asn Leu Leu Gly Gly Pro Ser Val
145                 150                 155                 160

Phe Ile Phe Pro Pro Lys Ile Lys Asp Val Leu Met Ile Ser Leu Ser
                165                 170                 175

Pro Ile Val Thr Cys Val Val Val Asp Val Ser Glu Asp Asp Pro Asp
            180                 185                 190
```

```
Val Gln Ile Ser Trp Phe Val Asn Asn Val Glu Val His Thr Ala Gln
            195                 200                 205

Thr Gln Thr His Arg Glu Asp Tyr Asn Ser Thr Leu Arg Val Val Ser
210                 215                 220

Ala Leu Pro Ile Gln His Gln Asp Trp Met Ser Gly Lys Glu Phe Lys
225                 230                 235                 240

Cys Lys Val Asn Asn Lys Asp Leu Pro Ala Pro Ile Glu Arg Thr Ile
                245                 250                 255

Ser Lys Pro Lys Gly Ser Val Arg Ala Pro Gln Val Tyr Val Leu Pro
            260                 265                 270

Pro Pro Glu Glu Met Thr Lys Lys Gln Val Thr Leu Thr Cys Met
            275                 280                 285

Val Thr Asp Phe Met Pro Glu Asp Ile Tyr Val Glu Trp Thr Asn Asn
290                 295                 300

Gly Lys Thr Glu Leu Asn Tyr Lys Asn Thr Glu Pro Val Leu Asp Ser
305                 310                 315                 320

Asp Gly Ser Tyr Phe Met Tyr Ser Lys Leu Arg Val Glu Lys Lys Asn
                325                 330                 335

Trp Val Glu Arg Asn Ser Tyr Ser Cys Ser Val Val His Glu Gly Leu
            340                 345                 350

His Asn His His Thr Thr Lys Ser Phe Ser Arg Thr Pro Gly Lys
            355                 360                 365

<210> SEQ ID NO 54
<211> LENGTH: 162
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic REGN2011 hCD28 ecto (N19-P152).mmH"

<400> SEQUENCE: 54

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Glu Gln Lys Leu Ile Ser Glu Glu Asp Leu
    130                 135                 140

Gly Gly Glu Gln Lys Leu Ile Ser Glu Glu Asp Leu His His His
145                 150                 155                 160

His His
```

-continued

```
<210> SEQ ID NO 55
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic REGN3595 mCD28 ecto (N20-L150).mmH"

<400> SEQUENCE: 55
```

Asn Lys Ile Leu Val Lys Gln Ser Pro Leu Leu Val Val Asp Ser Asn
1               5                   10                  15

Glu Val Ser Leu Ser Cys Arg Tyr Ser Tyr Asn Leu Leu Ala Lys Glu
            20                  25                  30

Phe Arg Ala Ser Leu Tyr Lys Gly Val Asn Ser Asp Val Glu Val Cys
        35                  40                  45

Val Gly Asn Gly Asn Phe Thr Tyr Gln Pro Gln Phe Arg Ser Asn Ala
    50                  55                  60

Glu Phe Asn Cys Asp Gly Asp Phe Asp Asn Glu Thr Val Thr Phe Arg
65                  70                  75                  80

Leu Trp Asn Leu His Val Asn His Thr Asp Ile Tyr Phe Cys Lys Ile
                85                  90                  95

Glu Phe Met Tyr Pro Pro Pro Tyr Leu Asp Asn Glu Arg Ser Asn Gly
            100                 105                 110

Thr Ile Ile His Ile Lys Glu Lys His Leu Cys His Thr Gln Ser Ser
        115                 120                 125

Pro Lys Leu Glu Gln Lys Leu Ile Ser Glu Glu Asp Leu Gly Gly Glu
    130                 135                 140

Gln Lys Leu Ile Ser Glu Glu Asp Leu His His His His His His
145                 150                 155

```
<210> SEQ ID NO 56
<211> LENGTH: 847
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Human CD22 Amino Acid Sequence: Accession number
      CAA42006"

<400> SEQUENCE: 56
```

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
            85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His

```
                130             135             140
Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
            195                 200                 205

Gln Trp Ser His His Gly Lys Ile Val Thr Cys Gln Leu Gln Asp Ala
        210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
            275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
            355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
            435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Arg Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560
```

```
Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu
                595                 600                 605

Gly Lys Ser Ala Thr Leu Thr Cys Glu Ser Asp Ala Asn Pro Pro Val
                610                 615                 620

Ser His Tyr Thr Trp Phe Asp Trp Asn Asn Gln Ser Leu Pro His His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
                660                 665                 670

Ser Thr Leu Thr Val Tyr Tyr Ser Pro Glu Thr Ile Gly Arg Arg Val
                675                 680                 685

Ala Val Gly Leu Gly Ser Cys Leu Ala Ile Leu Ile Leu Ala Ile Cys
                690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
                740                 745                 750

Asn Pro Met Met Glu Asp Gly Ile Ser Tyr Thr Thr Leu Arg Phe Pro
                755                 760                 765

Glu Met Asn Ile Pro Arg Thr Gly Asp Ala Glu Ser Ser Glu Met Gln
770                 775                 780

Arg Pro Pro Arg Thr Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
                820                 825                 830

Arg Pro Gln Ala Gln Glu Asn Val Asp Tyr Val Ile Leu Lys His
                835                 840                 845

<210> SEQ ID NO 57
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic epitope of CD22 bound by REGN5837 (mAb33037P2)"

<400> SEQUENCE: 57

Asn Val Gln Tyr Ala Pro Arg Asp Val Arg Val Arg Lys Ile Lys Pro
1               5                   10                  15

Leu Ser Glu Ile His Ser Gly Asn Ser
                20                  25

<210> SEQ ID NO 58
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic epitope of CD22 bound by REGN5837 (mAb33037P2)"

<400> SEQUENCE: 58

Phe Trp Glu Lys Asn Gly Arg Leu Leu Gly Lys Glu Ser Gln Leu Asn
1               5                   10                  15

Phe

<210> SEQ ID NO 59
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic epitope of CD22 bound by REGN5838 (mAb33041P2)"

<400> SEQUENCE: 59

Cys Glu Val Ser Ser Ser Asn Pro Glu Tyr Thr Thr Val Ser Trp Leu
1               5                   10                  15

Lys Asp Gly Thr Ser Leu Lys Lys Gln Asn Thr Phe Thr Leu Asn Leu
            20                  25                  30

<210> SEQ ID NO 60
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 60

His His His His His His
1               5

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000
```

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74
<211> LENGTH: 220
<212> TYPE: PRT
<213> ORGANISM: Homo sapiens

<400> SEQUENCE: 74

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80
```

```
Lys Thr Gly Phe Asn Cys Asp Gly Lys Leu Gly Asn Glu Ser Val Thr
                85              90              95

Phe Tyr Leu Gln Asn Leu Tyr Val Asn Gln Thr Asp Ile Tyr Phe Cys
            100             105             110

Lys Ile Glu Val Met Tyr Pro Pro Tyr Leu Asp Asn Glu Lys Ser
        115             120             125

Asn Gly Thr Ile Ile His Val Lys Gly Lys His Leu Cys Pro Ser Pro
    130             135             140

Leu Phe Pro Gly Pro Ser Lys Pro Phe Trp Val Leu Val Val Val Gly
145             150             155             160

Gly Val Leu Ala Cys Tyr Ser Leu Leu Val Thr Val Ala Phe Ile Ile
                165             170             175

Phe Trp Val Arg Ser Lys Arg Ser Arg Leu Leu His Ser Asp Tyr Met
            180             185             190

Asn Met Thr Pro Arg Arg Pro Gly Pro Thr Arg Lys His Tyr Gln Pro
            195             200             205

Tyr Ala Pro Pro Arg Asp Phe Ala Ala Tyr Arg Ser
210             215             220
```

BISPECIFIC ANTI-CD28 × ANTI-CD22 ANTIBODIES AND USES THEREOF

RELATED APPLICATIONS

This application claims the benefit of priority to U.S. Provisional Application No. 62/781,689, filed on Dec. 19, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 10, 2019, is named 118003_49202_SL.txt and is 104,353 bytes in size.

FIELD OF THE INVENTION

The present invention relates to bispecific antigen-binding molecules that bind CD28 and a target molecule, such as CD22, and methods of use thereof.

BACKGROUND

CD28 is a type I transmembrane protein expressed on the surface of T cells, which has a single extracellular Ig-V-like domain assembled as a homodimer. CD28 is the receptor for the CD80 (B7.1) and CD86 (B7.2) proteins and is activated by CD80 or CD86 expressed on antigen-presenting cells (APCs). The binding of CD28 to CD80 or CD86 provides co-stimulatory signals important for T cell activation and survival. T cell stimulation through CD28, in addition to the T-cell receptor (TCR), provides a potent signal for the production of various interleukins. CD28 also potentiates cellular signals such as pathways controlled by the NFκB transcription factor after TCR activation. The CD28 co-signal is important for effective T-cell activation such as T cell differentiation, proliferation, cytokine release and cell-death.

Anti-CD28 antibodies have been proposed for therapeutic purposes involving the activation of T cells. One particular anti-CD28 antibody, TGN1412 (anti-CD28 superagonist), was used in a clinical trial in 2006. Six healthy volunteers were dosed intravenously with TGN1412 (anti-CD28 super-agonist) at a dose of 0.1 mg/kg. Within two hours, all six patients had significant inflammatory responses (cytokine storm), and all patients were in multi-organ failure within sixteen hours. Subjects were treated with cortocosteroids, and cytokine levels returned to normal levels within 2-3 days. The starting dose of 0.1 mg/kg in a Phase 1 study (associated with CRS) was based on 500-fold multiple of cynomolgus "NOAEL" of 50 mg/kg (Suntharalingam, et al., Cytokine Storm in a Phase 1 Trial of the Anti-CD28 Monoclonal Antibody TGN1412, NEJM 355:1018-1028 (2006)). Unfortunately, TGN1412 induced a cytokine storm, which was not predicted by toxicology studies in cynomolgus macaques or ex vivo human PBMC studies.

CD22 (also known as Siglec-2), a member of Siglec family, specifically recognizes α2,6 sialic acid, and is a transmembrane protein preferentially expressed on B lymphocytes (B cells).

CD22 has a number of ascribed functions including, for example, B cell homeostasis, B cell survival and migration, dampening TLR and CD40 signaling, and inhibiting B cell receptor (BCR) signaling via recruitment of SH2 domain-containing phosphatases by phosphorylation of immunoreceptor tyrosine-based inhibition motifs (ITIMs) in the cytoplasmic region, as well as facilitation of adhesion between B cells and other cell types.

CD22 is not found on the surface of B cells during the early stages of development, nor is it expressed in stem cells. However, 60-70% of all B-cell lymphomas and leukemias express CD22.

An anti-CD22 antibody for treating B-cell lymphomas and leukemias has been investigated. However, the monoclonal antibody, Epratuzumab, had limited success. (Grant, et al. (2013) *Cancer* 119(21): 10.1002/cncr.28299)

Accordingly, there is a need in the art for improved anti-CD22-antibodies. There is also a need for anti-CD28 antibody that is safe for use in a pharmaceutical composition. Furthermore, bispecific antigen-binding molecules that bind both CD28 and a target antigen (such as CD22) would be useful in therapeutic settings in which specific targeting and T cell-mediated killing of cells that express the target antigen is desired.

BRIEF SUMMARY OF THE INVENTION

In a first aspect, the present invention provides bispecific antigen-binding molecules that bind CD28 and a target antigen. According to certain exemplary embodiments, the bispecific antigen-binding molecules bind CD28 and CD22; such bispecific antigen-binding molecules are also referred to herein as "anti-CD28/anti-CD22 bispecific molecules." The anti-CD22 portion of the anti-CD28/anti-CD22 bispecific molecule is useful for targeting cancer cells that express CD22 (e.g., a cancerous B cell), and the anti-CD28 portion of the bispecific molecule is useful for activating T-cells. The simultaneous binding of CD22 on a cancer cell and CD28 on a T-cell facilitates directed killing (cell lysis) of the targeted cancer cell by the activated T-cell, e.g., after TCR activation of the T cell. The anti-CD28/anti-CD22 bispecific molecules of the invention are therefore useful, inter alia, for treating diseases and disorders related to or caused by CD22-expressing tumors (e.g., a B cell proliferative disorder, e.g., a B cell lymphoma, e.g., diffuse large B-cell lymphoma (DLBCL), follicular lymphoma (FL), a marginal zone lymphoma).

The bispecific antigen-binding molecules according to this aspect of the present invention comprise a first antigen-binding domain that specifically binds human CD28, and a second antigen-binding domain that specifically binds CD22. The present invention includes anti-CD28/anti-CD22 bispecific molecules (e.g., bispecific antibodies) wherein each antigen-binding domain comprises a heavy chain variable region (HCVR) paired with a light chain variable region (LCVR). In certain exemplary embodiments of the invention, the anti-CD28 antigen-binding domain and the anti-CD22 antigen binding domain each comprise different, distinct HCVRs paired with a common LCVR.

The present invention provides anti-CD28/anti-CD22 bispecific molecules, wherein the first antigen-binding domain that specifically binds CD28 comprises any of the HCVR amino acid sequences as set forth in Table 6. The first antigen-binding domain that specifically binds CD28 may also comprise any of the LCVR amino acid sequences as set forth in Table 6. According to certain embodiments, the first antigen-binding domain that specifically binds CD28 comprises any of the HCVR/LCVR amino acid sequence pairs as set forth in Table 6. The present invention also provides anti-CD28/anti-CD22 bispecific molecules, wherein the first antigen-binding domain that specifically binds CD28 comprises any of the heavy chain CDR1-CDR2-CDR3 amino acid sequences as set forth in Table 6, and/or any of the light chain CDR1-CDR2-CDR3 amino acid sequences as set forth in Table 6.

According to certain embodiments, the present invention provides anti-CD28/anti-CD22 bispecific molecules, wherein the first antigen-binding domain that specifically binds CD28 comprises a heavy chain variable region (HCVR) having an amino acid sequence selected from the group consisting of SEQ ID NOs: 28 and 26 or a substantially similar sequence thereof having at least 90%, at least 95%, at least 98% or at least 99% sequence identity.

The present invention also provides anti-CD28/anti-CD22 bispecific molecules, wherein the first antigen-binding domain that specifically binds CD28 comprises a light chain variable region (LCVR) having the amino acid sequence of SEQ ID NO: 10, or a substantially similar sequence thereof having at least 90%, at least 95%, at least 98% or at least 99% sequence identity.

The present invention also provides anti-CD28/anti-CD22 bispecific molecules, wherein the first antigen-binding domain that specifically binds CD28 comprises a HCVR and LCVR (HCVR/LCVR) amino acid sequence pair selected from the group consisting of SEQ ID NOs: 28/10 and 26/10.

The present invention also provides anti-CD28/anti-CD22 bispecific molecules, wherein the first antigen-binding domain that specifically binds CD28 comprises a heavy chain CDR3 (HCDR3) domain having the amino acid sequence of SEQ ID NO: 32, or a substantially similar sequence thereto having at least 90%, at least 95%, at least 98% or at least 99% sequence identity; and a light chain CDR3 (LCDR3) domain having the amino acid sequence of SEQ ID NO: 16, or a substantially similar sequence thereof having at least 90%, at least 95%, at least 98% or at least 99% sequence identity.

In certain embodiments, the first antigen-binding domain that specifically binds CD28 comprises the HCDR3/LCDR3 amino acid sequence pair of SEQ ID NOs: 32/16.

The present invention also provides anti-CD28/anti-CD22 bispecific antigen-binding molecules, wherein the first antigen-binding domain that specifically binds CD28 comprises a heavy chain CDR1 (HCDR1) domain having the amino acid sequence of SEQ ID NO: 28, or a substantially similar sequence thereof having at least 90%, at least 95%, at least 98% or at least 99% sequence identity; a heavy chain CDR2 (HCDR2) domain having the amino acid sequence of SEQ ID NO: 30, or a substantially similar sequence thereof having at least 90%, at least 95%, at least 98% or at least 99% sequence identity; a light chain CDR1 (LCDR1) domain having the amino acid sequence of SEQ ID NO: 12, or a substantially similar sequence thereof having at least 90%, at least 95%, at least 98% or at least 99% sequence identity; and a light chain CDR2 (LCDR2) domain having the amino acid sequence of SEQ ID NO: 14, or a substantially similar sequence thereof having at least 90%, at least 95%, at least 98% or at least 99% sequence identity.

Certain non-limiting, exemplary anti-CD28/anti-CD22 bispecific antigen-binding molecules of the invention include a first antigen-binding domain that specifically binds CD28 comprising HCDR1-HCDR2-HCDR3-LCDR1-LCDR2-LCDR3 domains, respectively, having the amino acid sequence of: SEQ ID NOs: 28-30-32-12-14-16.

The present invention also provides anti-CD28/anti-CD22 bispecific molecules, wherein the second antigen-binding domain that specifically binds CD22 comprises a heavy chain variable region (HCVR) having the amino acid sequence selected from the group consisting SEQ ID NOs: 2 and 18, or a substantially similar sequence thereof having at least 90%, at least 95%, at least 98% or at least 99% sequence identity.

The present invention also provides anti-CD28/anti-CD22 bispecific molecules, wherein the second antigen-binding domain that specifically binds CD22 comprises a light chain variable region (LCVR) having the amino acid sequence selected of SEQ ID NO: 10, or a substantially similar sequence thereof having at least 90%, at least 95%, at least 98% or at least 99% sequence identity.

The present invention also provides anti-CD28/anti-CD22 bispecific molecules, wherein the second antigen-binding domain that specifically binds CD22 comprises a HCVR and LCVR (HCVR/LCVR) amino acid sequence pair selected from the group consisting of SEQ ID NOs: 2/10 and 18/10.

The present invention also provides anti-CD28/anti-CD22 bispecific molecules, wherein the second antigen-binding domain that specifically binds CD22 comprises a heavy chain CDR3 (HCDR3) domain having the amino acid sequence selected from the group consisting of SEQ ID NOs: 8 and 24, or a substantially similar sequence thereto having at least 90%, at least 95%, at least 98% or at least 99% sequence identity; and a light chain CDR3 (LCDR3) domain having the amino acid sequence selected of SEQ ID NO:16, or a substantially similar sequence thereof having at least 90%, at least 95%, at least 98% or at least 99% sequence identity.

In certain embodiments, the second antigen-binding domain that specifically binds CD22 comprises a HCDR3/LCDR3 amino acid sequence pair selected from the group consisting of SEQ ID NOs: 8/16 and 24/16.

The present invention also provides anti-CD28/anti-CD22 bispecific antigen-binding molecules, wherein the second antigen-binding domain that specifically binds CD22 comprises a heavy chain CDR1 (HCDR1) domain having the amino acid sequence selected from the group consisting of SEQ ID NOs: 4 and 20, or a substantially similar sequence thereof having at least 90%, at least 95%, at least 98% or at least 99% sequence identity; a heavy chain CDR2 (HCDR2) domain having the amino acid sequence selected from the group consisting of SEQ ID NOs: 6 and 22, or a substantially similar sequence thereof having at least 90%, at least 95%, at least 98% or at least 99% sequence identity; a light chain CDR1 (LCDR1) domain having the amino acid sequence of SEQ ID NO: 12, or a substantially similar sequence thereof having at least 90%, at least 95%, at least 98% or at least 99% sequence identity; and a light chain CDR2 (LCDR2) domain having the amino acid sequence of SEQ ID NO: 14, or a substantially similar sequence thereof having at least 90%, at least 95%, at least 98% or at least 99% sequence identity.

Certain non-limiting, exemplary anti-CD28/anti-CD22 bispecific antigen-binding molecules of the invention include a second antigen-binding domain that specifically binds CD22 comprising HCDR1-HCDR2-HCDR3-LCDR1-LCDR2-LCDR3 domains, respectively, having the amino acid sequences selected from the group consisting of: SEQ ID NOs: 4-6-8-12-14-16 and 20-22-24-12-14-16

In a related embodiment, the invention includes anti-CD28/anti-CD22 bispecific antigen binding molecules wherein the second antigen-binding domain that specifically binds CD22 comprises the heavy and light chain CDR domains contained within heavy and light chain variable region (HCVR/LCVR) sequences selected from the group consisting of SEQ ID NOs: 2/10 and 18/10.

In another aspect, the present invention provides nucleic acid molecules encoding any of the HCVR, LCVR or CDR sequences of the anti-CD28/anti-CD22 bispecific antigen-binding molecules disclosed herein, including nucleic acid molecules comprising the polynucleotide sequences as set forth in Table 7 herein, as well as nucleic acid molecules comprising two or more of the polynucleotide sequences as set forth in Table 7 in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-CD28/anti-CD22 bispecific antigen-binding molecules wherein any of the aforementioned antigen-binding domains that specifically bind CD28 is combined, connected or otherwise associated with any of the aforementioned antigen binding domains that specifically bind CD22 to form a bispecific antigen-binding molecule that binds CD28 and CD22.

The present invention includes anti-CD28/anti-CD22 bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) *JBC* 277:26733). In other applications, modification of galactosylation can be made in order to modify complement dependent cytotoxicity (CDC).

In another aspect, the invention provides a pharmaceutical composition comprising an anti-CD28/anti-CD22 bispecific antigen-binding molecule as disclosed herein and a pharmaceutically acceptable carrier. In a related aspect, the invention features a composition which is a combination of an anti-CD28/anti-CD22 bispecific antigen-binding molecule and a second therapeutic agent. In one embodiment, the second therapeutic agent is any agent that is advantageously combined with an anti-CD28/anti-CD22 bispecific antigen-binding molecule. Exemplary agents that may be advantageously combined with an anti-CD28/anti-CD22 bispecific antigen-binding molecule are discussed in detail elsewhere herein.

In yet another aspect, the invention provides therapeutic methods for targeting/killing cancer cells expressing CD22 using an anti-CD28/anti-CD22 bispecific antigen-binding molecule of the invention, wherein the therapeutic methods comprise administering a therapeutically effective amount of a pharmaceutical composition comprising an anti-CD28/anti-CD22 bispecific antigen-binding molecule of the invention to a subject in need thereof.

The present invention also includes the use of an anti-CD28/anti-CD22 bispecific antigen-binding molecule of the invention in the manufacture of a medicament for the treatment of a disease or disorder related to or caused by CD22 expression.

In yet another aspect, the invention provides therapeutic methods for targeting/killing cancer cells expressing CD22 using an anti-CD28/anti-CD22 bispecific antigen-binding molecule of the invention, wherein the anti-CD28/anti-CD22 bispecific antigen-binding molecule is combined with other anti-tumor bispecific antigen-binding molecules that bind to CD3 (e.g., anti-CD28/anti-CD22 combined with anti-CD3/anti-CD20 antibodies).

In still another aspect, the invention provides therapeutic methods for targeting/killing cancer cells expressing CD22 using an anti-CD28/anti-CD22 bispecific antigen-binding molecule of the invention, wherein the anti-CD28/anti-CD22 bispecific antigen-binding molecule is combined with a checkpoint inhibitor targeting PD-1, PD-L1 or CTLA-4 (e.g., anti-CD28/anti-CD-22 combined with anti-PD-1 antibodies). For example, in certain embodiments, the anti-CD28/anti-CD22 antibodies of the invention may be combined with agents that target PD-1, such as Pembrolizumab (Keytruda®), Nivolumab (Opdivo®), or Cemiplimab (Libtayo®). In certain embodiments, the anti-CD28/anti-CD22 antibodies of the invention may be combined with agents that target PD-L1, such as Atezolizumab (Tecentriq®), Avelumab (Bavencio®), or Durvalumab (Imfinzi®). In certain embodiments, the anti-CD28/anti-CD22 antibodies of the invention may be combined with agents that target CTLA-4, such as Ipilimumab (Yervoy®).

In still another aspect, the invention provides therapeutic methods for targeting/killing cancer cells expressing CD22 using an anti-CD28/anti-CD22 bispecific antigen-binding molecule of the invention, wherein the anti-CD28/anti-CD22 bispecific antigen-binding molecule is combined with other anti-tumor bispecific antigen-binding molecules that binds to CD3 (e.g., anti-CD28/anti-CD22 combined with anti-CD3/anti-CD20 bispecific antibodies, for example, REGN1979 (See U.S. Pat. No. 9,657,102, wherein the anti-CD20 arm comprises the HCVR/LCVR amino acid pair of SEQ ID NOs: 1242/1258 and the anti-CD3 arm comprises the amino acid pair of SEQ ID NOs: 1250/1258)) and/or a checkpoint inhibitor targeting PD-1, PD-L1 or CTLA-4 (e.g., anti-CD28/anti-CD22 combined with anti-PD-1 antibodies). For example, in certain embodiments, the anti-CD28/anti-CD22 antibodies of the invention may be combined with agents that target PD-1, such as Pembrolizumab (Keytruda®), Nivolumab (Opdivo®), or Cemiplimab (Libtayo®, see for example, U.S. Pat. No. 9,987,500, wherein cemiplimab comprises the HCVR/LCVR amino acid pair of SEQ ID NOs: 162/170)). In certain embodiments, the anti-CD28/anti-CD22 antibodies of the invention may be combined with agents that target PD-L1, such as Atezolizumab (Tecentriq®), Avelumab (Bavencio®), or Durvalumab (Imfinzi®). In certain embodiments, the anti-CD28/anti-CD22 antibodies of the invention may be combined with agents that target CTLA-4, such as Ipilimumab (Yervoy®).

Other embodiments will become apparent from a review of the ensuing detailed description.

BRIEF DESCRIPTION OF THE FIGURES

FIGS. 2A and 2B are a set of graphs depicting that anti-CD28/anti-CD22 bispecific antibodies show increased Luciferase production in the presence of primary T-cell stimulation and CD22 target expression. FIG. 2A is a set of graphs depicting the activation of engineered reporter T-cells co-incubated with HEK293/hCD20, HEK293/hCD20/hCD22, or Raji/CD80 and CD86 negative cells in addition to 200 pM constant REGN1945 (a negative hIgG4 isotype control), as assessed by Luciferase production. FIG. 2B is a set of graphs depicting the activation of engineered reporter T-cells co-incubated with HEK293/hCD20, HEK293/hCD20/hCD22, or Raji/CD80 and CD86 negative cells in addition to 200 pM constant REGN2281 (anti-CD20×anti-CD3), as assessed by Luciferase production.

FIG. 3A is a set of graphs depicting the activation of CD4+ T-cells co-incubated with HEK293/hCD20, HEK293/hCD20/hCD22, or Raji/CD80 and CD86 negative cells in the presence of 2 nM constant REGN1945 (hIgG4 isotype control), as assessed by IL-2 production. FIG. 3B is a set of graphs depicting the activation of CD4+ T-cells co-incubated with HEK293/hCD20, HEK293/hCD20/hCD22, or Raji/CD80 and CD86 negative cells in the presence of 2 nM constant REGN2281 (anti-CD20×anti-CD3), as assessed by IL-2 production.

FIG. 7A is a graph depicting the percent survival of Nalm6 cells in the presence of the indicated antibodies. FIG. 7B is a graph depicting the percent of CD8+ cells expressing CD25 (CD25+) in the presence of the indicated antibodies. FIG. 7C is a graph depicting the proliferation of CD25+CD8+ cells as assessed by CellTrace violet dilution in the presence of the indicated antibodies.

FIGS. 8A, 8B and 8C are graphs showing that REGN1979 activated and directed human T cells to kill WSU-DLCL2 cells in a dose dependent manner. More specifically, FIG. 8A is a graph depicting the percent survival of WSU-DLCL2 cells in the presence of the indicated antibodies. FIG. 8B is a graph depicting the percent of CD8+ cells expressing CD25 (CD25+) in the presence of the indicated antibodies. FIG. 8C is a graph depicting the proliferation of CD8+ cells, expressed as % divided, in the presence of the indicated antibodies.

FIGS. 10A-10E are graphs showing that REGN1979 activated and directed human T cells to deplete NHL in a dose-dependent manner. The addition of a fixed concentration of CD22×CD28 bispecific antibodies to REGN1979 enhanced the cytotoxic efficacy (EC50) of REGN1979 2.3 and 3.5 fold when compared to REGN1979 with 1-arm CD28 control antibody or no costimulatory control. The observed target-cell lysis mediated by REGN1979 was associated with T cell activation and proliferation, as measured by CD25 upregulation on CD8+ and CD4+ cells or CellTrace violet dilution respectively. More specifically, FIG. 10A is a graph depicting the percent survival of NHL cells from patient bone marrow in the presence of the indicated antibodies. FIG. 10B is a graph depicting the percent of CD8+ cells expressing CD25 (CD25+) in the presence of the indicated antibodies. FIG. 10C is a graph depicting the proliferation of CD8+ cells as assessed by CellTrace violet dilution in the presence of the indicated antibodies. FIG. 10D is a graph depicting the percent of CD4+ cells expressing CD25 (CD25+) in the presence of the indicated antibodies. FIG. 10E is a graph depicting the proliferation of CD4+ cells as assessed by CellTrace violet dilution in the presence of the indicated antibodies.

FIGS. 11A-11E are graphs showing that REGN5837 Enhances the potency of REGN1979-mediated cytotoxicity, cell-surface expression of CD25, and T-Cell proliferation in a concentration-dependent manner. Briefly, WSU-DLCL2 cells were incubated with lymphocyte-enriched human PBMC at a target cell to PBMC ratio of 1:5 and with anti-CD20×CD3 (REGN1979) at a range of concentrations (4.8 fM to 10 nM) as a single agent (ie, no REGN5837) or in the presence of fixed concentrations of REGN5837 (ranging from 0.01 to 15 μg/mL) for 72 hours at 37° C. A condition lacking REGN1979 contains REGN5837 alone at the concentration indicated, and is plotted as 0.04 pM. Viable cells were detected by flow cytometry using LIVE/DEAD cell stain (11A). Violet Cell Tracker dye and a phenotyping cocktail of fluorophore-labeled antibodies to CD2, CD4, CD8, and CD25 was used to detect T-cell activation (measured as CD25 expression; 11B, 11D) and CD4+ and CD8+ T-cell proliferation by flow cytometry (11C, 11E).

More specifically, FIG. 11A is a graph depicting the % of dead cells with the indicated concentrations of REGN5837. FIG. 11B is graph depicting the percent of CD25+CD4+ cells with the indicated concentrations of REGN5837. FIG. 11C is a graph depicting the proliferation of CD4+ cells as assessed by CellTrace violet dilution with the indicated concentrations of REGN5837. FIG. 11D is graph depicting the percent of CD25+CD8+ cells. FIG. 11E is a graph depicting the proliferation of CD8+ cells as assessed by CellTrace violet dilution with the indicated concentrations of REGN5837.

FIGS. 12A-12G are graphs showing that REGN5837 enhances the potency and maximal levels of REGN1979-mediated cytokine release from human T cells in a concentration-dependent manner in the presence of WSU-DLCL2 B-cell lymphoma cells. Briefly, WSU-DLCL2 cells were incubated with lymphocyte-enriched human PBMC at a target cell to PBMC ratio of 1:5 and with anti-CD20×CD3 (REGN1979) at a range of concentrations (4.8 fM to 10 nM) as a single agent (i.e., no REGN5837) or in the presence of fixed concentrations of REGN5837 (ranging from 0.01 to 15 μg/mL) for 72 hours at 37° C. A condition lacking REGN1979 contains REGN5837 alone at the concentration indicated, and is plotted as 0.04 pM. Supernatants were assessed for cytokine release of (12A) IL-2, (12B) IL-4, (12C) IL-6, (12D) IL-10, (12E) TNF-α, (12F) IFN-γ, and (12G) IL-17a using a BD Cytometric Bead Array Human Th1/Th2/Th17 Cytokine Kit.

More specifically, FIG. 12A is a graph depicting the level of IL-2 released from human T cells in the presence of WSU-DLCL2 cells with the indicated concentrations of REGN5837. FIG. 12B is a graph depicting the level of IL-4 released from human T cells in the presence of WSU-DLCL2 cells WSU-DLCL2 cells with the indicated concentrations of REGN5837. FIG. 12C is a graph depicting the level of IL-6 released from human T cells in the presence of WSU-DLCL2 cells WSU-DLCL2 cells with the indicated concentrations of REGN5837. FIG. 12D is a graph depicting the level of IL-10 released from human T cells in the presence of WSU-DLCL2 cells WSU-DLCL2 cells with the indicated concentrations of REGN5837. FIG. 12E is a graph depicting the level of TNF-α released from human T cells in the presence of WSU-DLCL2 cells WSU-DLCL2 cells with the indicated concentrations of REGN5837. FIG. 12F is a graph depicting the level of IFN-γ released from human T cells in the presence of WSU-DLCL2 cells WSU-DLCL2 cells with the indicated concentrations of REGN5837. FIG. 12G is a graph depicting the level of IL-17α released from human T cells in the presence of WSU-DLCL2 cells WSU-DLCL2 cells with the indicated concentrations of REGN5837.

More specifically, FIG. 13A is a graph depicting tumor growth in mice administered 1 mg/kg REGN5837 and 0.4 mg/kg REGN1979 (or non-bridging controls, non-TAA× CD3). FIG. 13B is a graph depicting tumor growth in mice administered 1 mg/kg REGN5837 and 4 mg/kg (or non-bridging controls, non-TAA×CD3).

DETAILED DESCRIPTION

Figure 1:
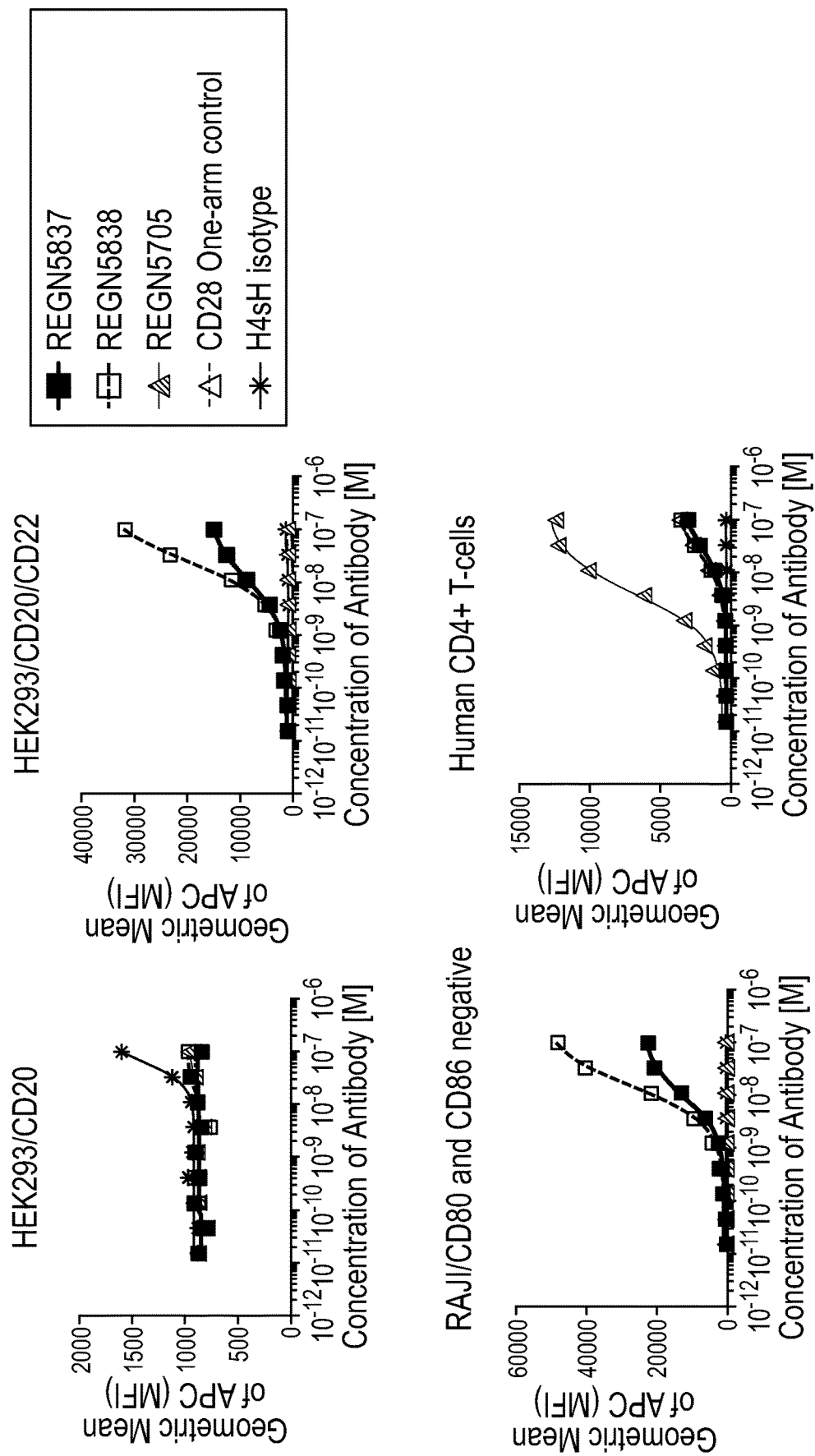
FIG. 1 is a set of graphs depicting the binding of anti-CD28/anti-CD22 bispecific antibodies to human CD4+ T-cells expressing CD28 and target cells expressing human CD22 on the cell surface.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD28," as used herein, refers to an antigen which is expressed on T cells as a costimulatory receptor. Human CD28 comprises the amino acid sequence as set forth in SEQ ID NO: 74, and/or having the amino acid sequence as set forth in NCBI accession No. NP_006130.1. All references to proteins, polypeptides and protein fragments herein are intended to refer to the human version of the respective protein, polypeptide or protein fragment unless explicitly specified as being from a non-human species. Thus, the expression "CD28" means human CD28 unless specified as being from a non-human species, e.g., "mouse CD28," "monkey CD28," etc.

As used herein, "an antibody that binds CD28" or an "anti-CD28 antibody" includes antibodies and antigen-binding fragments thereof that specifically recognize a monomeric CD28, as well as antibodies and antigen-binding fragments thereof that specifically recognize a dimeric CD28. The antibodies and antigen-binding fragments of the present invention may bind soluble CD28 and/or cell surface expressed CD28. Soluble CD28 includes natural CD28 proteins as well as recombinant CD28 protein variants such as, e.g., monomeric and dimeric CD28 constructs, that lack a transmembrane domain or are otherwise unassociated with a cell membrane.

As used herein, the expression "cell surface-expressed CD28" means one or more CD28 protein(s) that is/are expressed on the surface of a cell in vitro or in vivo, such that at least a portion of a CD28 protein is exposed to the extracellular side of the cell membrane and is accessible to an antigen-binding portion of an antibody. "Cell surface-expressed CD28" includes CD28 proteins contained within the context of a functional T cell costimulatory receptor in the membrane of a cell. The expression "cell surface-expressed CD28" includes CD28 protein expressed as part of a homodimer on the surface of a cell. A "cell surface-expressed CD28" can comprise or consist of a CD28 protein expressed on the surface of a cell which normally expresses CD28 protein. Alternatively, "cell surface-expressed CD28" can comprise or consist of CD28 protein expressed on the surface of a cell that normally does not express human CD28 on its surface but has been artificially engineered to express CD28 on its surface.

As used herein, the expression "anti-CD28 antibody" includes both monovalent antibodies with a single specificity, as well as bispecific antibodies comprising a first arm that binds CD28 and a second arm that binds a second (target) antigen, wherein the anti-CD28 arm comprises any of the HCVR/LCVR or CDR sequences as set forth in Table 1 herein. Examples of anti-CD28 bispecific antibodies are described elsewhere herein. The term "antigen-binding molecule" includes antibodies and antigen-binding fragments of antibodies, including, e.g., bispecific antibodies.

The term "CD22," as used herein, refers to the human CD22 protein unless specified as being from a non-human species (e.g., "mouse CD22," "monkey CD22," etc.). The human CD22 protein has the amino acid sequence as set forth in accession number CAA42006. The sequence of recombinant human CD22 ecto (D20-R687) with a myc myc hexahistidine tag ("hexahistidine" disclosed as SEQ ID NO: 60) is shown in accession number NP_001762.2 and also as SEQ ID NO: 50. The hCD22 ectodomain (D20-R687).hFc, can also be purchased from R&D Systems, Catalog #1968-SL-050.

As used herein, "an antibody that binds CD22" or an "anti-CD22 antibody" includes antibodies and antigen-binding fragments thereof that may bind soluble CD22 and/or cell surface expressed CD22. Soluble CD22 includes natural CD22 proteins as well as recombinant CD22 protein variants such as, e.g., CD22 constructs, that lack a transmembrane domain or are otherwise unassociated with a cell membrane.

As used herein, the expression "anti-CD22 antibody" includes both monovalent antibodies with a single specificity, as well as bispecific antibodies comprising a first arm that binds CD22 and a second arm that binds a second (target) antigen, wherein the anti-CD22 arm comprises any of the HCVR/LCVR or CDR sequences as set forth in Table 1 herein. Examples of anti-CD22 bispecific antibodies are described elsewhere herein. The term "antigen-binding molecule" includes antibodies and antigen-binding fragments of antibodies, including, e.g., bispecific antibodies.

The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., CD28). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, $C_H1$, $C_H2$ and $C_H3$. Each light chain comprises a light chain variable region (abbreviated herein as LCVR or VL) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD28 antibody and/or anti-CD22 antibody (or antigen-binding portion thereof) may be identical to the human germ line sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—

$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$—$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) *Proc. Natl. Acad. Sci.* (*USA*) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-CD28 antibodies and/or anti-CD22 antibodies of the invention (monospecific or bispecific) are human antibodies. The term "human antibody", as used herein, is intended to include antibodies having variable and constant regions derived from human germ line immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germ line of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) *Molecular Immunology* 30:105) to levels typically observed using a human IgG1 hinge. The instant invention encompasses antibodies having one or more mutations in the hinge, CH2 or CH3 region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind CD28 and/or CD22. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 1.

The anti-CD28 antibodies and/or anti-CD22 antibodies herein, or the antigen-binding domains thereof, may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences disclosed herein to germline sequences available from, for example, public antibody sequence databases. The present invention includes antibodies, and the antigen-binding domains thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments, which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies, or the antigen-binding domains thereof, of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies, or the antigen-binding fragments thereof, that contain one or more germline mutations can be easily tested for one or more desired property such as, improved binding specificity, increased binding affinity, improved or enhanced antagonistic or agonistic biological properties (as the case may be), reduced immunogenicity, etc. Antibodies, or the antigen-binding fragments thereof, obtained in this general manner are encompassed within the present invention.

The present invention also includes anti-CD28 antibodies and/or anti-CD22 antibodies and antigen-binding molecules comprising variants of any of the HCVR, LCVR, and/or CDR amino acid sequences disclosed herein. Exemplary variants included within this aspect of the invention include variants of any of the HCVR, LCVR, and/or CDR amino acid sequences disclosed herein having one or more conservative substitutions. For example, the present invention includes anti-CD28 antibodies and antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 6 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol. Biol.* 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al (1992) *Science* 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402.

The terms "cell proliferative disorder" and "proliferative disorder" refer to disorders that are associated with some degree of abnormal cell proliferation that would benefit from treatment with anti-CD28/anti-CD22 bispecific antigen-binding molecules or method of the invention. This includes chronic and acute disorders including those pathological conditions which predispose the mammal to the disorder in question. In one embodiment, the cell proliferative disorder is cancer, the physiological condition in mammals that is typically characterized by unregulated cell growth/proliferation.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

A "B-cell proliferative disorder" includes Hodgkin's lymphoma, non-Hodgkin's lymphoma (NHL), such as aggressive NHL, relapsed aggressive NHL, low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, indolent NHL including relapsed indolent NHL and rituximab-refractory indolent NHL; refractory NHL, refractory indolent NHL, mantle cell lymphoma, AIDS-related lymphoma, and Waldenstrom's Macroglobulinemia, lymphocyte predominant Hodgkin's disease (LPHD), small lymphocytic lymphoma (SLL), chronic lymphocytic leukemia (CLL); leukemia, including acute lymphoblastic leukemia (ALL), chronic lymphocytic leukemia (CLL), Hairy cell leukemia, chronic myeloblastic leukemia; and other hematologic malignancies.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology (3rd edition), A. Victor Hoffbrand and John E. Pettit (eds.) (Harcourt Publishers Ltd., 2000). See, in particular, the lists in FIGS. 11.57, 11.58 and 11.59. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B cell lymphoma, splenic marginal zone lymphoma, extranodal marginal zone-MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The anti-CD28 antibodies and/or anti-CD22 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

Use of the expressions "anti-CD28 antibody" and/or "anti-CD-22 antibody" herein is intended to include both monospecific anti-CD28 antibodies and/or monospecific anti-CD22 antibodies as well as bispecific antibodies comprising a CD28-binding arm or CD22-binding arm and an arm that binds a target antigen. Thus, the present invention includes bispecific antibodies wherein one arm of an immunoglobulin binds human CD28 or CD22, and the other arm of the immunoglobulin is specific for a target antigen. The target antigen that the other arm of the CD28 or CD22 bispecific antibody binds can be any antigen expressed on or in the vicinity of a cell, tissue, organ, microorganism or virus, against which a targeted immune response is desired. The CD28-binding arm can comprise any of the HCVR/LCVR or CDR amino acid sequences as set forth in Table 1 herein. The CD22-binding arm can comprise any of the HCVR/LCVR or CDR amino acid sequences as set forth in Table 1 herein. In certain embodiments, the CD28-binding arm binds human CD28 and induces human T cell proliferation.

In the context of bispecific antibodies of the present invention wherein one arm of the antibody binds CD28 and the other arm binds a target antigen, the target antigen can be a tumor-associated antigen, such as CD22.

According to certain exemplary embodiments, the present invention includes bispecific antigen-binding molecules that specifically bind CD28 and CD22. Such molecules may be referred to herein as, e.g., "anti-CD28/anti-CD22," or "anti-CD28×CD22," or "CD28×CD22" or "anti-CD22/anti-CD28," or "anti-CD22×CD28," or "CD22×CD28" bispecific molecules, or "αCD22×αCD28", or "αCD28×αCD22", or other similar terminology.

According to certain exemplary embodiments, the bispecific antigen-binding molecules (e.g., bispecific antibody) may have an effector arm and a targeting arm. The effector arm may be the first antigen-binding domain (e.g., anti-CD28 antibody) that binds to the antigens on effector cells (e.g., T cells). The targeting arm may be the second antigen binding domain (e.g., anti-CD22 antibody) that binds to the antigens on target cells (e.g., tumor cells). According to certain exemplary embodiments, the effector arm binds to CD28 and the targeting arm binds to CD22. The bispecific anti-CD28/CD22 may provide co-stimulatory signal to effector cells (e.g., T cells). The effector arm has no effect to stimulate T cells without clustering. The effector arm alone has little effect to stimulate T cells unless in combination with the targeting arm. The tumor targeting arm may have imperfect tumor specificity. The antigen that is the target of the targeting arm (e.g., CD22) may be expressed on a fraction of tumor cells. The specificity of the tumor targeting arm may be increased by overlapping with combination with anti-CD3 bispecific antigen-binding molecules (e.g., anti-CD3/CD20 bispecific antibody).

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD28), and the second antigen-binding domain specifically binds a second, distinct antigen (e.g., CD22).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen binding domain (e.g., a bispecific antibody), the CDRs of the first antigen-binding domain may be designated with the prefix "D1" and the CDRs of the second antigen-binding domain may be designated with the prefix "D2". Thus, the CDRs of the first antigen-binding domain may be referred to herein as D1-HCDR1, D1-HCDR2, and D1-HCDR3; and the CDRs of the second antigen-binding domain may be referred to herein as D2-HCDR1, D2-HCDR2, and D2-HCDR3.

The first antigen-binding domain and the second antigen-binding domain may be directly or indirectly connected to one another to form a bispecific antigen-binding molecule of the present invention. Alternatively, the first antigen-binding domain and the second antigen binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residue. In other embodiments, the multimerizing domain is a cysteine residue, or a short cysteine containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (OVO)-Ig, Quadroma, knobs-into-holes, common light chain (e.g., common light chain with knobs-intoholes, etc.), CrossMab, CrossFab, (SEEO)body, leucine zipper, Ouobody, IgG1/IgG2, dual acting Fab (OAF)-IgG, and Mab² bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., LN/FIW or T), 254 (e.g., S or T), and 256 (e.g., S/R/Q/EID or T); or a modification at position 428 and/or 433 (e.g., UR/S/P/Q or K) and/or 434 (e.g., H/F or V); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252,254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second CH3 include: D16E, L 18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in WO2014/022540A1, the entire contents of which are incorporated herein by reference. Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germ line sequences available from, for example, public antibody sequence databases. The antigen-binding molecules of the present invention may comprise antigen binding fragments which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germ line sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germ line sequence while certain other residues that differ from the original germ line sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present invention also includes antigen-binding molecules comprising an antigen binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol. Biol.* 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402.

pH-Dependent Binding

The present invention includes anti-CD28/anti-CD22 bispecific antigen-binding molecules, with pH-dependent binding characteristics. For example, an anti-CD28 antibody of the present invention may exhibit reduced binding to CD28 at acidic pH as compared to neutral pH. Alternatively, anti-CD22 antibodies of the invention may exhibit enhanced binding to CD22 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD28 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-CD28/anti-CD22 bispecific antigen binding molecules are provided comprising an Fc domain comprising one or more mutations which enhance or diminish antibody binding to the FcRn receptor, e.g., at acidic pH as compared to neutral pH. For example, the present invention includes antibodies and antigen binding molecules comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-CD28/anti-CD22 bispecific antigen binding molecules comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Antigen-Binding Molecules

The present invention includes antibodies and antigen-binding fragments thereof that bind human CD28 and/or CD22 with high affinity. The present invention also includes antibodies and antigen binding fragments thereof that bind human CD28 and/or CD22 with medium or low affinity, depending on the therapeutic context and particular targeting properties that are desired. For example, in the context of a bispecific antigen-binding molecule, wherein one arm binds CD28 and another arm binds a target antigen (e.g., CD22), it may be desirable for the target antigen-binding arm to bind the target antigen with high affinity while the anti-CD28 arm binds CD28 with only moderate or low affinity. In this manner, preferential targeting of the antigen-binding molecule to cells expressing the target antigen may be achieved while avoiding general/untargeted CD28 binding and the consequent adverse side effects associated therewith.

According to certain embodiments, the present invention includes antibodies and antigen-binding fragments of antibodies that bind human CD22 (e.g., at 25° C.) with a $K_D$ of less than about 15 nM as measured by surface plasmon resonance, e.g., using an assay format as defined in Example 5 herein. In certain embodiments, the antibodies or antigen-binding fragments of the present invention bind human CD22 with a $K_D$ of less than about 15 nM, less than about 14 nM, less than about 13 nM, less than about 12 nM, less than about 11 nM, less than about 10 nM, less than about 9 nM, less than about 8 nM, less than about 7 nM, less than about 6 nM, less than about 5 nM, less than about 4 nM, less than about 3 nM, less than about 2 nM, or less than about 1 nM, as measured by surface plasmon resonance, e.g., using an assay format as defined in Example 5 herein, or a substantially similar assay.

According to certain embodiments, the present invention includes antibodies and antigen-binding fragments of antibodies that bind monkey CD22 (e.g., at 25° C.) with a $K_D$ of less than about 60 µM as measured by surface plasmon resonance, e.g., using an assay format as defined in Example 5 herein. In certain embodiments, the antibodies or antigen-binding fragments of the present invention bind monkey CD22 with a $K_D$ of less than about 60 µM, less than about 59 µM, less than about 58 µM, less than about 57 µM, less than about 56 µM, less than about 55 µM, less than about 54 µM, less than about 53 µM, less than about 52 µM, less than about 51 µM, less than about 50 µM, less than about 49 µM, less than about 48 µM, less than about 47 µM, less than about 46 µM, less than about 45 µM, less than about 44 µM, less than about 43 µM, less than about 42 µM, less than about 41 µM, less than about 40 µM, less than about 39 µM, less than about 38 µM, less than about 37 µM, less than about 36 µM, less than about 35 µM, less than about 34 µM, less than about 33 µM, less than about 32 µM, less than about 31 µM, less than about 30 µM, less than about 25 µM, less than about 20 µM, less than about 15 µM, or less than about 10 µM, as measured by surface plasmon resonance, e.g., using an assay format as defined in Example 5 herein, or a substantially similar assay.

According to certain embodiments, the present invention includes antibodies and antigen-binding fragments of antibodies that bind human CD28 (e.g., at 25° C.) with a $K_D$ of less than about 45 µM as measured by surface plasmon resonance, e.g., using an assay format as defined in Example 5 herein. In certain embodiments, the antibodies or antigen-binding fragments of the present invention bind human CD28 with a $K_D$ of less than about 45 µM, less than about 44 µM, less than about 43 µM, less than about 42 µM, less than about 41 µM, less than about 40 µM, less than about 39 µM, less than about 38 µM, less than about 37 µM, less than about 36 µM, less than about 35 µM, less than about 34 µM, less than about 33 µM, less than about 32 µM, less than about 31 µM, less than about 30 µM, less than about 25 µM, less than about 20 µM, less than about 15 µM, less than about 10 µM, as measured by surface plasmon resonance, e.g., using an assay format as defined in Example 5 herein, or a substantially similar assay.

The present invention also includes antibodies and antigen-binding fragments thereof that bind human CD22 with a dissociative half-life (t½) of greater than about 7.5 minutes as measured by surface plasmon resonance at 25° C., e.g., using an assay format as defined in Example 5 herein, or a substantially similar assay. In certain embodiments, the antibodies or antigen-binding fragments of the present invention bind human CD22 with a t½ of greater than about 7 minutes, greater than about 10 minutes, greater than about 15 minutes, greater than about 20 minutes, greater than about 25 minutes, greater than about 30 minutes, greater than about 35 minutes, greater than about 40 minutes, greater than about 45 minutes, greater than about 50 minutes, greater than about 55 minutes, greater than about 60 minutes, greater than about 65 minutes, greater than about 70 minutes, greater than about 75 minutes, or greater than about 100 minutes, as measured by surface plasmon resonance at 25° C., e.g., using an assay format as defined in Example 5 herein, or a substantially similar assay.

The present invention also includes antibodies and antigen-binding fragments thereof that bind monkey CD22 with a dissociative half-life (t½) of greater than about 4.3 minutes as measured by surface plasmon resonance at 37° C., e.g., using an assay format as defined in the examples herein, or a substantially similar assay. In certain embodiments, the antibodies or antigen-binding fragments of the present invention bind CD28 with a t½ of greater than about 4 minutes, greater than about 5 minutes, greater than about 6 minutes, greater than about 7 minutes, greater than about 8 minutes, greater than about 9 minutes, greater than about 10 minutes, greater than about 15 minutes, greater than about 20 minutes, greater than about 25 minutes, greater than about 30 minutes, greater than about 35 minutes, greater than about 40 minutes, greater than about 45 minutes, or greater than about 50 minutes, as measured by surface plasmon resonance at 25° C., e.g., using an assay format as defined in Example 5 herein, or a substantially similar assay.

The present invention also includes antibodies and antigen-binding fragments thereof that bind human CD28 with a dissociative half-life (t½) of greater than about 2.3 minutes as measured by surface plasmon resonance at 25° C., e.g., using an assay format as defined in Example 5 herein, or a substantially similar assay. In certain embodiments, the antibodies or antigen-binding fragments of the present invention bind CD28 with a t½ of greater than about 2 minutes, greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1200 minutes, as measured by surface plasmon resonance at 25° C. or 37° C., e.g., using an assay format as defined in the examples herein, or a substantially similar assay.

The present invention also includes bispecific antigen-binding molecules (e.g., bispecific antibodies) which are capable of binding to human CD28 and human and monkey CD22. According to certain embodiments, the bispecific antigen-binding molecules of the invention specifically interact with cells that express CD28 and/or CD22. The extent to which a bispecific antigen-binding molecule binds cells that express CD28 and/or CD22 can be assessed by fluorescence activated cell sorting (FACS), as illustrated in Example 6 herein. For example, the present invention includes bispecific antigen-binding molecules which specifically bind human cell lines or cynomolgus cells which express CD28 but not CD22 (e.g., T cells), and human cell lines or cynomolgus cells which express CD22 but not CD28 (e.g., B cells or Nalm6 cells). The present invention includes bispecific antigen-binding molecules which bind any of the aforementioned cells and cell lines with an $EC_{50}$ value of from about $1.3 \times 10^{-6}$ to about $2.3 \times 10^{-8}$ M, or less, as determined using a FACS assay as set forth in Example 6 or a substantially similar assay.

The present invention includes bispecific antigen-binding molecules (e.g., bispecific antibodies) which are capable of binding to human CD28 and/or human CD22. According to certain embodiments, the bispecific antigen-binding molecules of the invention specifically interact with cells that express CD28 and/or CD22. The extent to which a bispecific antigen-binding molecule binds cells that express CD28 and/or CD22 can be assessed by flow cytometry, as illustrated in Example 7 herein. For example, the present invention includes bispecific antigen-binding molecules which specifically bind human cells which express CD28 but not CD22 (e.g., T cells), and human cell lines which express CD22 but not CD28 (e.g., HEK293 cells transduced with human CD22 and Raji B cells genetically modified to delete CD80 and CD86). The present invention includes bispecific antigen-binding molecules which bind any of the aforementioned cells and cell lines with an $EC_{50}$ value of from about $1.14 \times 10^{-8}$ to about $9.76 \times 10^{-9}$ M, or less, as determined by flow cytometry as set forth in Example 7 or a substantially similar assay.

The present invention also provides anti-CD28/anti-CD22 bispecific antigen-binding molecules that induce or enhance the potency of CD20×CD3 T cell-mediated killing of tumor cells. For example, the present invention includes anti-CD28×CD22 antibodies that induce or increase the potency of CD20×CD3 T cell-mediated killing of tumor cells with an $EC_{50}$ of less than about $1.48 \times 10^{-10}$ M, as measured in an in vitro T cell-mediated tumor cell killing assay, e.g., using the assay format as defined in Example 8 herein (e.g., assessing the extent of Raji cell killing by human PBMCs in the presence of anti-CD20×CD3 and anti-CD28×CD22 antibodies), or a substantially similar assay. In certain embodiments, the antibodies or antigen-binding fragments of the present invention induce T cell-mediated tumor cell killing (e.g., PBMC mediated killing of Raji cells) with an $EC_{50}$ value of less than about 150 pM, less than about 100 pM, less than about 75 pM, less than about 50 pM, less than about 25 pM, less than about 10 pM, less than about 5.0 pM, less than about 4.0 pM, less than about 3.0 pM, less than about 2.5 pM, less than about 2.0 pM, or less than about 1.5 pM, as measured by an in vitro T cell mediated tumor cell killing assay, e.g., using the assay format as defined in Example 8 herein, or a substantially similar assay.

The present invention also includes anti-CD28/anti-CD22 bispecific antigen-binding molecules which exhibit one or more characteristics selected from the group consisting of: activating T-cells, inducing IL-2 release, inducing CD25+ up-regulation in human PBMCs; and increasing human T-cell mediated cytotoxicity on CD22 expressing cell lines (see, e.g., Example 9 herein). The present invention also includes anti-CD28/anti-CD22 bispecific antigen-binding molecules which enhance killing of tumor cells expressing CD22 when combined with a bispecific antibody that binds CD20 and CD3, such as, but not limited to, REGN1979. The present invention also includes anti-CD28/anti-CD22 bispecific antigen-binding molecules which enhance killing of tumor cells expressing CD22 when combined with an antibody that binds PD-1, such as, but not limited to, cemiplimab. (See Examples 10-15).

Epitope Mapping and Related Technologies

The epitope on CD28 or CD22 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD28 protein or a CD22 protein. Alternatively, the epitope may consist of a plurality of non-contiguous amino acids (or amino acid sequences) of CD28 or CD22. The antibodies of the invention may interact with amino acids contained within a CD28 monomer, or may interact with amino acids on two different CD28 chains of a CD28 dimer. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques that can be used to determine an epitope or binding domain of a particular antibody or antigen-binding domain include, e.g., routine crossblocking assay such as that described in *Antibodies*, Harlow and Lane (Cold Spring Harbor Press, Cold Spring Harb., N.Y.), point mutagenesis (e.g., alanine scanning mutagenesis, arginine scanning mutagenesis, etc.), peptide blots analysis (Reineke, 2004, *Methods Mol Biol* 248:443-463), protease protection, and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystal structure analysis can also be used to identify the amino acids within a polypeptide with which an antibody interacts.

The present invention further includes anti-CD28 and anti-CD22 antibodies that bind to the same epitope as any of the specific exemplary antibodies described herein (e.g. antibodies comprising any of the amino acid sequences as set forth in Table 6 herein).

According to certain embodiments, the present invention provides antibodies and antigen binding fragments of antibodies that bind an epitope on human CD22 comprising one or more amino acids of SEQ ID NO:57, SEQ ID NO:58, and/or SEQ ID NO:59 as determined by hydrogen/deuterium exchange detected by mass spectrometry as set forth in Examples 3 and 4.

Likewise, the present invention also includes anti-CD28 and/or anti-CD22 antibodies that compete for binding to CD28 and/or CD22 with any of the specific exemplary antibodies described herein (e.g. antibodies comprising any of the amino acid sequences as set forth in Table 6 herein).

The present invention also includes bispecific antigen-binding molecules comprising a first antigen-binding domain that specifically binds human CD28, and a second antigen binding fragment that specifically binds human CD22, wherein the first antigen-binding domain binds to the same epitope on CD28 as any of the specific exemplary CD28-specific antigen-binding domains described herein, and/or wherein the second antigen-binding domain binds to the same epitope on CD22 as any of the specific exemplary CD22-specific antigen-binding domains described herein.

Likewise, the present invention also includes bispecific antigen-binding molecules comprising a first antigen-binding domain that specifically binds human CD28, and a second antigen binding fragment that specifically binds human CD22, wherein the first antigen-binding domain competes for binding to CD28 with any of the specific exemplary CD28-specific antigen binding domains described herein, and/or wherein the second antigen-binding domain competes for binding to CD22 with any of the specific exemplary CD22-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD28 (or CD22) as a reference bispecific antigen-binding molecule of the present invention, the reference bispecific molecule is first allowed to bind to a CD28 protein (or CD22 protein). Next, the ability of a test antibody to bind to the CD28 (or CD22) molecule is assessed. If the test antibody is able to bind to CD28 (or CD22) following saturation binding with the reference bispecific antigen-binding molecule, it can be concluded that the test antibody binds to a different epitope of CD28 (or CD22) than the reference bispecific antigen-binding molecule. On the other hand, if the test antibody is not able to bind to the CD28 (or CD22) molecule following saturation binding with the reference bispecific antigen-binding molecule, then the test antibody may bind to the same epitope of CD28 (or CD22) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., *Cancer Res.* 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD28 protein (or CD22 protein) under saturating conditions followed by assessment of binding of the test antibody to the CD28 (or CD22) molecule. In a second orientation, the test antibody is allowed to bind to a CD28 (or CD22) molecule under saturating conditions followed by assessment of binding of the reference antigen-binding molecule to the CD28 (or CD22) molecule. If, in both orientations, only the first (saturating) antigen-binding molecule is capable of binding to the CD28 (or CD22) molecule, then it is concluded that the test antibody and the reference antigen-binding molecule compete for binding to CD28 (or CD22).

As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD28 and CD22), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD28 or CD22) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454, the entire contents of which are incorporated herein by reference, for a detailed discussion of such engineered mice and the use thereof to produce bispecific antigen-binding molecules).

Bioequivalents

The present invention encompasses antigen-binding molecules having amino acid sequences that vary from those of the described antibodies but that retain the ability to bind CD28 and/or CD22. Such variant molecules comprise one or more additions, deletions, or substitutions of amino acids when compared to parent sequence, but exhibit biological activity that is essentially equivalent to that of the described antigen binding molecules. Likewise, the antigen binding molecules-encoding DNA sequences of the present invention encompass sequences that comprise one or more additions, deletions, or substitutions of nucleotides when compared to the disclosed sequence, but that encode an antigen binding molecule that is essentially bioequivalent to the described antigen-binding molecules of the invention. Examples of such variant amino acid and DNA sequences are discussed above.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include the exemplary bispecific antigen-binding molecules set forth herein comprising amino acid changes which modify the glycosylation characteristics of the antibodies, e.g., mutations which eliminate or remove glycosylation.

Species Selectivity and Species Cross-Reactivity

The present invention, according to certain embodiments, provides antigen-binding molecules that bind to human CD28 but not to CD28 from other species. The present invention also provides antigen-binding molecules that bind to human CD22 but not to CD22 from other species. The present invention also includes antigen-binding molecules that bind to human CD28 and to CD28 from one or more non-human species; and/or antigen-binding molecules that bind to human CD22 and to CD22 from one or more non-human species.

According to certain exemplary embodiments of the invention, antigen-binding molecules are provide which bind to human CD28 and/or human CD22 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee CD28 and or CD22. For example, in a particular exemplary embodiment of the present invention, bispecific antigen-binding molecules are provided comprising a first antigen-binding domain that binds human CD28 and cynomolgous CD28, and a second antigen-binding domain that specifically binds human CD22.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see, for example, WO 05/103081, the entire contents of which are incorporated herein by reference).

Therapeutic Formulation and Administration

The present invention provides pharmaceutical compositions comprising the antigen binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, *CRC Crit. Ref. Biomed. Eng.* 14:201). In another embodiment, polymeric materials can be used; see, *Medical Applications of Controlled Release*, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-CD28 antibody or a bispecific antigen binding molecule that specifically binds CD28 and a target antigen (e.g., CD22). The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in CD22 activity or a depletion of CD22+ cells.

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-CD28/anti-CD22 bispecific antigen-binding molecules of the present invention may be used for the treatment, prevention and/or amelioration of any disease or disorder associated with or mediated by CD22 expression or activity or the proliferation of CD22+ cells. The mechanism of action by which the therapeutic methods of the invention are achieved include killing of the cells expressing CD22 in the presence of effector cells, for example, T cells. Cells expressing CD22 which can be inhibited or killed using the bispecific antigen-binding molecules of the invention include, for example, cancerous B cells.

The antigen-binding molecules of the present invention may be used to treat, e.g., primary and/or metastatic tumors arising in the blood, bone marrow, lymph nodes (e.g., thymus, spleen), colon, liver, lung, breast, renal cancer, central nervous system, and bladder cancer. According to certain exemplary embodiments, the bispecific antigen binding molecules of the present invention are used to treat a B cell proliferative disorder.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with CD22 expression (e.g., a B cell proliferative disorder) comprising administering one or more of the bispecific antigen-binding molecules described elsewhere herein to a subject after the subject has been shown to be non-responsive to other types of anti-cancer therapies. For example, the present invention includes methods for treating a B cell proliferative disorder comprising administering an anti-CD28/anti-CD22 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received the standard of care for patients suffering from cancer, e.g., a B cell proliferative disorder. In other aspects, a bispecific antigen-binding molecule of the invention (an anti-CD28/anti-CD22 bispecific antigen binding molecule) comprising an IgG4 Fc domain is initially administered to a subject at one or more time points (e.g., to provide robust initial depletion of prostate cancer cells), followed by administration of an equivalent bispecific antigen-binding molecule comprising a different IgG domain, such as an IgG1 Fc domain, at subsequent time points. It is envisioned that the anti-CD28/anti-CD22 antibodies of the invention may be used in conjunction with other bispecific antigen binding molecules, such as with an anti-CD20/anti-CD3 bispecific antibody. It is also envisioned that the bispecific antibodies of the invention will be used in conjunction with checkpoint inhibitors, for example, those that target PD-1 and CTLA-4, and other targets. It may be advantageous to combine two bispecific antibodies that target the same tumor antigen (e.g., CD22), but with one of the bispecifics targeting the CD3 on T cells and the other bispecific targeting a co-stimulator molecule like CD28. This combination may be used alone to enhance tumor cell killing, or may be used in combination with a checkpoint inhibitor.

Combination Therapies and Formulations

The present invention includes compositions and therapeutic formulations comprising any of the exemplary antibodies and bispecific antigen-binding molecules described herein in combination with one or more additional therapeutically active components, and methods of treatment comprising administering such combinations to subjects in need thereof.

Exemplary additional therapeutic agents that may be combined with or administered in combination with an antigen-binding molecule of the present invention include, e.g., chemotherapy, radiation therapy, checkpoint inhibitors that target PD-1 (e.g., an anti-PD-1 antibody such as pembrolizumab, nivolumab, or cemiplimab, see U.S. Pat. No. 9,987,500, HCVR/LCVR of SEQ ID NOs 162/170), CTLA-4, LAG3, TIM3, and others, costimulatory agonist bivalent antibodies that target molecules such as GITR, OX40, 4-1 BB, and others, CD3× bispecific antibodies (See for example U.S. Pat. No. 9,657,102 (REGN1979), WO2017/053856A1, WO2014/047231A1, WO2018/067331A1 and WO2018/058001A1), other antibodies that target CD22× CD3, CD22×CD28, or that target CD20×CD3 and other costimulatory CD28× bispecific antibodies.

Other agents that may be beneficially administered in combination with antibodies of the invention include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD28/anti-CD22 bispecific antigen-binding molecule as disclosed herein) may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1 R, B-raf, PDGFR-o, PDGFR-13, FOLH1, PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; $F(ab')_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy, or treatment with a biologic, including checkpoint inhibitors or other bispecific antibodies.

The present invention includes compositions and therapeutic formulations comprising any of the antigen-binding molecules described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-CD28 antibody or a bispecific antigen-binding molecule that specifically binds CD22 and CD28) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-CD28 antibody or a bispecific antigen-binding molecule that specifically binds CD22 and CD28). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In one embodiment, the antigen-binding molecule (e.g., a bispecific antigen-binding molecule that specifically binds CD22 and CD28) is administered to a subject as a weight-based dose. A "weight-based dose" (e.g., a dose in mg/kg) is a dose of the antibody or the antigen-binding fragment thereof or the bispecific antigen-binding molecule that will change depending on the subject's weight.

In another embodiment, an antibody or the antigen-binding fragment thereof or a bispecific antigen-binding molecule is administered to a subject as a fixed dose. A "fixed dose" (e.g., a dose in mg) means that one dose of the antibody or the antigen-binding fragment thereof or the bispecific antigen-binding molecule is used for all subjects regardless of any specific subject-related factors, such as weight. In one particular embodiment, a fixed dose of an antibody or the antigen-binding fragment thereof or a bispecific antigen-binding molecule of the invention is based on a predetermined weight or age.

In general, a suitable dose of the antigen binding molecule the invention can be in the range of about 0.001 to about 200.0 milligram per kilogram body weight of the recipient, generally in the range of about 1 to 50 mg per kilogram body weight. For example, the antibody or the antigen-binding fragment thereof or the bispecific antigen-binding molecule can be administered at about 0.1 mg/kg, about 0.2 mg/kg, about 0.5 mg/kg, about 1 mg/kg, about 1.5 mg/kg, about 2 mg/kg, about 3 mg/kg, about 5 mg/kg, about 10 mg/kg, about 15 mg/kg, about 20 mg/kg, about 25 mg/kg, about 30 mg/kg, about 40 mg/kg, about 50 mg/kg per single dose. Values and ranges intermediate to the recited values are also intended to be part of this invention.

In some embodiments, the antigen binding molecule of the invention is administered as a fixed dose of between about 25 mg to about 2500 mg. In some embodiments, the antigen binding molecule of the invention is administered as a fixed dose of about 25 mg, about 30 mg, about 50 mg, about 75 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, or about 2500 mg. Values and ranges intermediate to the recited values are also intended to be part of this invention.

Diagnostic Uses of the Antibodies

The bispecific antibodies of the present invention may also be used to detect and/or measure CD28 or CD22, or CD28-expressing or CD22-expressing cells in a sample, e.g., for diagnostic purposes. For example, an anti-Anti-CD28×anti-CD22 antibody, or fragment thereof, may be used to diagnose a condition or disease characterized by aberrant expression (e.g., over-expression, under-expression, lack of expression, etc.) of CD28 or CD22. Exemplary diagnostic assays for CD28 or CD22 may comprise, e.g., contacting a sample, obtained from a patient, with an antibody of the invention, wherein the antibody is labeled with a detectable label or reporter molecule. Alternatively, an unlabeled antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, betagalactosidase, horseradish peroxidase, or luciferase. Specific exemplary assays that can be used to detect or measure CD28 or CD22 in a sample include enzyme-linked immunosorbent assay (ELISA), radioimmunoassay (RIA), and fluorescence-activated cell sorting (FACS). Samples that can be used in CD28 or CD22 diagnostic assays according to the present invention include any tissue or fluid sample obtainable from a patient which contains detectable quantities of CD28 or CD22 protein, or fragments thereof, under normal or pathological conditions. Generally, levels of CD28 or CD22 in a particular sample obtained from a healthy patient (e.g., a patient not afflicted with a disease or condition associated with abnormal CD28 or CD22 levels or activity) will be measured to initially establish a baseline, or standard, level of CD28 or CD22. This baseline level of CD28 or CD22 can then be compared against the levels of CD28 or CD22 measured in samples obtained from individuals suspected of having a CD28 or CD22 related disease or condition.

EXAMPLES

The following examples are put forth so as to provide those of ordinary skill in the art with a complete disclosure and description of how to make and use the methods and compositions of the invention and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Construction of Anti-CD22×CD28 Antibodies

Generation of Anti-CD28 Antibodies

Anti-CD28 antibodies were obtained by immunizing a VELOCIMMUNE® mouse (i.e., an engineered mouse comprising DNA encoding human Immunoglobulin heavy and kappa light chain variable regions) with human CD28 protein fused to the Fc portion of mouse IgG2a, or with cells expressing CD28 or with DNA encoding CD28. The antibody immune response was monitored by a CD28-specific immunoassay. When a desired immune response was achieved splenocytes were harvested and fused with mouse myeloma cells to preserve their viability and form hybridoma cell lines. The hybridoma cell lines were screened and selected to identify cell lines that produce CD28-specific antibodies. Using this technique several anti-CD28 chimeric antibodies (i.e., antibodies possessing human variable domains and mouse constant domains) were obtained. In addition, several fully human anti-CD28 antibodies were isolated directly from antigen-positive B cells without fusion to myeloma cells, as described in US 2007/0280945A1.

Certain biological properties of the exemplary anti-CD28 antibodies generated in accordance with the methods of this Example are described in detail in the Examples set forth below.

Generation of Anti-CD22 Antibodies

Anti-CD22 antibodies were obtained by immunizing a genetically modified mouse (a VELOCIMMUNE® mouse, see above) with a human CD22 antigen (e.g., See hCD22 ecto (D20-R687).hFc, R&D Systems, Catalog #1968-SL-050; Accession #CAA42006 (See also, FIG. 3), or by immunizing an engineered mouse comprising DNA encoding human immunoglobulin heavy and kappa light chain variable regions with a human CD22 antigen.

Following immunization, splenocytes were harvested from each mouse and either (1) fused with mouse myeloma cells to preserve their viability and form hybridoma cells and screened for CD22 specificity, or (2) B-cell sorted (as described in US 2007/0280945A1) using a human CD22 fragment as the sorting reagent that binds and identifies reactive antibodies (antigen-positive B cells).

Chimeric antibodies to CD22 were initially isolated having a human variable region and a mouse constant region. The antibodies were characterized and selected for desirable characteristics, including affinity, selectivity, etc. If necessary, mouse constant regions were replaced with a desired human constant region, for example wild-type or modified IgG1 or IgG4 constant region, to generate a fully human anti-CD22 antibody. While the constant region selected may vary according to specific use, high affinity antigen-binding and target specificity characteristics reside in the variable region.

Generation of Bispecific Antibodies that Bind CD28 and CD22

Bispecific antibodies comprising an anti-CD22-specific binding domain and an anti-CD28-specific binding domain were constructed using standard methodologies, wherein the anti-CD22 antigen binding domain and the anti-CD28 antigen binding domain each comprise different, distinct HCVRs paired with a common LCVR. In some instances the bispecific antibodies were constructed utilizing a heavy chain from an anti-CD28 antibody, a heavy chain from an anti-CD22 antibody and a common light chain (See Table 1).

The bispecific antibodies created in accordance with the present Example comprise two separate antigen-binding domains (i.e., binding arms). The first antigen-binding domain comprises a heavy chain variable region derived from an anti-CD28 antibody ("CD28-VH"), and the second antigen-binding domain comprises a heavy chain variable region derived from an anti-CD22 antibody ("CD22-VH"). Both the anti-CD22 and the anti-CD28 share a common light chain. The CD28-VH/CD22-VH pairing creates antigen-binding domains that specifically recognize CD28 on T cells and CD22 on tumor cells.

Example 2: Heavy and Light Chain Variable Region Amino Acid and Nucleic Acid Sequences Table 1 sets forth the amino acid sequence identifiers of the heavy and light chain variable regions and CDRs of selected anti-CD22 antibodies of the invention. The corresponding nucleic acid sequence identifiers are set forth in Table 2.

TABLE 1

Amino Acid Sequence Identifiers of CD22 Antibodies

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb33037P2 | 2 | 4 | 6 | 8 | 10 | 12 | 14 | 16 |
| mAb33041P2 | 18 | 20 | 22 | 24 | 10 | 12 | 14 | 16 |

TABLE 2

Nucleic Acid Sequence Identifiers of CD22 Antibodies

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb33037P2 | 1 | 3 | 5 | 7 | 9 | 11 | 13 | 15 |
| mAb33041P2 | 17 | 19 | 21 | 23 | 9 | 11 | 13 | 15 |

Table 3 sets forth the amino acid sequence identifiers of the heavy and light chain variable regions (HCVR and LCVR), CDRs of selected anti-CD28 antibodies of the invention. The corresponding nucleic acid sequence identifiers are set forth in Table 4.

TABLE 3

Amino Acid Sequence Identifiers of CD28 Antibody

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb14226P2 | 26 | 28 | 30 | 32 | 10 | 12 | 14 | 16 |

TABLE 4

Nucleic Acid Sequence Identifiers of CD28 Antibody

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb14226P2 | 25 | 27 | 29 | 31 | 9 | 11 | 13 | 15 |

A summary of the component parts of the various anti-CD22×anti-CD28 bispecific antibodies constructed is set forth in Table 5. Tables 6 and 7 list the HCVR, LCVR, CDRs and heavy chain and light chain sequence identifiers of the bispecific antibodies.

TABLE 5

Summary of Component Parts of Anti-CD22 × Anti-CD28 Bispecific Antibodies

| Bispecific Antibody Identifier | Anti-CD22 Antigen-Binding Domain Heavy Chain Variable Region | Anti-CD28 Antigen-Binding Domain Heavy Chain Variable Region | Common Light Chain Variable Region |
|---|---|---|---|
| REGN5837 | mAb33037P2 | mAb14226P2 | ULC3-20 |
| REGN5838 | mAb33041P2 | mAb14226P2 | ULC3-20 |

Table 6 shows the amino acid sequence identifiers for the bispecific anti-CD22×anti-CD28 antibodies exemplified herein. The corresponding nucleic acid sequence identifiers are set forth in Table 7.

TABLE 6

Amino Acid Sequences of Anti-CD22 × Anti-CD28 Bispecific Antibodies

| Bispecific Antibody Identifier | Anti-CD28 First Antigen-Binding Domain (D1) | | | | Anti-CD22 Second Antigen-Binding Domain (D2) | | | | Common Light Chain Variable Region | | | |
|---|---|---|---|---|---|---|---|---|---|---|---|---|
| | D1-HCVR | D1-HCDR1 | D1-HCDR2 | D1-HCDR3 | D2-HCVR | D2-HCDR1 | D2-HCDR2 | D2-HCDR3 | LCVR | LCDR1 | LCDR2 | LCDR3 |
| REGN5837 | 26 | 28 | 30 | 32 | 2 | 4 | 6 | 8 | 10 | 12 | 14 | 16 |
| REGN5838 | 26 | 28 | 30 | 32 | 18 | 20 | 22 | 24 | 10 | 12 | 14 | 16 |

TABLE 7

Nucleic Acid Sequences of Anti-CD22 × Anti-CD28 Bispecific Antibodies

| Bispecific Antibody Identifier | Anti-CD28 First Antigen-Binding Domain (D1) | | | | Anti-CD22 Second Antigen-Binding Domain (D2) | | | | Common Light Chain Variable Region | | | |
|---|---|---|---|---|---|---|---|---|---|---|---|---|
| | D1-HCVR | D1-HCDR1 | D1-HCDR2 | D1-HCDR3 | D2-HCVR | D2-HCDR1 | D2-HCDR2 | D2-HCDR3 | LCVR | LCDR1 | LCDR2 | LCDR3 |
| REGN5837 | 25 | 27 | 29 | 31 | 1 | 3 | 5 | 7 | 9 | 11 | 13 | 15 |
| REGN5838 | 25 | 27 | 29 | 31 | 17 | 19 | 21 | 23 | 9 | 11 | 13 | 15 |

Example 3: Epitope Mapping of REGN5837 Binding to CD22 by Hydrogen Deuterium Exchange H/D exchange epitope mapping with mass spectrometry (HDX-MS) was performed to determine the amino acid residues of CD22 (recombinant human CD22, SEQ ID NO:50) interacting with H4sH33037P2 (See Table 1, HCVR/LCVR pair of SEQ ID NO: 2/10) (anti-hCD22 monoclonal antibody; parent anti-hCD22 antibody of REGN5837). A general description of the H/D exchange method is set forth in e.g., Ehring (1999) *Analytical Biochemistry* 267(2):252-259; and Engen and Smith (2001) *Anal. Chem.* 73:256A-265A.

The HDX-MS experiments were performed on an integrated HDX/MS platform, consisting of a Leaptec HDX PAL system for the deuterium labeling and quenching, a Waters Acquity M-Class (Auxiliary solvent manager) for the sample digestion and loading, a Waters Acquity M-Class (pBinary solvent manager) for the analytical gradient, and Thermo Q Exactive HF mass spectrometer for peptide mass measurement.

The labeling solution was prepared as PBS buffer in $D_2O$ at pD 7.0 (10 mM phosphate buffer, 140 mM NaCl, and 3 mM KCl, equivalent to pH 7.4 at 25° C.). For deuterium labeling, 11 µL of CD22.mmH (REGN5140 (SEQ ID NO:50), 56.7 µM) or CD22.mmH premixed with H4sH33037P2 (See above) in 1:0.6 molar ratio (Ag-Ab complex) was incubated at 20° C. with 44 µL $D_2O$ labeling solution for various time-points in duplicates (e.g., Undeuterated control=0 second; deuterium-labeled for 5 minutes and 10 minutes). The deuteration reaction was quenched by adding 55 µL of pre-chilled quench buffer (0.5 M TCEP-HCl, 8 M urea and 1% formic acid) to each sample for a 5-minute incubation at 20° C. The quenched sample was then injected into a Waters HDX Manager for online pepsin/protease XIII digestion. The digested peptides were separated by a C8 column (1.0 mm×50 mm, NovaBioassays) with a 13-minute gradient from 10%-32% B (mobile phase A: 0.5% formic acid in water, mobile phase B: 0.1% formic acid in acetonitrile). The eluted peptides were analyzed by Q Exactive HF mass spectrometry in LC-MS/MS or LC-MS mode.

The LC-MS/MS data of undeuterated CD22 sample were searched against a database including CD22 and its randomized sequence using Byonic search engine (Protein Metrics). The search parameters (in ELN) were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D) (see below).

Deuterium Uptake (D-uptake) = Average Mass (deuterated) − Average Mass (undeuterated)

Percentage of deuterium uptake (% D) = $\dfrac{D\text{-uptake for peptide at each time point} \times 100\%}{\text{Maximum } D\text{-uptake of the peptide}}$ (defined in ELN)

A total of 427 peptides from hCD22.mmH (SEQ ID NO: 50) were identified from both hCD22.mmH alone and hCD22.mmH in complex with H4sH33037P2 (HCVR/

LCVR pair of SEQ ID NOs: 2/10) samples, representing 92.0% sequence coverage of hCD22. Any peptide which exhibited a differential percent D-uptake value above 5% was defined as significantly protected Table 8). For hCD22.mmH, peptides corresponding to amino acids 481-505 (NVQYAPRDVRVRKIKPLSEIHSGNS; SEQ ID NO:57) and 523-537 (FWEKNGRLLGKESQLNF; SEQ ID NO:58) were significantly protected by H4sH33037P2.

mM KCl, equivalent to pH 7.4 at 25° C.). For deuterium labeling, 11 μL of CD22.mmH (REGN5140 (SEQ ID NO:50), 56.7 μM) or CD22.mmH premixed with H4sH33041P2 in 1:0.6 molar ratio (Ag-Ab complex) was incubated at 20° C. with 44 μL D$_2$O labeling solution for various time-points in duplicates (e.g., Undeuterated control=0 second; deuterium-labeled for 5 minutes and 10 minutes). The deuteration reaction was quenched by adding

TABLE 8

Selected CD22.mmH peptides with significant protection upon binding to H4sH33037P2

| | | 5 min | | | 10 min | | | |
|---|---|---|---|---|---|---|---|---|
| CD22 Residues | Charge (+) | REGN5140 Centroid MH$^+$ | REGN5140 + H4sH33037P2 Centroid MH$^+$ | ΔD | REGN5140 Centroid MH$^+$ | REGN5140 + H4sH33037P2 Centroid MH$^+$ | ΔD | Δ % D |
| 481-492 | 2 | 1477.27 | 1476.94 | −0.33 | 1477.51 | 1477.01 | −0.50 | −5.7 |
| 481-497 | 4 | 2059.98 | 2059.38 | −0.60 | 2060.24 | 2059.62 | −0.62 | −5.9 |
| 481-499 | 4 | 2277.09 | 2276.48 | −0.61 | 2277.33 | 2276.65 | −0.68 | −5.4 |
| 482-490 | 3 | 1108.33 | 1108.02 | −0.32 | 1108.46 | 1108.20 | −0.26 | −5.99 |
| 484-492 | 3 | 1136.43 | 1136.22 | −0.22 | 1136.56 | 1136.29 | −0.27 | −5.08 |
| 484-499 | 4 | 1935.26 | 1934.65 | −0.61 | 1935.40 | 1934.69 | −0.70 | −6.82 |
| 488-505 | 3 | 2043.24 | 2042.65 | −0.60 | 2043.42 | 2042.69 | −0.73 | −5.52 |
| 489-497 | 3 | 1113.62 | 1113.13 | −0.49 | 1113.71 | 1113.17 | −0.53 | −10.63 |
| 489-499 | 3 | 1330.85 | 1330.31 | −0.54 | 1330.93 | 1330.32 | −0.61 | −8.96 |
| 489-505 | 2 | 1927.04 | 1926.45 | −0.59 | 1927.17 | 1926.46 | −0.70 | −5.76 |
| 489-505 | 3 | 1928.14 | 1927.55 | −0.59 | 1928.26 | 1927.61 | −0.65 | −5.56 |
| 491-499 | 2 | 1074.18 | 1073.78 | −0.41 | 1074.19 | 1073.74 | −0.45 | −8.94 |
| 491-499 | 3 | 1075.28 | 1074.83 | −0.45 | 1075.31 | 1074.80 | −0.51 | −9.97 |
| 491-505 | 2 | 1671.53 | 1671.05 | −0.48 | 1671.59 | 1671.11 | −0.48 | −5.02 |
| 491-505 | 3 | 1672.53 | 1672.04 | −0.48 | 1672.59 | 1672.10 | −0.49 | −5.09 |
| 491-505 | 4 | 1673.57 | 1673.08 | −0.50 | 1673.64 | 1673.14 | −0.50 | −5.19 |
| 493-505 | 2 | 1415.81 | 1415.33 | −0.48 | 1415.87 | 1415.40 | −0.47 | −5.91 |
| 523-531 | 2 | 1167.25 | 1166.91 | −0.34 | 1167.40 | 1166.97 | −0.43 | −6.87 |
| 523-531 | 3 | 1168.23 | 1167.88 | −0.36 | 1168.41 | 1167.93 | −0.48 | −7.48 |
| 523-534 | 4 | 1484.62 | 1484.25 | −0.37 | 1484.68 | 1484.12 | −0.56 | −5.80 |
| 523-536 | 3 | 1699.57 | 1699.11 | −0.46 | 1699.77 | 1699.24 | −0.53 | −5.16 |
| 524-534 | 3 | 1336.24 | 1335.83 | −0.41 | 1336.31 | 1335.93 | −0.38 | −5.50 |
| 526-537 | 2 | 1348.48 | 1348.17 | −0.32 | 1348.76 | 1348.27 | −0.49 | −5.03 |
| 527-537 | 2 | 1220.04 | 1219.62 | −0.42 | 1220.31 | 1219.81 | −0.50 | −6.44 |
| 528-534 | 2 | 776.80 | 776.55 | −0.26 | 776.92 | 776.60 | −0.32 | −7.19 |
| 528-536 | 2 | 992.76 | 992.44 | −0.32 | 992.95 | 992.57 | −0.38 | −6.30 |
| 528-537 | 2 | 1105.90 | 1105.60 | −0.30 | 1106.06 | 1105.71 | −0.35 | −5.11 |
| 528-537 | 3 | 1106.65 | 1106.35 | −0.30 | 1106.83 | 1106.47 | −0.37 | −5.20 |

Example 4: Epitope Mapping of H4sH33041P2 Binding to CD22 by Hydrogen Deuterium Exchange H/D exchange epitope mapping with mass spectrometry (HDX-MS) was performed to determine the amino acid residues of CD22 (recombinant human CD22, SEQ ID NO:50) interacting with H4sH33041P2 (anti-hCD22 monoclonal antibody having a HCVR/LCVR pair of SEQ ID NOs: 18/10), the parent anti-hCD22 of REGN5838). A general description of the H/D exchange method is set forth in e.g., Ehring (1999) *Analytical Biochemistry* 267(2):252-259; and Engen and Smith (2001) *Anal. Chem.* 73:256A-265A.

The HDX-MS experiments were performed on an integrated HDX/MS platform, consisting of a Leaptec HDX PAL system for the deuterium labeling and quenching, a Waters Acquity M-Class (Auxiliary solvent manager) for the sample digestion and loading, a Waters Acquity M-Class (pBinary solvent manager) for the analytical gradient, and Thermo Q Exactive HF mass spectrometer for peptide mass measurement.

The labeling solution was prepared as PBS buffer in D$_2$O at pD 7.0 (10 mM phosphate buffer, 140 mM NaCl, and 3

55 μL of pre-chilled quench buffer (0.5 M TCEP-HCl, 8 M urea and 1% formic acid) to each sample for a 5-minute incubation at 20° C. The quenched sample was then injected into a Waters HDX Manager for online pepsin/protease XIII digestion. The digested peptides were separated by a C8 column (1.0 mm×50 mm, NovaBioassays) with a 13-minute gradient from 10%-32% B (mobile phase A: 0.5% formic acid in water, mobile phase B: 0.1% formic acid in acetonitrile). The eluted peptides were analyzed by Q Exactive HF mass spectrometry in LC-MS/MS or LC-MS mode.

The LC-MS/MS data of undeuterated CD22 sample were searched against a database including CD22 and its randomized sequence using Byonic search engine (Protein Metrics). The search parameters (in ELN) were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D) as set forth below.

Deuterium Uptake (D-uptake) = Average Mass (deuterated) − Average Mass (undeuterated)

Percentage of deuterium uptake (% D) = $\dfrac{D\text{-uptake for peptide at each time point} \times 100\%}{\text{Maximum }D\text{-uptake of the peptide (defined in }ELN)}$ A total of 454 peptides from hCD22.mmH (SEQ ID NO: 50) were identified from both hCD22.mmH alone and hCD22.mmH in complex with H4sH33041P2 samples, representing 90.5% sequence coverage of hCD22. Any peptide which exhibited a differential percent D-uptake value above 5% was defined as significantly protected. For hCD22.mmH, peptides corresponding to amino acids 246-277 (CEVSSSNPEYTTVSWLKDGTSLKKQNTFTLNL; SEQ ID NO:59) were significantly protected by H4sH33041P2. Table 9 provides the results from selected peptides with significant protection upon binding to H4sH33041P2.

TABLE 9

Selected CD22.mmH peptides with significant protection upon binding to H4sH33041P2

| CD22 Residues | Charge (+) | 5 min | | | 10 min | | | |
|---|---|---|---|---|---|---|---|---|
| | | REGN5140 Centroid MH$^+$ | REGN5140 + H4sH33041P2 Centroid MH$^+$ | ΔD | REGN5140 Centroid MH$^+$ | REGN5140 + H4sH33041P2 Centroid MH$^+$ | ΔD | Δ % D |
| 246-260 | 2 | 1695.69 | 1693.75 | −1.94 | 1695.81 | 1693.88 | −1.94 | −20.2 |
| 247-255 | 1 | 1014.95 | 1013.86 | −1.09 | 1015.09 | 1013.90 | −1.19 | −23.7 |
| 248-255 | 1 | 885.67 | 884.67 | −1.00 | 885.72 | 884.68 | −1.03 | −25.4 |
| 248-257 | 1 | 1088.87 | 1087.06 | −1.81 | 1088.95 | 1087.08 | −1.86 | −32.8 |
| 248-258 | 1 | 1188.86 | 1186.62 | −2.24 | 1188.80 | 1186.76 | −2.03 | −33.4 |
| 248-260 | 1 | 1462.34 | 1460.14 | −2.20 | 1462.56 | 1460.37 | −2.19 | −27.5 |
| 248-260 | 2 | 1462.38 | 1460.87 | −1.51 | 1462.50 | 1461.05 | −1.45 | −18.5 |
| 248-267 | 2 | 2179.41 | 2177.73 | −1.68 | 2179.48 | 2177.78 | −1.70 | −12.4 |
| 250-255 | 1 | 698.73 | 698.06 | −0.68 | 698.74 | 698.07 | −0.67 | −28.2 |
| 256-260 | 1 | 595.67 | 595.38 | −0.29 | 595.77 | 595.43 | −0.34 | −13.2 |
| 256-277 | 3 | 2506.39 | 2505.08 | −1.31 | 2506.57 | 2505.28 | −1.28 | −8.1 |
| 258-277 | 3 | 2303.55 | 2302.37 | −1.18 | 2303.70 | 2302.61 | −1.09 | −7.9 |
| 258-277 | 4 | 2304.39 | 2303.05 | −1.34 | 2304.54 | 2303.17 | −1.37 | −9.4 |
| 259-274 | 3 | 1863.23 | 1862.24 | −1.00 | 1863.34 | 1862.39 | −0.95 | −8.7 |
| 259-276 | 3 | 2090.99 | 2089.88 | −1.11 | 2091.03 | 2090.10 | −0.93 | −8.0 |
| 259-277 | 2 | 2202.69 | 2201.88 | −0.82 | 2202.82 | 2201.99 | −0.83 | −6.1 |
| 259-277 | 3 | 2204.00 | 2202.93 | −1.07 | 2204.07 | 2203.10 | −0.97 | −7.5 |
| 260-267 | 2 | 923.71 | 923.41 | −0.30 | 923.83 | 923.53 | −0.30 | −6.2 |
| 261-267 | 1 | 736.43 | 736.18 | −0.25 | 736.55 | 736.26 | −0.29 | −6.7 |
| 261-267 | 2 | 737.43 | 737.18 | −0.26 | 737.55 | 737.28 | −0.28 | −6.7 |
| 261-272 | 2 | 1339.48 | 1338.86 | −0.62 | 1339.58 | 1338.99 | −0.59 | −7.5 |
| 261-272 | 3 | 1340.56 | 1339.91 | −0.65 | 1340.66 | 1340.07 | −0.59 | −7.8 |
| 261-273 | 2 | 1487.02 | 1486.00 | −1.02 | 1487.11 | 1486.15 | −0.96 | −11.2 |
| 261-273 | 3 | 1488.10 | 1487.01 | −1.09 | 1488.13 | 1487.19 | −0.94 | −11.5 |
| 261-274 | 2 | 1588.74 | 1587.70 | −1.04 | 1588.85 | 1587.90 | −0.94 | −10.3 |
| 261-276 | 2 | 1816.39 | 1815.41 | −0.98 | 1816.48 | 1815.57 | −0.92 | −8.5 |
| 261-277 | 2 | 1929.27 | 1929.31 | −1.04 | 1928.23 | 1928.38 | −0.93 | −8.2 |
| 261-277 | 3 | 1930.39 | 1929.37 | −1.01 | 1930.45 | 1929.55 | −0.89 | −7.9 |
| 261-277 | 4 | 1931.34 | 1930.30 | −1.05 | 1931.40 | 1930.46 | −0.94 | −8.3 |
| 262-267 | 1 | 622.98 | 622.71 | −0.27 | 623.08 | 622.80 | −0.27 | −8.4 |
| 262-274 | 3 | 1475.17 | 1474.20 | −0.97 | 1475.28 | 1473.08 | −2.20 | −18.0 |
| 262-275 | 4 | 1590.80 | 1589.66 | −1.13 | 1590.89 | 1589.77 | −1.12 | −11.7 |
| 262-276 | 3 | 1704.03 | 1701.62 | −2.41 | 1704.09 | 1701.66 | −2.43 | −23.3 |
| 262-277 | 2 | 1816.39 | 1815.41 | −0.98 | 1816.48 | 1815.57 | −0.92 | −8.5 |
| 262-277 | 3 | 1817.40 | 1816.38 | −1.02 | 1817.50 | 1816.57 | −0.93 | −8.7 |
| 264-273 | 2 | 1129.77 | 1128.49 | −1.28 | 1129.74 | 1128.78 | −0.96 | −17.5 |
| 264-274 | 2 | 1231.69 | 1231.40 | −0.29 | 1231.77 | 1231.25 | −0.52 | −5.6 |
| 267-276 | 2 | 1212.11 | 1211.38 | −0.73 | 1212.10 | 1211.47 | −0.63 | −10.6 |
| 267-277 | 2 | 1325.86 | 1325.12 | −0.74 | 1325.83 | 1325.22 | −0.61 | −9.4 |
| 268-273 | 2 | 769.65 | 768.82 | −0.83 | 769.64 | 768.88 | −0.76 | −24.9 |
| 268-274 | 1 | 870.35 | 869.46 | −0.89 | 870.28 | 869.56 | −0.73 | −20.2 |
| 268-274 | 2 | 871.36 | 870.53 | −0.83 | 871.34 | 870.61 | −0.73 | −19.4 |
| 268-276 | 2 | 1099.07 | 1098.29 | −0.79 | 1099.07 | 1098.36 | −0.70 | −13.3 |
| 268-277 | 1 | 1211.10 | 1210.45 | −0.66 | 1211.10 | 1210.45 | −0.65 | −10.2 |
| 268-277 | 2 | 1212.11 | 1211.38 | −0.73 | 1212.10 | 1211.47 | −0.63 | −10.6 |
| 268-277 | 3 | 1212.84 | 1212.11 | −0.73 | 1212.81 | 1212.16 | −0.64 | −10.7 |

Example 5: Surface Plasmon Resonance Derived Binding Affinities and Kinetic Constants of CD22×CD28 Bispecific Antibodies Equilibrium dissociation constants ($K_D$ values) for hCD22.mmH (SEQ ID NO: 50) and mfCD22.mmH (SEQ ID NO: 51) binding to purified anti-CD22×CD28 bispecific mAb or anti-CD22 bivalent parental mAb (See Table 1, mAB33037P2; HCVR/LCVR: SEQ ID NOs: 2/10) and mAb33041P2; HCVR/LCVR: SEQ ID NOs: 18/10) were determined using a real-time surface plasmon resonance biosensor using a Biacore T-200 or Biacore 4000 instrument. The CM5 Biacore sensor surface was derivatized by amine coupling with a monoclonal mouse anti-human Fc antibody (REGN2567: HCVR/LCVR: SEQ ID NOs: 33/34) to capture purified anti-CD22×CD28 bispecific or anti-CD22 parental mAbs (See Table 1 and 2 for mAb33037P2 and mAb33041P2). This Biacore binding study was performed in a buffer composed of 0.01M HEPES pH 7.4, 0.15M NaCl, 3 mM EDTA, 0.05% v/v Surfactant P20 (HBS-EP running buffer). Different concentrations of hCD22 (SEQ ID NO: 50) and mfCD22 (SEQ ID NO: 51) with an C-terminal myc.myc hexahistidine tag ("hexahistidine" disclosed as SEQ ID NO: 60) prepared in HBS-EP running buffer (ranging from 90 nM to 3.33 or 0.37 nM, 3-fold dilutions) were injected over the mAb captured surface at a flow rate of 30 µL/minute. Association of CD22.mmH (SEQ ID NO: 50) to the captured monoclonal antibody was monitored for 5 minutes and the dissociation of CD22.mmH in HBS-EP running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$K_D(M)=k_d/k_a$, and $t½$ (min)=0.693/$k_d$/60

Binding kinetic parameters for human and cyno CD22 binding to purified mAbs at 25° C. are shown below in Tables 10-12.

Equilibrium dissociation constants ($K_D$ values) for hCD28.mmH (SEQ ID NO: 54) purified anti-CD22×CD28 bispecific mAb or anti-CD28 bivalent parental mAb (See Tables 3 and 4 for mAb14226P2) were determined using a real-time surface plasmon resonance biosensor using a Biacore T-200 instrument. The CM4 Biacore sensor surface was derivatized by amine coupling with a monoclonal mouse anti-human Fc antibody (REGN2567; HCVR/LCVR SEQ ID NOs: 33/34) to capture purified anti-CD22×CD28 bispecific or anti-CD28 parental mAb (See above). This Biacore binding study was performed in a buffer composed of 0.01M HEPES pH 7.4, 0.15M NaCl, 3 mM EDTA, 0.05% v/v Surfactant P20 (HBS-EP running buffer). Different concentrations of hCD28 with a C-terminal myc.myc hexahistidine tag ("hexahistidine" disclosed as SEQ ID NO: 60) prepared in HBS-EP running buffer (ranging from 600 nM to 2.47 nM, 3-fold dilutions) were injected over the mAb captured surface at a flow rate of 50 µL/minute. Association of CD28.mmH (SEQ ID NO: 54) to the captured monoclonal antibody was monitored for 5 minutes and the dissociation of CD28.mmH in HBS-EP running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$K_D(M)=k_d/k_a$, and $t½$ (min)=0.693/$k_d$/60

Binding kinetic parameters for human CD28 binding to purified mAbs at 25° C. are shown below in Table 13.

TABLE 10

Human CD22.mmH Binding Kinetics to anti-CD22 × CD28 bispecific mAb at 25° C.

| REGN#/ Ab PID # | Lot # | Common Name | mAb Capture (RU) | 90 nM hCD22.mmH Bind (RU) | ka (1/Ms) | kd (1/s) | KD (M) | t½ (min) |
|---|---|---|---|---|---|---|---|---|
| REGN5837 | REGN5837-L3 | CD22 × CD28 mAb | 379.1 ± 2.4 | 100.5 | 1.70E+05 | 1.49E−03 | 8.75E−09 | 7.8 |
| H4sH33037P2 | H4sH33037P2-L2 | CD22 mAb | 358.3 ± 2.0 | 192.6 | 1.95E+05 | 1.48E−03 | 7.60E−09 | 7.8 |
| REGN5838 | REGN5838-L4 | CD22 × CD28 mAb | 475.3 ± 5.3 | 26.7 | 2.11E+04 | 3.02E−04 | 1.43E−08 | 38.2 |
| H4sH33041P2 | H4sH33041P2-L2 | CD22 mAb | 581.7 ± 1.9 | 61.5 | 2.05E+04 | 1.93E−04 | 9.43E−09 | 59.8 |

TABLE 11

Monkey CD22.mmH (XP_005588899.1) Binding Kinetics to anti-CD22 × CD28 bispecific mAb at 25° C.

| REGN#/Ab PID # | Lot # | Common Name | mAb Capture (RU) | 90 nM REGN5280 Bind (RU) | ka (1/Ms) | kd (1/s) | KD (M) | t½ (min) |
|---|---|---|---|---|---|---|---|---|
| H4sH33037P2 | H4sH33037P2-L2 | CD22 mAb | 423.8 ± 3.6 | 112.8 | 6.55E+04 | 2.66E−03 | 4.06E−08 | 4.3 |
| H4sH33041P2 | H4sH33041P2-L2 | CD22 mAb | 500.9 ± 0.9 | 13.2 | 6.83E+03 | 2.91E−04 | 4.26E−08 | 39.8 |

TABLE 12

Monkey CD22.mmH (EHH59463.1) Binding kinetics to anti-CD22 × CD28 bispecific mAb at 25° C.

| REGN#/Ab PID # | Lot # | Common Name | mAb Capture (RU) | 84 nM REGN528 1 Bind (RU) | ka (1/Ms) | kd (1/s) | KD (M) | t½ (min) |
|---|---|---|---|---|---|---|---|---|
| H4sH33037P2 | H4sH33037P2-L2 | CD22 mAb | 426.4 ± 1.6 | 127.5 | 8.07E+04 | 2.87E−03 | 3.56E−08 | 4.0 |
| H4sH33041P2 | H4sH33041P2-L2 | CD22 mAb | 499.7 ± 3.5 | 10.9 | 6.59E+03 | 3.90E−04 | 5.92E−08 | 29.6 |

TABLE 13

Human CD28.mmH Binding Kinetics to anti-CD22 × CD28 bispecific mAbs at 25° C.

| REGN#/Ab PID # | Lot # | Common Name | mAb Capture (RU) | 600 nM hCD28.mmH Bind (RU) | ka (1/Ms) | kd (1/s) | KD (M) | t½ (min) |
|---|---|---|---|---|---|---|---|---|
| REGN5837 | REGN5837-L3 | CD22 × CD28 mAb | 1060.7 ± 7.0 | 72.9 | 1.39E+04 | 4.73E−03 | 3.41E−07 | 2.4 |
| REGN5838 | REGN5838-L4 | CD22 × CD28 mAb | 1289.2 ± 10.5 | 77.0 | 1.23E+04 | 4.96E−03 | 4.04E−07 | 2.3 |
| REGN5705 | REGN5705-L2 | CD28 mAb | 564.5 ± 5.2 | 88.4 | 1.31E+04 | 4.80E−03 | 3.65E−07 | 2.4 |

Example 6: Binding Specificity of Anti-CD28 and Anti-CD22×CD28 Bispecific Antibodies to Target Cell Lines (Nalm6), Effector Cell Lines (Jurkat), and Cynomolgus Monkey T and B Cells Using Flow Cytometry Flow cytometric analysis was utilized to determine binding of CD22×CD28 bispecific antibodies to human CD22 expressing Nalm6 cells and human CD28 expressing Jurkat cells and to cynomolgus monkey T (CD28+) and B (CD22+) cells. Briefly, 1×10$^5$ cells/well were incubated for 30 minutes at 4° C. with a serial dilution of CD22×CD28 bispecific antibodies or H4sH15260P (an isotype control human IgG4 antibody that binds a human antigen with no cross-reactivity to human or cynomolgus CD28 or CD22), ranging from 133 nM to 61 pM for Jurkat and Nalm6 cells. Cynomolgus monkey PBMCs were incubated with a single 67 nM concentration of antibody. After incubation, the cells were washed twice with cold PBS containing 1% filtered FBS and a PE-conjugated anti-human secondary antibody was added to the cells and incubated for an additional 30 minutes. An additional phenotyping antibody cocktail (anti-CD2, anti-CD20, anti-CD16, anti-CD14) was added to wells with cynomolgus monkey PBCMs. Wells containing no antibody or secondary only were used as a control.

After incubation with secondary antibody, cells were washed, re-suspended in 200 µL cold PBS containing 1% filtered FBS and analyzed by flow cytometry on a BD LSR_Fortessa. Cynomolgus monkey T cells were identified as CD2+/CD16− and B cells as CD20+. EC$_{50}$ values for FACS binding were calculated using 4-parameter non-linear regression analysis in Prism software.

Table 14 provides the binding data of CD22×CD28 bispecific antibodies to the surface of cell lines expressing CD22 as determined by flow cytometry. Table 14 also provides the binding data of CD22×CD28 bispecific antibodies to the surface of cell lines expressing human CD28 as determined by flow cytometry.

REGN5837 bound to Nalm6 cells EC$_{50}$ value of 1.3E−08M. REGN5838 bound to Nalm6 cells EC50 value of 1.8E−08M. The isotype control antibody did not exhibit any binding to cell lines expressing CD22.

REGN5837 bound to Jurkat cells EC$_{50}$ value of 2.1E−08M. REGN5838 bound to Jurkat cells EC$_{50}$ value of 2.3E−08M. The isotype control antibody did not exhibit any binding to cell lines expressing CD28.

Table 15 provides the binding of data of CD22×CD28 bispecific antibodies to the surface of Cynomolgus monkey (Cambodian origin) T and B cells as determined by flow cytometry.

REGN5837 bound B cells of 12 of 12 and T cells of 11 of 12 cynomolgus monkeys tested. Binding to CD20+ B cells ranged from 12.6-30.3-fold over secondary, with a median of 15.7 fold. Binding to CD2+/CD16− T cells ranged from 1.2-5.2-fold over secondary, with a median of 3.5-fold. Positive binding was defined as greater than 1.2 fold over secondary. REGN5838 bound B cells of 12 of 12 and T cells of 11 of 12 cynomolgus monkeys tested. Binding to CD20+ B cells ranged from 6.5-13.5-fold over secondary, with a median of 9.3 fold. Binding to CD2+/CD16− T cells ranged from 1.2-4.7-fold over secondary, with a median of 3.8-fold. Positive binding was defined as greater than 1.2-fold over secondary. The isotype control antibody did not exhibit any binding to cynomolgus T or B cells.

TABLE 14

Binding and fold binding results for flow cytometric experiments on engineered target and effector cells.

| Antibody PID | Jurkat FACS [M] | Jurkat FACS Fold | Nalm6 FACS [M] | Nalm6 FACS Fold |
|---|---|---|---|---|
| REGN5837 | 2.1E−08 | 198 | 1.3E−08 | 12.2 |
| REGN5838 | 2.3E−08 | 203 | 1.8E−08 | 11.7 |
| Isotype Control | No binding | 1 | No binding | 1 |

TABLE 15

Fold binding results for flow cytometric experiments on cynomolgus (Cambodian origin) T and B cells.

| | B cell binding (Fold over secondary) | | | T cell binding (Fold over secondary) | | |
|---|---|---|---|---|---|---|
| | REGN5837 | REGN5838 | Iso Control | REGN5837 | REGN5838 | Iso Control |
| Cyno 1 | 22.4 | 12.2 | 1.3 | 4.3 | 4.3 | 1.2 |
| Cyno 2 | 28 | 13.4 | 1.1 | 5.2 | 3.9 | 1.2 |
| Cyno 3 | 22.5 | 13.5 | 1 | 5.2 | 4.7 | 1 |
| Cyno 4 | 15.4 | 7.9 | 1 | 1.5 | 1.4 | 0.9 |
| Cyno 5 | 13.2 | 7.4 | 1 | 2.9 | 2.8 | 1.1 |
| Cyno 6 | 30.3 | 17 | 1 | 3.5 | 3.7 | 1.2 |
| Cyno 7 | 19.8 | 11.9 | 1 | 4.1 | 4 | 1 |
| Cyno 8 | 10.6 | 6.5 | 1.2 | 3.5 | 4 | 1.2 |
| Cyno 9 | 12.8 | 7.2 | 1.1 | 2.6 | 3 | 1.1 |
| Cyno 10 | 16 | 10.2 | 1.4 | 3.5 | 3.8 | 1.1 |
| Cyno 11 | 14.5 | 8.4 | 1.2 | 1.5 | 1.4 | 1 |
| Cyno 12 | 12.6 | 7.5 | 1 | 1.2 | 1.2 | 0.8 |
| Median | 15.7 | 9.3 | 1.05 | 3.5 | 3.75 | 1.1 |

Example 7: Binding Specificity of Anti-CD28 and Anti-CD22×CD28 Bispecific Antibodies to Human CD4+ T-Cells and Engineered Target Cells Using Flow Cytometry Flow cytometric analysis was used to investigate the binding of CD22×CD28 bispecific (REGN5837; REGN5838) and control antibodies to effector cells expressing human CD28 (human CD4+ T-cells) and target cells expressing human CD22 (HEK293/hCD20/hCD22 and Raji/CD80 and CD86 negative B-cells). HEK293/hCD20 cells were included as a negative cell line for CD28 and CD22.

Human CD4+ T-cells were isolated from human peripheral blood mononuclear cells (PBMCs) obtained from a healthy donor leukocyte packs. PBMC isolation was accomplished by density gradient centrifugation using 50 mL SepMate™ tubes following the manufacturer's recommended protocol. Briefly, 15 mL of Ficoll-Paque PLUS was layered into 50 mL SepMate tubes, followed by addition of 30 mL of leukocytes diluted 1:2 with D-PBS+2% FBS. Subsequent steps were followed according to SepMate manufacturer's protocol. CD4+ T-cells were subsequently isolated from PBMC's using human CD4 Microbead kits from Miltenyi Biotec following the manufacturer's instructions. Isolated CD4+ T-cells were frozen in FBS containing 10% DMSO at a concentration of 5×10$^6$ cells per vial.

Target cells, including a HEK293 cell line and human Raji B-cells, were prepared as follows.

A stable HEK293 cell line (ATCC, #CRL-1573) expressing human CD20 (amino acids M1 to P297 of accession number NP_068769.2) was transduced with human CD22 (amino acids M1 to A847 of accession number NP_001762.2). Human CD22 positive cells were isolated by fluorescence-activated cell sorting (FACS) and single cloned. The resulting clonal cell line (HEK293/hCD20/hCD22 clone E4) was maintained in DMEM+10%+P/S/G+NEAA supplemented with 500 µg/mL G418.

Human Raji B-cells (ATCC #CCL-86), which endogenously express CD20, CD22, Fc gamma receptors (FcγR), CD80 and CD86 on the cell surface were genetically modified by deleting CD80 and CD86 using the CRIPSR technology. CD80 and CD86 are known ligands for CD28. Engineered Raji/CD80 and CD86 negative cells were maintained in RPMI+10% FBS+penicillin+streptomycin+glutamine supplemented with HEPES and sodium pyruvate.

Cells were stained as follows.

Briefly, human CD4+ T-cells, HEK293/hCD20, HEK293/hCD20/hCD22 and Raji/CD80 and CD86 negative cells were resuspended in staining buffer containing D-PBS+2% FBS. Raji cells were incubated with mouse IgG (final concentration of 625 mg/mL) to block endogenous Fc Gamma receptors). Briefly, in a 96 well plate, 2×10$^5$ cells/well were incubated for 30-60 minutes at 4° C. with serial dilutions of antibodies, ranging from 6.1 pM to 100 nM. A negative control sample was included containing no antibody. Cells were washed once with cold staining buffer and incubated for 30-45 minutes with Allophycocyanin (APC) labeled anti-human secondary antibody. After incubation, cells were washed once with cold D-PBS buffer without FBS and incubated with LIVE/DEAD Fixable Green Dead Cell Stain (Invitrogen) according to manufacturer's instructions to discriminate between live and dead cells. Cells were then fixed in BD Cytofix Buffer according to manufacturer's instructions, washed, re-suspended in staining buffer, and analyzed by flow cytometry on an iQue Screener flow cytometer. For $EC_{50}$ determinations, geometric mean fluorescence intensity (MFI) values were analyzed using a four parameter logistic equation over a 9-point response curve using GraphPad Prism. Fold binding was calculated using the following equation:

$$\text{Fold binding} = \frac{\text{Maximum Geometric } MFI \text{ value within tested dose-range}}{\text{Geometric } MFI \text{ value of background } [0nM]}$$

The ability of CD22×CD28 bispecific antibodies to bind to human CD22 and CD28 was assessed on primary human CD4+ T-cells and engineered cells either overexpressing CD22 (HEK293/hCD20/hCD22) or endogenously (Raji/CD80 and CD86 negative) by flow cytometry. A negative cell line was included as a control (HEK293/hCD20).

$EC_{50}$/fold binding values are summarized in FIG. 1 and Table 16.

TABLE 16

EC$_{50}$ and Fold binding results for flow cytometric experiments on human CD4$^+$ T-cells and engineered target cells:

| Antibodies | HEK293/hCD20 | | HEK293/hCD20/hCD22 | | Raji/CD80 and CD86 negative | | Human CD4$^+$ T-cells | |
|---|---|---|---|---|---|---|---|---|
| | EC$_{50}$ [M] | Fold binding | EC$_{50}$ [M] | Fold binding | EC$_{50}$ [M] | Fold binding | EC$_{50}$ [M] | Fold binding |
| REGN5837 | ND | 1.07 | NC | 16.44 | 9.76E−09 | 38.35 | NC | 9.25 |
| REGN5838 | ND | 1.11 | 1.14E−08 | 34.90 | 1.49E−08 | 81.74 | NC | 10.63 |
| REGN5705 | ND | 1.11 | ND | 1.00 | ND | 1.04 | 4.13E−09 | 37.48 |
| One-arm CD28 control | ND | 1.05 | ND | 1.11 | ND | 1.07 | n/c | 10.97 |
| Isotype Control | NC | 1.82 | ND | 1.15 | ND | 1.08 | ND | 1.11 |

Abbreviations:
NC = not-calculable (denoted for curves in which the binding did not reach saturation);
ND = not determined
Table 16. Tabulated EC$_{50}$ and fold binding values of antibodies to human CD4$^+$ T-cells and engineered cell lines such as HEK293/hCD20, HEK293/hCD20/hCD22 or Raji/CD80 and CD86 negative B-cells.

As expected none of the CD28 antibodies, parental (REGN5705; HCVR/LCVR SEQ ID NOs: 35/36) or its bispecific formats (REGN5837, REGN5838 and one-armed CD28 control (SEQ ID NO: 48) bound to negative HEK293/hCD20 cells. A weak binding, approximately 1.8× at the highest concentration, was detected with the isotype control antibody due to non-specific binding (FIG. 1 and Table 16).

Binding of anti-CD22×anti-CD28 antibodies was observed on HEK293/hCD20/hCD22, (16.44× for REGN5837 and 34.9× for REGN5838 with an EC$_{50}$ of approximately 11.4 nM) and on Raji/CD80 and CD86 negative cells (38.35× for REGN5837 with an EC$_{50}$ of approximately 9.76 nM and 81.74× for REGN5838 with an EC$_{50}$ of approximately 14.9 nM). No significant binding was detected with the one-armed CD28 and isotype control (FIG. 1 and Table 16).

Binding of antibodies targeting human CD28 was detected on primary human CD4+ T-cells. Parental CD28 antibody, REGN5705, bound 37.48× with an EC$_{50}$ of approximately 4.13 nM over background, whereas the bispecific antibodies, REGN5837, REGN5838 and the one-armed control showed a binding of 9.25×, 10.63× and 10.97×, respectively. As expected, the isotype control did not bind to cells (FIG. 1 and Table 16).

Example 8: Anti-CD22×CD28 Bispecific Antibody Co-Stimulation Enhances Targeted Cytotoxicity, T Cell Activation, and Cytokine Release by Anti-CD20×CD3 Bispecific Antibodies CD22×CD28 enhancement of CD20×CD3 targeted killing was evaluated in a 96-hour cytotoxicity assay targeting Raji cells engineered to lack expression of CD80 and CD86 (Raji-80/86DKO). Briefly, human PBMCs were plated in supplemented RPMI media at 1×10$^6$ cells/mL and incubated overnight at 37° C. in order to enrich for lymphocytes by depleting adherent macrophages, dendritic cells, and some monocytes. The following day, Raji-80/86DKO cells were labeled with 1 uM of the fluorescent tracking dye CFDA-SE and the adherent cell-depleted naïve PBMC were labeled with 1 uM of the fluorescent tracking dye CellTrace Violet. Labeled target cells and PBMC (Effector/Target cell 10:1 ratio) were co-incubated a serial dilution of CD20×CD3 bispecific antibody, REGN1979, having one heavy chain arm comprised of SEQ ID NO: 42, the other heavy chain arm comprised of SEQ ID NO: 43 and the light chain of SEQ ID NO: 44), (concentration range: 5 nM to 0.64 pM) and a fixed concentration of CD22×CD28 costimulatory molecules REGN5837 or REGN5838, 1-arm control CD28 bispecific (REGN5678), or IgG4s isotype control (H4sH10154P3, an isotype control having an HCVR/LCVR pair of SEQ ID NOs: 37/38) at 2.5 ug/ml (16.7 nM) for 96 hours at 37° C. Cells were harvested from the plates and analyzed by FACS on a FACS BD LSRFortessa-X20. For FACS analysis, cells were stained with a Fixable Live/Dead Far Red reactive (Invitrogen) dye. 20,000 counting beads were added to each well immediately before FACS analysis and 10,000 beads were collected for each sample. For the assessment of specificity of killing, cells were gated on live CFDA-SE labeled populations. Percent of live population was recorded and used for the calculation of survival.

T cell activation was assessed by incubating cells with directly conjugated antibodies to CD2, CD4, CD8, and CD25. The percentage of CD8+ cells expressing CD25 was reported as the measure of T cell activation. Additionally, as T cells proliferate, CellTraceViolet is diluted, leading to lower MFI as measured by FACS. T cell proliferation was thus reported as a decrease in the MFI of CellTraceViolet on CD8+ T cells. EC$_{50}$ values for target Raji cells lacking CD80 and CD86 expression and binding were calculated using 4-parameter non-linear regression analysis in Prism software.

Supernatants from this assay were collected for analysis of cytokine levels. Concentrations of IL 17a, IFNγ, TNFα, IL-10, IL-6, IL-4, and IL-2 were analyzed using a Cytometric Bead Array (CBA) kit following the manufacturer's instructions. Cytokine levels were interpolated from the curves generated by the kit standards and reported as pg/mL. Maximum cytokine levels were calculated using 4-parameter non-linear regression analysis in Prism software.

The results of the assays to assess the ability of the anti-CD20×CD3 bispecific antibody REGN1979 (see above) to induce unstimulated human T cells to kill target cells expressing human CD20 and CD22 in combination with a costimulatory CD22×CD28 antibody or 1-arm CD28 or isotype control antibodies was tested.

REGN1979 activated and directed human T cells to deplete Raji cells lacking CD80 and CD86 expression in a dose-dependent manner. The addition of a fixed concentration of CD22×CD28 bispecific antibodies to REGN1979 enhanced the cytotoxic efficacy (EC$_{50}$) of REGN1979 3.5-

6.4-fold when compared to REGN1979 with 1-arm CD28 or isotype control antibodies (Table 17).

The observed target-cell lysis mediated by REGN1979 was associated with T cell activation and proliferation, as measured by CD25 upregulation on CD8+ cells or CellTrace violet dilution respectively. The addition of a fixed concentration of CD22×CD28 bispecific antibodies to REGN1979 enhanced the potency of REGN1979 induced T cell activation and proliferation 2.1 to 2.6 fold and 7.4-8.4 fold respectively when compared to REGN1979 with 1-arm CD28 or isotype control antibodies (Table 17).

REGN1979 induced the release of human cytokines. Cytokine released observed with REGN1979 in combination with CD22×CD28 bispecific antibodies was enhanced in the presence of a fixed concentration of a CD22×CD28 costimulatory molecules with a fixed concentration of 1-arm CD28 or isotype control antibodies (Table 18).

In summary, co-stimulation increased the potency of targeted cytotoxicity, T cell activation, and cytokine release when compared to what was observed with CD20×CD3 in combination with control antibodies.

LAG-3 (Lymphocyte-Activation Gene 3) or other molecules (Sharpe et al. 2002). The co-stimulatory molecule, CD28, is activated by its endogenous ligands, CD80 or CD86 expressed on APCs. CD28 potentiates cellular signals, such as pathways controlled by the NFκB transcription factor after TCR activation. The CD28 co-signal is important for effective T-cell activation such as T cell differentiation, proliferation, cytokine release and cell-death (Smeets et al. 2012).

Anti-CD22×CD28 bispecific antibodies were characterized in a luciferase-based reporter bioassay and an IL-2 functional assay using primary human CD4+ T-cells.

Luciferase Based Reporter Assay:

A T-cell/APC (antigen-presenting cell) luciferase-based reporter assay was developed to evaluate the effect of CD28 activation on NFκB activity upon engagement with anti-CD28×anti-CD22 bispecific antibodies.

Engineering of Reporter T-Cells:

A clonal reporter T cell line was engineered by transducing immortal human Jurkat T-cells (ATCC #TIB-152) with a NFκB-Luciferase (NFκB-Luc) lentivirus reporter (from Qiagen) as per the manufacturer's instructions. The clonal reporter line (Jurkat/NFκB-Luc clone 1C11) was maintained in RPMI+10% FBS+penicillin+streptomycin+glutamine supplemented with 1 µg/mL puromycin.

Engineering of APCs:

A stable HEK293 cell line (ATCC, #CRL-1573) expressing human CD20 (amino acids M1 to P297 of accession number NP_068769.2) was transduced with human CD22 (amino acids M1 to A847 of accession number NP_001762.2). Human CD22 positive cells were isolated by fluorescence-activated cell sorting (FACS) and single cloned. The resulting clonal cell line (HEK293/hCD20/hCD22 clone E4) was maintained in DMEM+10%+P/S/G+ NEAA supplemented with 500 µg/mL G418.

Human Raji B-cells (ATCC #CCL-86), which express endogenously CD20, CD22, Fc gamma receptors (FcγR), CD80 and CD86 on the cell surface were genetically modified by deleting CD80 and CD86 using the CRIPSR technology. CD80 and CD86 are known ligands for CD28. Engineered Raji/CD80 and CD86 negative cells were maintained in RPMI+10% FBS+penicillin+streptomycin+glutamine supplemented with HEPES and sodium pyruvate.

T-Cell/APC Stimulation:

In this experiment, engineered reporter T-cells were stimulated via two bispecific antibodies. The first stimulation is delivered by a T-cell activating bispecific antibody REGN2281, an anti-CD20×anti-CD3 antibody with one heavy chain arm comprised of SEQ ID NO: 39, one heavy chain arm comprised of SEQ ID NO: 40 and a light chain arm of SEQ ID NO: 41), targeting CD3 molecules on

TABLE 17

EC$_{50}$ values for cytotoxicity and T cell activation (average of 3 experiments)

| Antibody | Cell Kill | | T cell activation (CD8+/CD25+) | | T cell division (CellTrace MFI of CD8+ cells) | |
|---|---|---|---|---|---|---|
| | EC$_{50}$ [M] | Fold EC$_{50}$ compared to IgG4s | EC$_{50}$ [M] | Fold EC$_{50}$ compared to IgG4s | EC$_{50}$ [M] | Fold EC$_{50}$ compared to IgG4s |
| REGN5837 | 1.48E−10 | 3.5 | 1.58E−11 | 2.1 | 4.81E−12 | 7.4 |
| REGN5838 | 8.12E−11 | 6.4 | 1.28E−11 | 2.6 | 4.23E−12 | 8.4 |
| 1-arm CD28 | 6.37E−10 | 0.8 | 3.46E−11 | 1.0 | 3.03E−11 | 1.2 |
| IgG4s Iso | 5.22E−10 | 1.0 | 3.32E−11 | 1.0 | 3.55E−11 | 1.0 |

TABLE 18

| | Cytokine release (pg/ml) | | | |
|---|---|---|---|---|
| | REGN5837 | REGN5838 | 1-arm CD28 | IgG4s Iso |
| IL-4 | 46 | 50 | 33 | 29 |
| IL-6 | 907 | 810 | 248 | 283 |
| IL-2 | 531 | 270 | 36 | 39 |
| IL-10 | 1917 | 2555 | 739 | 375 |
| TNFa | 277 | 339 | 100 | 66 |
| IFNg | 1847 | 1956 | 267 | 160 |
| IL-17A | 154 | 172 | 41 | 35 |

Example 9: Bioassays for CD22 Bispecific Antibodies

T-cell activation is achieved by stimulating T-cell receptors (TCR) that recognize specific peptides presented by major histocompatibility complex class I or II (MHCI or MHCII) proteins on antigen-presenting cells (APC) (Goldrath et al. 1999). An activated TCR, in turn, initiates a cascade of signaling events which can be monitored by reporter genes driven by various transcription factors such as, activator-protein 1 (AP-1), Nuclear Factor of Activated T-cells (NFAT) or Nuclear factor kappa-light-chain-enhancer of activated B cells (NFκB). The T-cell response is then further refined via engagement of co-receptors expressed either constitutively or inducibly on T-cells, such as CD28, CTLA-4 (Cytotoxic T-Lymphocyte-Associated Protein 4), PD-1 (Programmed Cell Death Protein 1), engineered reporter T-cells and CD20 on HEK293 or on Raji/CD80 and CD86 negative B-cells. The first stimulation bypasses the need of activation of TCRs by their natural ligands, which are specific peptides displayed on MHC molecules. The second stimulation is driven by a CD28 bispecific antibody (i.e., an anti-CD28×anti-CD22 bispecific antibody). This antibody mimics the CD28 activation on T-cells by its ligands, CD80/CD86, expressed on APCs. It interacts with CD28 on T-cells and CD22 on HEK293 cells or on Raji/CD80 and CD86 negative B-cells and drives the activation of CD28 on engineered reporter T-cells. The simultaneous TCR and CD28 activation leads to enhanced transcriptional activity of NFκB, which increases the production of the reporter gene, luciferase.

Luciferase Assay Set Up:

RPMI1640 supplemented with 10% FBS and P/S/G was used as the assay medium to prepare cell suspensions and antibody dilutions for screening of anti-CD22×anti-CD28 bispecific antibodies.

A day prior to screening, engineered reporter T-cells were cultured to $0.5 \times 10^6$ cells/mL in cell culture media. 1:3 serially diluted anti-CD28×anti-CD22 bispecific antibodies and controls were tested in the presence of constant 200 pM REGN2281 (anti-CD20×anti-CD3, see above) or REGN1945 (an hIgG4 isotype control having an HCVR/LCVR pair of SEQ ID NOs: 45/46). The 10-point dilution ranged between 15 pM to 100 nM with the final dilution containing no CD28 antibodies.

Reagents were added in following order: 1) A fixed concentration of final 200 pM REGN2281 (anti-CD20×anti-CD3, see above) or REGN1945 (hIgG4 isotype control, see above) were added to each well in 96 well white flat bottom plates; 2) HEK293 cells re-suspended to $4 \times 10^5$ cells/mL (final cell concentration $1 \times 10^4$ cells/well) or Raji/CD80 and CD86 negative B-cells to $2 \times 10^6$ cells/mL (final cell concentration $5 \times 10^4$ cells/well) were added to corresponding plates; 3) Serially diluted antibodies were added to corresponding wells; 4) Overnight cultured reporter T-cells were re-suspended to $2 \times 10^6$/mL and added to plates with a final concentration $5 \times 10^4$ cells/well. Plates were incubated for 4-6 hours at 37° C./5% $CO_2$, before the addition of 100 µL ONE-Glo™ (Promega) reagent to lyse cells and detect luciferase activity. The emitted light was captured in relative light units (RLU) on a multi-label plate reader Envision (PerkinElmer). All serial dilutions were tested in duplicates.

The $EC_{50}$ values of the antibodies were determined by fitting the data to a four-parameter logistic equation over a 10-point dose-response curve using GraphPad Prism™ software. Fold induction was calculated using the following equation:

$$\text{Fold induction} = \frac{\text{Maximum Mean } RLU \text{ value within tested dose-range}}{\text{Mean } RLU \text{ value of background } [0nM]}$$

IL-2 Functional Assay Using Primary Human CD4+ T-Cells:

A primary CD4+ T-cell/APC functional assay was developed to evaluate the effect of CD28 activation on IL-2 production upon engagement with anti-CD22×anti-CD28 bispecific antibodies.

Human Primary CD4+ T-Cell Isolation:

Human peripheral blood mononuclear cells (PBMCs) were isolated from a healthy donor leukocyte packs. PBMC isolation was accomplished by density gradient centrifugation using 50 mL SepMate™ tubes following the manufacturer's recommended protocol. Briefly, 15 mL of Ficoll-Paque PLUS was layered into 50 mL SepMate tubes, followed by addition of 30 mL of leukocytes diluted 1:2 with D-PBS+2% FBS. Subsequent steps were followed according to SepMate manufacturer's protocol. CD4+ T-cells were subsequently isolated from PBMC's using human CD4 Microbead kits from Miltenyi Biotec following the manufacturer's instructions. Isolated CD4+ T-cells were frozen in FBS containing 10% DMSO at a concentration of $5 \times 10^6$ cells per vial.

IL-2 Release from Primary CD4+ T-Cells Treated with CD28 Antibodies:

In this assay, primary CD4+ T-cells are activated via the crosslinking of CD3 on their surface using anti-CD20×anti-CD3 bispecific antibody (REGN2281, see above) in combination with either HEK293 cells engineered to express human CD20 or with endogenous CD20-expressing Raji cells, where CD80 and CD86 have been silenced using CRISPR technology (Raji/CD80 and CD86 negative cells). Binding of the CD20 arm of REGN2281 to CD20 expressing cells drives the clustering of the CD3 receptor, providing the first signal necessary for T-cell stimulation. Importantly, in some instances co-culturing of primary leukocytes with genetically distinct cells leads to incompatibility of allogeneic determinants and results in T-cell activation. This can provide a sufficient primary stimulus in the absence of exogenous addition of anti-CD20×anti-CD3 bispecific antibody. Regardless of the primary stimulus, in order to detect quantifiable IL-2 release, co-stimulation, which can be provided by cross-linking CD28 molecules, is necessary. Here, a bispecific CD28 antibody (i.e., an anti-CD28×anti-CD22 bispecific antibody) interacts with CD28 on CD4+ T-cells and CD22 on HEK293/hCD20 or RAJI/CD80 and CD86 negative cells and drives the clustering-activation of CD28. The combined TCR and CD28 engagement leads to enhanced IL-2 production which is released into cell culture media. IL-2 is detected and quantified from the cell supernatant using a homogenous, no wash, AlphaLisa kit from PerkinElmer.

Previously isolated and frozen human CD4+ T-cells were thawed the day of the assay in stimulation media (X-VIVO 15 cell culture media supplemented with 10% FBS, HEPES, NaPyr, NEAA, and 0.01 mM BME containing 50 U/ml benzonase nuclease). Cells were centrifuged at 1200 rpm for 10 minutes, resuspended in stimulation media and plated into 96-well round bottom plates at a concentration of $1 \times 10^5$ cells/well. HEK293 cells engineered to express human CD20 alone or in combination with human CD22, were treated with 15 µg/mL of Mitomycin C in primary stimulation media at a concentration of $10 \times 10^6$ cells/mL. Raji/CD80 and CD86 negative cells were treated with 20 µg/mL of Mitomycin C in primary stimulation media at a concentration of $10 \times 10^6$ cells/mL. After incubation for 1 hour at 37° C., 5% $CO_2$, HEK293 and Raji cells were washed 3 times with D-PBS containing 2% FBS and added to the wells containing CD4+ T-cells at a final concentration of $1 \times 10^4$ cells per well HEK293 cells or $5 \times 10^4$ cells per well for Raji/CD80 and CD86 negative cells. Subsequently, 1:3 serially diluted Anti-CD28×anti-CD22 bispecific or control antibodies, ranging from 15 pM to 100 nM, were added to wells in the presence of 2 nM REGN2281 (anti-CD20×anti-CD3) or REGN1945 (a negative hIgG4 isotype control, see above). The final point of the 10-point dilution contained no CD28 antibody. After plates were incubated for 72 hours at 37° C., 5% $CO_2$ they were centrifuged to pellet the cells and 40 µL of media supernatant was collected. From this, 5 µL was tested in a human IL-2 AlphaLISA assay according to the manufacturer's protocol. The measurements were acquired on the multi-label plate reader Envision and raw RFU (Relative Flourescence Units) values plotted. All serial dilutions were tested in duplicate.

The $EC_{50}$ values of the antibodies were determined by fitting data to a four-parameter logistic equation over a 10-point dose-response curve using GraphPad Prism™ software. Fold induction was calculated using following equation:

$$\text{Fold induction} = \frac{\text{Maximum Mean } RFU \text{ value within tested dose-range}}{\text{Mean } RFU \text{ value of background } [0nM]}$$

Results Summary and Conclusions:
Luciferase Based Reporter Assay:

The ability of anti-CD22×anti-CD28 bispecific antibodies to provide co-stimulation through CD28 on T-cells in the absence or presence of CD22 target expression was assessed in a reporter cell-based bioassay using luciferase activity as a read-out.

Activation curves are shown in FIG. 2 (A and B), $EC_{50}$ and fold induction values are summarized in Table 19 and 20 for engineered reporter T-cells co-incubated with HEK293/hCD20 or HEK293/hCD20/hCD22 cells in addition to 200 pM constant REGN1945 (hIgG4 isotype control) or REGN2281 (anti-CD20×anti-CD3).

When reporter T-cells and HEK293 derived APCs were treated with 200 pM REGN1945, none of the CD28 bispecific antibodies showed an increase in luciferase activity in the absence of TCR stimulation, irrespective of the HEK293 line used in the assay. Increased luciferase activation was observed only for the parental CD28 antibody (REGN5705) with HEK293/hCD20 cells (2.18×) and HEK293/hCD20/hCD22 cells (2.05×). The one-armed CD28 and isotype control antibody did not give rise in luciferase response in this setting (Table 19 and FIG. 2).

When reporter T-cells and HEK293 derived APCs were treated with 200 pM REGN2281, both anti-CD22×anti-CD28 bispecific antibodies (REGN5837 and REGN5838) induced a strong luciferase activity with CD22 expressing HEK293 cells, indicated by increasing $EC_{50}$ and fold induction values. The one-armed CD28 control antibody and the parental CD28 antibody (REGN5705; see HCVR/LCVR SEQ ID NOs: 35/36) showed similar activities on both HEK293 lines. The isotype control antibody did not give rise to a luciferase response in this setting (Table 20 and FIG. 2).

When reporter T-cells and Raji/CD80 and CD86 negative were treated with 200 pM REGN1945, both anti-CD22×anti-CD28 bispecific antibodies (REGN5837 and REGN5838) and the parental CD28 antibody induced luciferase activity, while the one-armed CD28 control antibody and isotype control showed no activity (Table 19 and FIG. 2).

When reporter T-cells and Raji/CD80 and CD86 negative were treated with 200 pM REGN2281, all CD28 bispecific antibodies (REGN5837 and REGN5838) and the one-armed CD28 control antibody, including the parental CD28 antibody, induced luciferase activity. $EC_{50}$ values could be determined only for anti-CD22×anti-CD28 and the parental CD28 antibody but not for the one-armed CD28 control due to a failure to reach saturation levels. No activation was detected with the isotype control (Table 20 and FIG. 2).

IL-2 Functional Assay Using Primary Human CD4+ T-Cells:

The ability of anti-CD22×anti-CD28 bispecific antibodies to provide co-stimulation through CD28 on T-cells in the absence or presence of CD22 target expression was assessed in a functional primary CD4+ T-cell assay measuring IL-2 cytokine production.

Figure 3A:
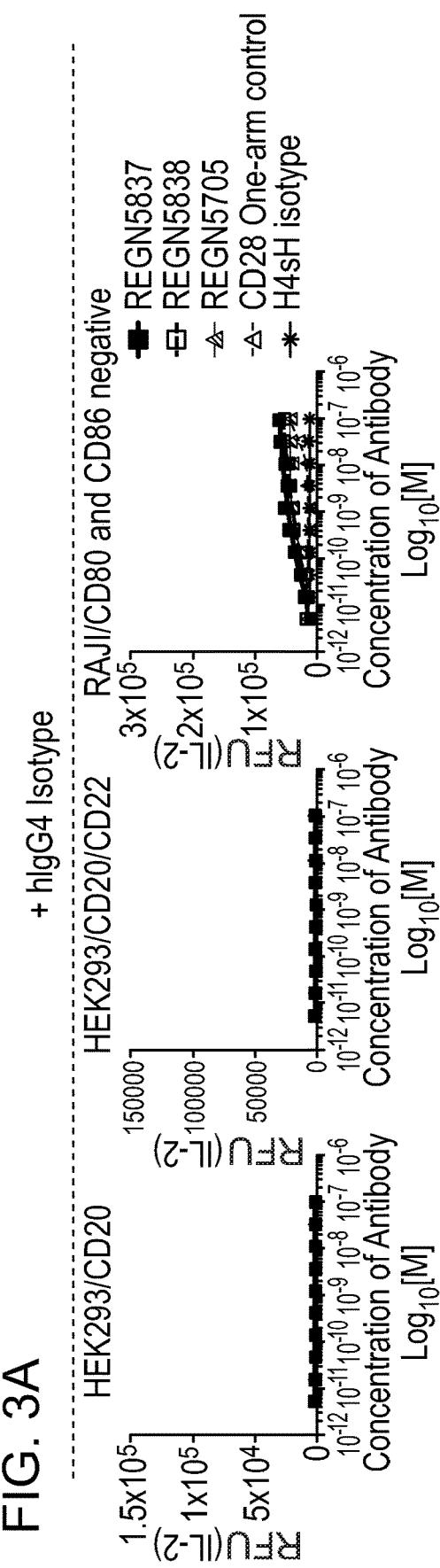
FIGS. 3A and 3B are a set of graphs depicting that anti-CD28/anti-CD22 bispecific antibodies increase IL-2 production in the presence of primary T-cell stimulation and CD22 target expression. More specifically.
Figure 3B:
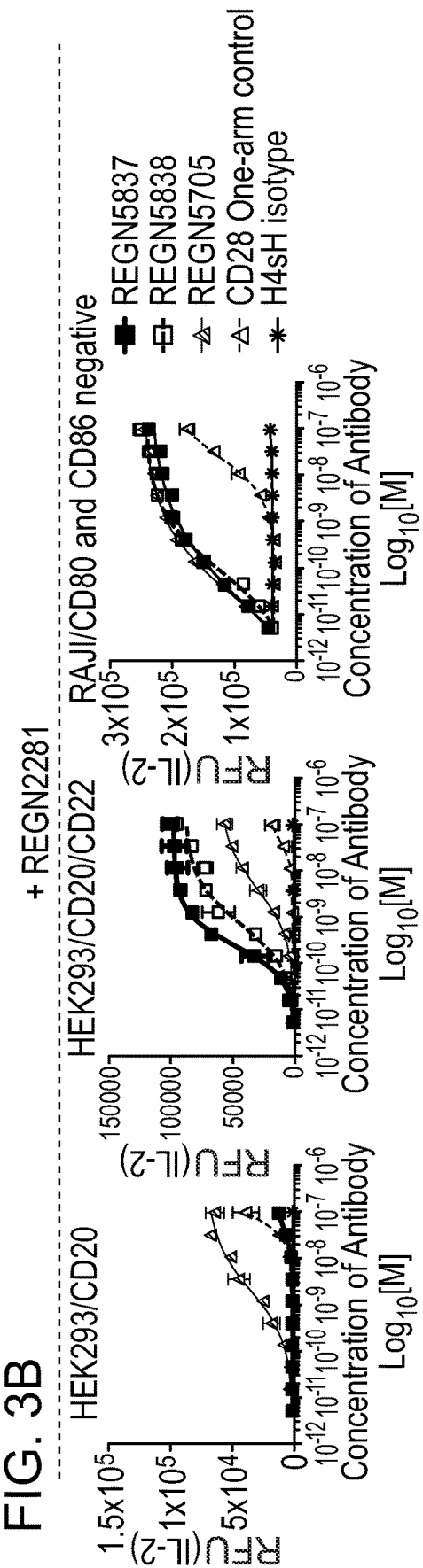

Activation curves are shown in FIG. 3 (A and B), $EC_{50}$ and fold induction values are summarized in Table 21 for CD4+ T-cells co-incubated with HEK293/hCD20, HEK293/hCD20/hCD22, or Raji/CD80 and CD86 negative cells in the presence of either 2 nM constant REGN1945 (hIgG4 isotype control) or REGN2281 (anti-CD20×anti-CD3).

No measurable IL-2 release was observed in wells containing HEK293/hCD20 or HEK293/hCD20/CD22 cells with constant amounts of REGN1945, due to the absence of sufficient allogeneic primary T-cell stimulation (FIG. 3). IL-2 release was, however, detected in wells containing Raji/CD80 and CD86 negative cells with constant amounts of REGN1945, due to a significant allogeneic response providing sufficient primary stimulus, even in the absence of antibody-mediated CD3 clustering (FIG. 3 and Table 21).

Measurable IL-2 levels were detected in samples containing HEK293/hCD20 or HEK293/hCD20/CD22 cells when a constant 2 nM concentration of REGN2281 and parental CD28 mab (REGN5705, see above) was added. In contrast to the bivalent CD28 mAb, IL2 release was not dramatically enhanced when anti-CD22×anti-CD28 bispecific mAbs are added to wells containing HEK293/hCD20 cells and REGN2281. It was only in the presence of HEK293/hCD20/CD22 cells and REGN2281 that anti-CD22×anti-CD28 bispecific mAbs significantly enhance IL-2 release (FIG. 3 and Table 22).

Tables 19-22 are set forth, below.

Table 19 presents the tabulated $EC_{50}$, maximum and fold induction values of luciferase activity in engineered T-cells co-incubated with HEK293/hCD20, HEK293/hCD20/hCD22 or RAJI/CD80 and CD86 negative cells and 200 pM constant REGN1945 (isotype control).

Table 20 presents the tabulated $EC_{50}$, maximum and fold induction values of luciferase activity in engineered T-cells co-incubated with HEK293/hCD20, HEK293/hCD20/hCD22 or Raji/CD80 and CD86 negative cells and 200 pM constant REGN2281 (anti-CD20×anti-CD3).

Table 21 presents the tabulated $EC_{50}$, maximum and fold induction values of IL-2 release from CD4+ T-cells co-incubated with HEK293/hCD20, HEK293/hCD20/hCD22, or RAJI/CD80 and CD86 negative cells and 2 nM constant REGN1945 (isotype control).

Table 22. Presents the tabulated $EC_{50}$, maximum and fold induction values of IL-2 release from CD4+ T-cells co-incubated with HEK293/hCD20, HEK293/hCD20/hCD22, or Raji/CD80 and CD86 negative cells and 2 nM constant REGN2281 (anti-CD20×anti-CD3).

TABLE 19

$EC_{50}$, Maximum and Fold induction values of luciferase activity in engineered reporter T-cells in absence of TCR stimulation with 200 pM REGN1945 (isotype control):

| Antibodies | HEK293/hCD20 | | | HEK293/hCD20/hCD22 | | | Raji/CD80 and CD86 negative | | |
|---|---|---|---|---|---|---|---|---|---|
| | $EC_{50}$ [M] | Fold induction | Max RLU | $EC_{50}$ [M] | Fold induction | Max RLU | $EC_{50}$ [M] | Fold induction | Max RLU |
| REGN5837 | ND | 1.01 | 11860 | ND | 1.11 | 13280 | 1.66E−09 | 1.29 | 16020 |
| REGN5838 | ND | 1.04 | 11980 | ND | 1.05 | 12480 | 2.55E−09 | 2.06 | 26500 |
| REGN5705 | 6.23E−09 | 2.18 | 24980 | 8.45E−09 | 2.05 | 25060 | 7.88E−09 | 2.57 | 33180 |
| One-arm CD28 | ND | 1.00 | 11700 | ND | 1.05 | 12880 | ND | 1.05 | 13720 |
| Isotype Control | ND | 1.04 | 11180 | ND | 1.04 | 12160 | ND | 1.04 | 12540 |

Abbreviations:
ND = not determined

TABLE 20

$EC_{50}$, Maximum and Fold induction values of luciferase activity in engineered reporter T-cells in presence of TCR stimulation with 200 pM REGN2281 ($\alpha$CD20 × $\alpha$CD3):

| Antibodies | HEK293/hCD20 | | | HEK293/hCD20/hCD22 | | | Raji/CD80 and CD86 negative | | |
|---|---|---|---|---|---|---|---|---|---|
| | $EC_{50}$ [M] | Fold induction | Max RLU | $EC_{50}$ [M] | Fold induction | Max RLU | $EC_{50}$ [M] | Fold induction | Max RLU |
| REGN5837 | NC | 1.40 | 250140 | 6.44E−10 | 8.46 | 799220 | 1.43E−09 | 4.46 | 754820 |
| REGN5838 | NC | 1.65 | 256380 | 1.89E−09 | 4.53 | 398720 | 1.33E−09 | 11.02 | 1725640 |
| REGN5705 | 2.63E−10 | 3.55 | 408680 | 7.7E−11 | 2.06 | 171300 | 4.33E−10 | 4.15 | 568740 |
| One-arm CD28 | NC | 3.56 | 454560 | 1.29E−08 | 2.82 | 228840 | NC | 4.46 | 642220 |
| Isotype Control | ND | 1.09 | 212580 | ND | 1.08 | 103940 | ND | 1.05 | 175540 |

Abbreviations:
NC = not-calculable (denoted for curves in which the response did not reach saturation); ND = not determined.

TABLE 21

$EC_{50}$, Maximum and Fold induction values of IL-2 release from primary human CD4+ Tells in presence of 2 nM REGN1945 (Isotype Control).

| Antibodies | HEK293/hCD20 | | | HEK293/hCD20/hCD22 | | | Raji/CD80 and CD86 negative | | |
|---|---|---|---|---|---|---|---|---|---|
| | $EC_{50}$ [M] | Fold induction | Max RFU | $EC_{50}$ [M] | Fold induction | Max RFU | $EC_{50}$ [M] | Fold induction | Max RFU |
| REGN5837 | ND | 1.07 | 2.01E+03 | ND | 1.00 | 1.74E+03 | 6.31E−11 | 5.07 | 6.18E+04 |
| REGN5838 | ND | 1.24 | 2.22E+03 | ND | 1.00 | 1.89E+03 | 4.23E−10 | 3.05 | 5.38E+04 |
| REGN5705 | ND | 1.11 | 2.29E+03 | ND | 1.71 | 2.95E+03 | 1.11E−10 | 3.56 | 4.95E+04 |
| One-arm CD28 | ND | 1.32 | 1.76E+03 | ND | 1.91 | 2.27E+03 | NC | 2.43 | 4.35E+04 |
| Isotype Control | ND | 1.19 | 2.29E+03 | ND | 1.47 | 1.87E+03 | ND | 1.00 | 1.51E+04 |

Abbreviations:
NC = not-calculable (denoted for curves in which the response did not reach saturation); ND = not determined.

TABLE 22

$EC_{50}$, Maximum and Fold induction values of IL-2 release from primary human CD4+ T-cells in presence of 2 nM REGN2281 ($\alpha$CD20 × $\alpha$CD3).

| Antibodies | HEK293/hCD20 | | | HEK293/hCD20/hCD22 | | | Raji/CD80 and CD86 negative | | |
|---|---|---|---|---|---|---|---|---|---|
| | EC50 [M] | Fold induction | Max RFU | EC50 [M] | Fold induction | Max RFU | EC50 [M] | Fold induction | Max RFU |
| REGN5837 | NC | 4.68 | 1.21E+04 | 2.35E−10 | 55.61 | 1.01E+05 | 4.66E−11 | 5.11 | 2.40E+05 |
| REGN5838 | NC | 6.82 | 1.31E+04 | 6.85E−10 | 53.73 | 9.63E+04 | 8.93E−11 | 6.32 | 2.54E+05 |
| REGN5705 | 2.23E−09 | 30.80 | 6.89E+04 | 4.07E−09 | 32.24 | 5.74E+04 | 4.51E−11 | 6.15 | 2.49E+05 |
| One-arm CD28 | NC | 19.45 | 3.99E+04 | NC | 6.85 | 1.89E+04 | NC | 4.45 | 1.79E+05 |

TABLE 22-continued

EC$_{50}$, Maximum and Fold induction values of IL-2 release from primary human CD4$^+$ T-cells in presence of 2 nM REGN2281 (αCD20 × αCD3).

| Antibodies | HEK293/hCD20 | | | HEK293/hCD20/hCD22 | | | Raji/CD80 and CD86 negative | | |
|---|---|---|---|---|---|---|---|---|---|
| | EC50 [M] | Fold induction | Max RFU | EC50 [M] | Fold induction | Max RFU | EC50 [M] | Fold induction | Max RFU |
| Isotype Control | ND | 1.22 | 2.22E+03 | ND | 1.00 | 3.20E+03 | ND | 1.00 | 4.54E+04 |

Abbreviations:
NC = not-calculable (denoted for curves in which the response did not reach saturation); ND = not determined.

Example 10: The Effect of a Combination of Anti-CD22×Anti-CD28 Antibody Plus Cemiplimab on IL-2 Release from Cells Engineered to Express PD-L1

Materials and Methods
Engineering of APCs:
RAJI Cells

RAJI is a B-lymphocyte cell line isolated from an 11-year old male in (ATCC® CCL-86™). RAJI are maintained in RPMI+10% FBS+P/S/G+NaPyr+HEPES.
RAJI CD80 and CD86 Negative Expression of CD80 and CD86 in RAJI cells were eliminated using CRISPR/Cas9 system.
NALM6 Clone G5

NALM6 clone is an acute lymphoblastic leukemia (ALL) cell line isolated from a 19-year old male in [NALM6 clone G5 (ATCC, #CRL-3273)]. NALM6 cells are maintained in RPMI+10% FBS+P/S/G.
WSU-DLCL2

WSU-DLCL2 is a human DLBCL cell line isolated from the pleural effusion of a 41-year-old Caucasian male (Leibnitz Institute-DSMZ, Cat. #ACC 575).
PD-L1 Engineered Cell Lines NALM-6, RAJI CD80 and CD86 negative (RAJI/CD80–CD86–), and WSU-DLCL2 cell lines were genetically engineered to stably express human PD-L1 (amino acids M1-T290 of accession number NP_054862.1). The resulting cell lines NALM6/PD-L1, RAJI/CD80–CD86–/PD-L1, and WSU-DLCL2/PD-L1 were maintained in their respective media, supplemented with 0.5 µg/mL puromycin for RAJI/CD80–CD86–, and 1 µg/mL puromycin for NALM-6/PD-L1 and WSU-DLCL2/PD-L1 cells.
T-Cell Activation Assays for T-Cell Proliferation and IL-2 Release The effect of REGN5837 on IL-2 release was assessed using human primary T cells and allogeneic human B-cell lymphoma cell lines [NALM-6, NALM-6/PD-L1, RAJI/CD80–CD86–, RAJI/CD80–CD86–/PD-L1, WSU-DLCL2, WSU-DLCL2/PD-L1]) in the presence of a fixed concentration of cemiplimab. Co-culturing of primary leukocytes with genetically distinct cells leads to incompatibility of allogeneic determinants and can result in T-cell activation. For assays using NALM-6 and RAJI/CD80–CD86– (+/− PD-L1) cells, T-cell activation assays were performed with enriched human primary T cells from 3 donors, while assays utilizing WSU-DLCL2 (+/−PD-L1) cells used T-cells from 1 donor.
Isolation of T-Cells Used in T-Cell Activation Assays for Testing REGN5837+REGN2810 Combination Treatment.

For experiments utilizing NALM-6 and RAJI/CD80–CD86– cells CD3+ T-cells were isolated from 3 donor PBMC's (555109, 555130, and 555131), while PBMC's from one donor (555175) were used for assays with WSU-DLCL2 cells. For Donor 555109, PBMC's were isolated from peripheral blood using density gradient centrifugation. Briefly, 15 ml of Ficoll-Paque PLUS is added to 50 ml conical tubes, and subsequently 30 ml of blood diluted 1:1 with PBS containing 2% FBS is layered on top. After a 30-minute centrifugation at 400×g, with the brake off, the mononuclear cell layer is transferred to a fresh tube, diluted 5× with PBS containing 2% FBS and centrifuged for 8 minutes at 300×g. For Donor 555130, 555131, and 555175, PBMCs were isolated from peripheral blood from healthy donors using EasySep Direct Human PBMC Isolation Kit from Stem Cell Technologies and following the manufacturers protocol. Isolated PBMC's were frozen in FBS containing 10% DMSO. For CD3+ T-cell isolation, frozen vials of PBMC's were thawed in a 37 C water bath and diluted in stimulation media (X-VIVO 15 cell culture media supplemented with 10% FBS, HEPES, NaPyr, NEAA, and 0.01 mM BME) containing 50 U/ml benzonase nuclease. Cells were centrifuged at 1200 rpm for 10 minutes, resuspended in EasySep buffer and isolated using StemCell Technologies EasySep T-Cell Isolation kit, following the manufacturers protocol.
IL-2 Release from Primary CD3$^+$ T-Cells Treated with CD28 Antibodies:
T-Cell Activation Assay with Human OVCAR-3, PEO1, NALM-6, RAJI/CD80–CD86–, and WSU-DLCL2 cells (+/−PD-L1)

CD3+ T cells, resuspended in stimulation media (X-VIVO 15 cell culture media supplemented with 10% FBS, HEPES, NaPyr, NEAA, and 0.01 mM BME), were plated out into 96-well round bottom plates at a concentration of 1×10$^5$ cells/well. NALM-6, RAJI/CD80–CD86–, WSU-DLCL2 cells with or without PD-L1 (+/−PD-L1), were treated with either 20 µg/mL (RAJI) or 15 µg/mL (NALM-6 and WSU-DLCL2), mitomycin C to arrest proliferation. After incubation for 1 hour at 37° C., 5% CO2, mitomycin C-treated cells were washed 3 times with D-PBS containing 2% FBS, followed by resuspension in stimulation media. NALM-6, RAJI/CD80–CD86–, and WSU-DLCL2 cells (+/−PD-L1) cells were added to wells containing CD3+ T cells at a final concentration of 2.5×10$^4$ cells/well for RAJI and WSU-DLCL2 cells and 5×10$^4$ for NALM-6 cells. A constant concentration of cemiplimab or non-binding IgG4$^P$ control (20 nM) was added to wells. In assays using WSU-DLCL2 (+/−PD-L1) cells a constant concentration of belatacept (hCTLA4.hIgG1) or non-binding IgG1 control (50 nM) was added to wells. Subsequently, REGN5837 or a non-TAA×CD28 control antibody was titrated from 3.1 pM to 200 nM in a 1:4 dilution series for NALM-6 (+/−PD-L1) cells and from 0.6 pM to 1000 nM in a 1:6 dilution series for WSU-DLCL2 and RAJI/CD80–CD86– (+/−PD-L1) cells and added to wells. The final point of the 10-point concentration curve contained no REGN5837 or non-TAA×CD28 control antibody. After incubating plates for 72 h (WSU-DLCL2 (+/−PD-L1)) or 96 h (NALM-6 and RAJI/CD80−CD86− (+/−PD-L1)) at 37° C., 5% CO02, 50 µL of media supernatant was collected to measure IL-2 release.

For IL-2 release, 5 µL of supernatant was tested using the human IL-2 AlphaLISA kit according the manufacturer's protocol. The IL-2 measurements were acquired on Perkin Elmer's multilabel plate reader Envision. A standard curve of know IL-2 concentrations was included and was used to derive pg/ml values.

All serial dilutions were tested in triplicate for IL-2 release. The EC50 values for the antibodies were determined from a 4-parameter logistic equation over a 10-point dose-response curve using GraphPad Prism™ software. Maximal levels of IL-2 release are given as the mean maximal response detected within the tested dose range. Additionally, data reported for assays using WSU-DLCL2 cells include the IL-2 values generated in the absence or presence of 1000 nM titrated antibody, in order to capture the decrease in IL-2 observed with increasing concentration of non-TAA×CD28 antibody.

Results Summary and Conclusions:

IL-2 Functional Assay Using Primary Human CD3+ T-Cells:

The ability of anti-CD22×anti-CD28 bispecific antibodies to provide co-stimulation through CD28 on T-cells in the presence of B-cell lymphocyte cell lines, which endogenously express CD22, was assessed in a functional primary CD3+ T-cell assay measuring IL-2 cytokine production.

Figure 4:
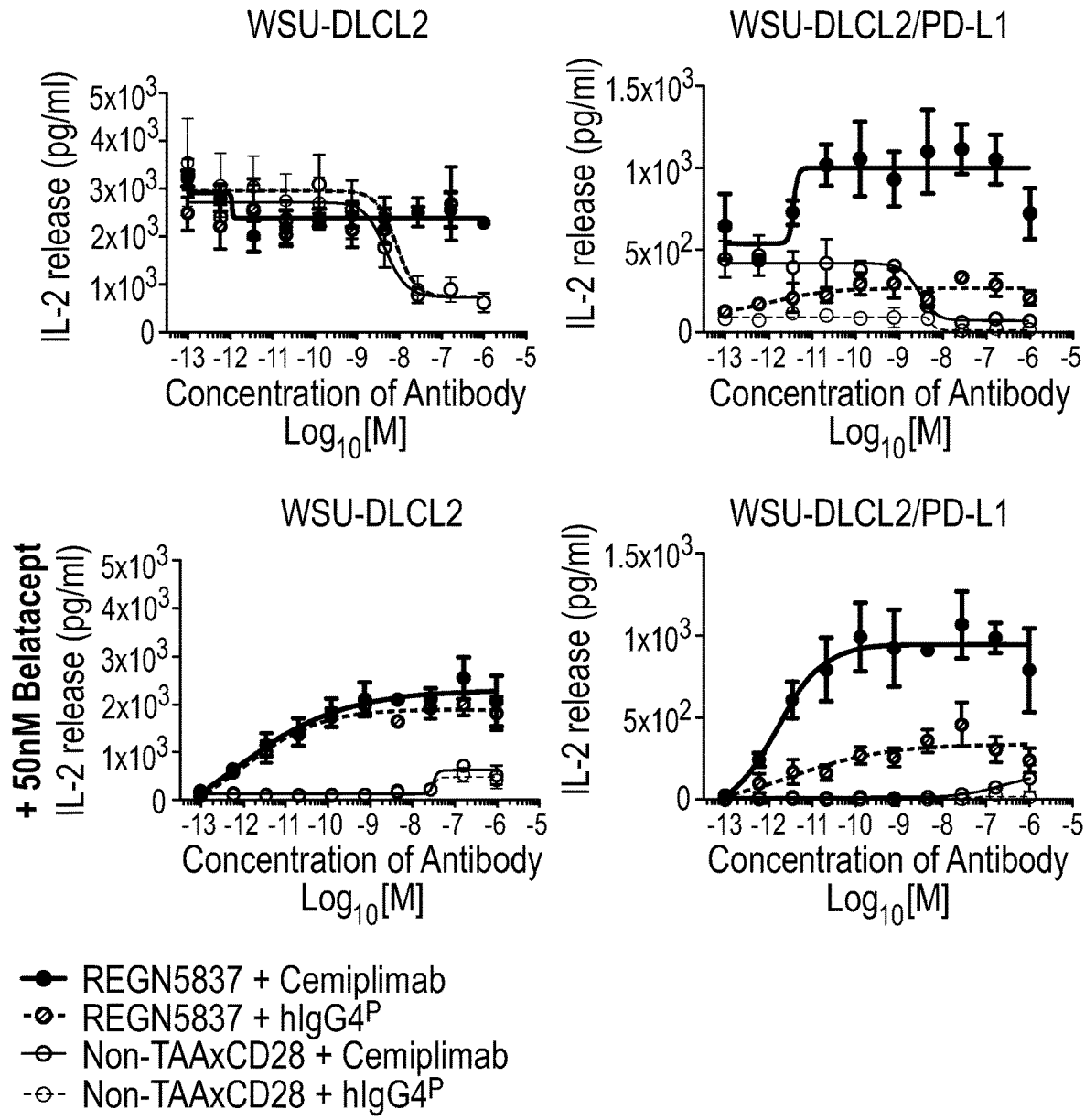
FIG. 4 is a set of graphs showing that a combination of REGN5837 with cemiplimab enhances IL-2 release above REGN5837 treatment alone in cells engineered to express PD-L1.
Figure 5A:
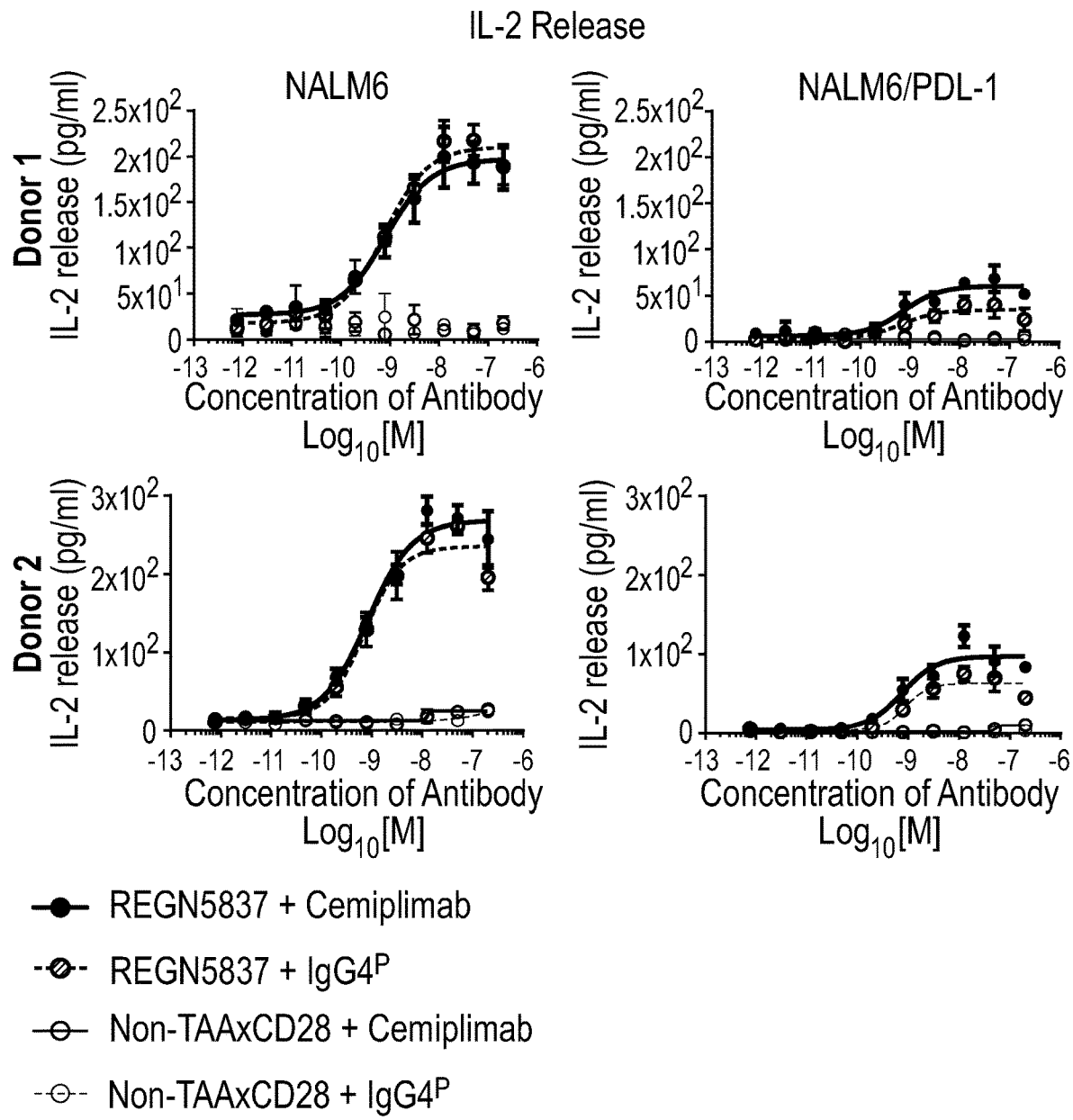
FIG. 5A is a set of graphs showing that a combination of REGN5837 with cemiplimab enhances IL-2 release in the presence of NALM6 cells engineered to express PD-L1.
Figure 5B:
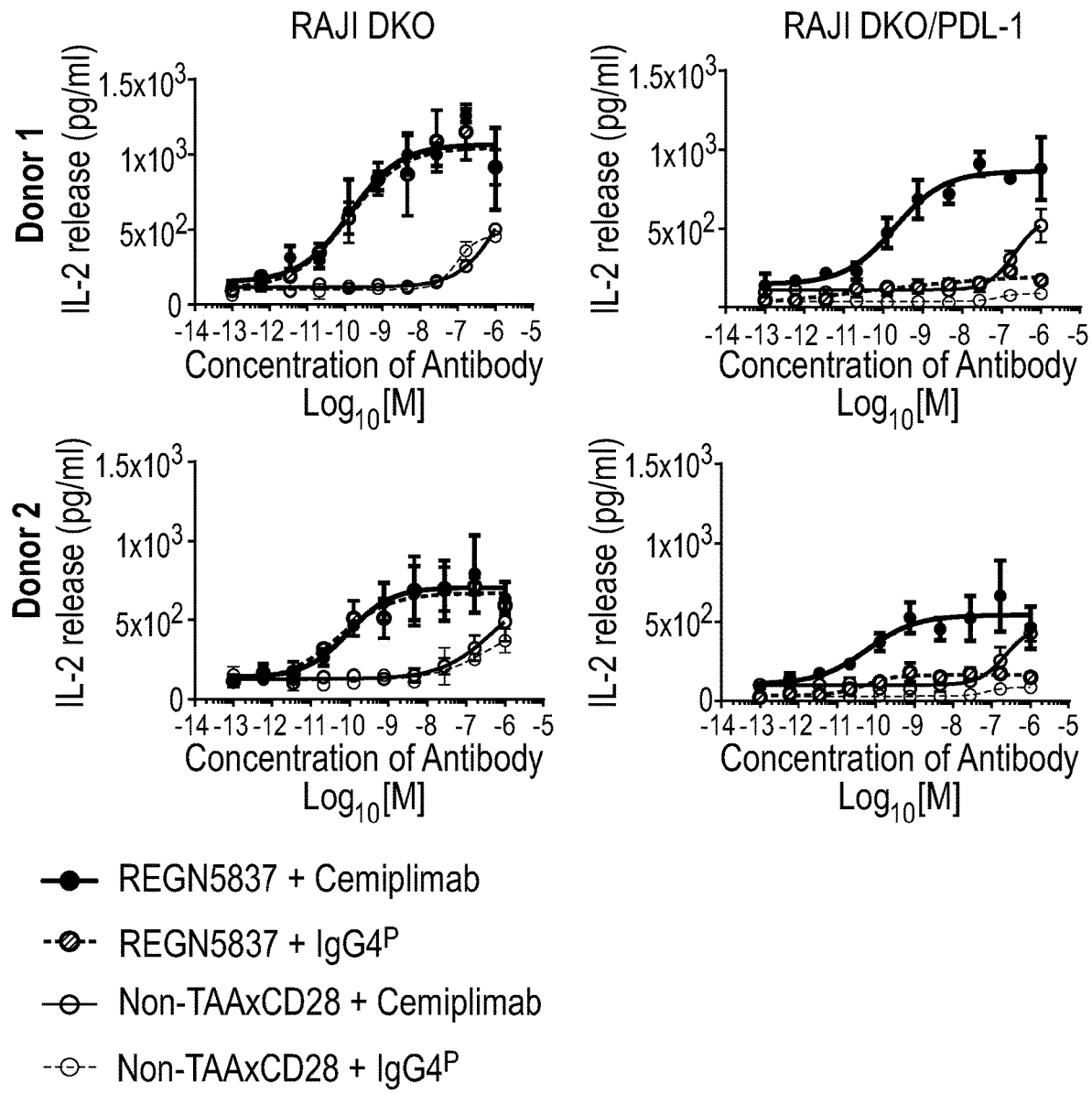
FIG. 5B is a set of graphs showing that a combination of REGN5837 with cemiplimab enhances IL-2 release above REGN5837 treatment alone in RAJI cells engineered to express PD-L1.

Activation curves are shown in FIGS. 5A and 5B for T-cells incubated with NALM-6 (+/−PD-L1) (FIG. 5A) or RAJI/CD80−CD86− (+/−PD-L1) (FIG. 5B). EC50 and Max IL-2 values are summarized in Table 23A for CD3+ T-cells incubated with NALM-6 (+/−PD-L1) cells and Table 23B for CD3+ T-cells incubated with RAJI/CD80−CD86− (+/−PD-L1) in the presence of either 20 nM constant hIgG4$^P$ isotype control or cemiplimab. For CD3+ T-cells incubated with WSU-DLCL2 (+/−PD-L1) cells, activation curves are shown in FIG. 4. EC50 and IL-2 values (reported for 0 nM or 1000 nM REGN5837 or non-TAA×CD28) are summarized in Table 24 for T-cells incubated with WSU-DLCL2 (+/−PD-L1) cells in the presence of either 20 nM constant hIgG4$^P$ isotype control or cemiplimab and in the presence of either 50 nM constant hIgG1 isotype control or the CTLA-4 receptor, belatacept.

In the presence of human primary T cells and the allogeneic B-cell lymphocyte cell lines RAJI/CD80−CD86− and NALM-6, REGN5837 mediated concentration-dependent increases in IL-2 release. The non-TAA×CD28 control antibody slightly increases IL-2 at high antibody concentrations. In the absence of PD-L1 on RAJI/CD80−CD86− or NALM-6 cells, the addition of 20 nM cemiplimab has no impact on IL-2 release. In the presence of RAJI/CD80−CD86− or NALM-6 cells expressing PD-L1, the maximum IL-2 released in response to treatment with REGN5837 alone is reduced, in comparison to T-cells incubated with non-PD-L1 expressing cells. Addition of cemiplimab minimally enhances REGN5837-mediated IL-2 release in conditions with NALM-6/PD-L1 cells, whereas it significantly enhances IL-2 release in in the presence of RAJI/CD80−CD86−/PD-L1 cells, to levels observed in conditions with RAJI/CD80-CD86− cells, lacking PD-L1.

In the presence of human primary T-cells and the allogeneic B-cell lymphocyte cell line WSU-DLCL2, no concentration-dependent increase in IL-2 release was observed. The non-TAA×CD28 control antibody, conversely, was observed to decrease IL-2 release in a concentration-dependent manner. Unlike NALM-6 and RAJI/CD80−CD86− cells, which express little to no CD28 ligands, the WSU-DLCL2 cell line is known to express CD28 ligands. As the CD28 binding arm of REGN5837, and thus the CD28 arm of the non-TAA×CD28 antibody, is known to compete with CD28 ligands for binding to CD28, the non-TAA×CD28 control antibody blocks CD28 activation by CD28 ligand expressed on the WSU-DLCL2 cells, leading to decreased IL-2 release. Unlike the non-TAA×CD28 control, IL-2 is not decreased by REGN5837, due to its ability to anchor to WSU-DLCL2 cells via it's CD22 binding arm allowing it to behave similarly to CD28 ligands, essentially replacing them. In the presence of WSU-DLCL2/PD-L1 cells, basal IL-2 release is decreased in comparison to WSU-DLCL2 cells not expressing PD-L1. Addition of REGN5837 alone, in the absence of cemiplimab leads to a slight enhancement of IL-2 release. Upon addition of 20 nM cemiplimab, basal activity is enhanced and can be enhanced slightly further with a dose titration of REGN5837, making the max IL-2 release higher for the combination of REGN5837 and cemiplimab, compared to either treatment alone. As observed with the WSU-DLCL2 cells, incubation of WSU-DLCL2/PD-L1 cells in the presence of Non-TAA×CD28 leads to decreased IL-2 levels, irrespective if cemiplimab or the hIgG4$^P$ isotype control is present. To further explore the impact CD28 ligand expression has on masking the impact of REGN5837, the soluble CTLA-4 receptor belatacept, or a hIgG1 matched isotype control, was added at 50 nM. Belatacept binds with high affinity to CD28 ligands, CD80 and CD86, and blocks their interaction and therefore activation of CD28. In the presence of 50 nM Belatacept, basal IL-2 release is dramatically reduced, due to the inability of CD28 ligands to bind CD28 and provide costimulatory signaling. Under these conditions REGN5837 is still able to engage CD28 and provide costimulation, noted by the dose dependent enhancement of IL-2 release. While addition of 20 nM cemiplimab, by itself, does not enhance IL-2 release in the presence of belatacept, combination of cemiplimab with increasing doses of REGN5837 increases max IL-2 release, compared to REGN5837 alone, in the presence of cells engineered to over-express PD-L1.

TABLE 23A

Combination of REGN5837 with Cemiplimab Enhances IL-2 Release Above REGN5837 Treatment Alone in NALM-6 Cells Engineered to Express PD-L1

| Primary T-Cells + NALM-6 (+/−PD-L1) | | | | Max [pg/ml] | EC$_{50}$ [M] |
|---|---|---|---|---|---|
| Donor 555109 T-Cells | NALM-6 | REGN5837 | Cemiplimab | 199.50 | 8.22E−10 |
| | | | hIgG4$^P$ | 217.80 | 7.54E−10 |
| | | Non-TAA × CD28 | Cemiplimab | 21.71 | ND |
| | | | hIgG4$^P$ | 24.74 | ND |
| | NALM-6/ hPD-L1 | REGN5837 | Cemiplimab | 68.34 | 7.42E−10 |
| | | | hIgG4$^P$ | 40.26 | 6.70E−10 |
| | | Non-TAA × CD28 | Cemiplimab | 10.07 | ND |
| | | | hIgG4$^P$ | 11.80 | ND |

TABLE 23A-continued

Combination of REGN5837 with Cemiplimab Enhances IL-2 Release Above REGN5837 Treatment Alone in NALM-6 Cells Engineered to Express PD-L1

| | Primary T-Cells + NALM-6 (+/−PD-L1) | | | Max [pg/ml] | $EC_{50}$ [M] |
|---|---|---|---|---|---|
| Donor 555130 T-Cells | NALM-6 | REGN5837 | Cemiplimab | 281.00 | 8.31E−10 |
| | | | hIgG4$^P$ | 261.30 | 7.18E−10 |
| | | Non-TAA × CD28 | Cemiplimab | 27.51 | ND |
| | | | hIgG4$^P$ | 25.18 | ND |
| | NALM-6/ hPD-L1 | REGN5837 | Cemiplimab | 123.20 | 7.50E−10 |
| | | | hIgG4$^P$ | 75.29 | 8.72E−10 |
| | | Non-TAA × CD28 | Cemiplimab | 10.29 | ND |
| | | | hIgG4$^P$ | 3.31 | ND |
| Donor 555131 T-Cells | NALM-6 | REGN5837 | Cemiplimab | 294.20 | 9.96E−10 |
| | | | hIgG4$^P$ | 264.90 | 1.05E−09 |
| | | Non-TAA × CD28 | Cemiplimab | 21.13 | ND |
| | | | hIgG4$^P$ | 25.45 | ND |
| | NALM-6/ hPD-L1 | REGN5837 | Cemiplimab | 90.17 | 8.57E−10 |
| | | | hIgG4$^P$ | 50.99 | 8.95E−10 |
| | | Non-TAA × CD28 | Cemiplimab | 11.35 | ND |
| | | | hIgG4$^P$ | 6.57 | ND |

ND: Not determined because a concentration-dependent response was not observed.

TABLE 23B

Combination of REGN5837 with Cemiplimab Enhances IL-2 Release Above REGN5837 Treatment Alone in RAJI/CD80$^-$CD86$^-$ Cells Engineered to Express PD-L1

| | Primary T-Cells + RAJI/CD80$^-$CD86$^-$ (+/−PD-L1) | | | Max [pg/ml] | $EC_{50}$ [M] |
|---|---|---|---|---|---|
| Donor 555109 T-Cells | RAJI/CD80$^-$ CD86$^-$ | REGN5837 | Cemiplimab | 1258.00 | 1.41E−10 |
| | | | hIgG4$^P$ | 1149.00 | 1.28E−10 |
| | | Non-TAA × CD28 | Cemiplimab | 503.70 | NC |
| | | | hIgG4$^P$ | 454.90 | 9.49E−08 |
| | RAJI/CD80$^-$ CD86$^-$/PD-L1 | REGN5837 | Cemiplimab | 910.70 | 1.97E−10 |
| | | | hIgG4$^P$ | 230.60 | 3.86E−11 |
| | | Non-TAA × CD28 | Cemiplimab | 518.80 | NC |
| | | | hIgG4$^P$ | 84.41 | 8.20E−08 |
| Donor 555130 T-Cells | RAJI/CD80$^-$ CD86$^-$ | REGN5837 | Cemiplimab | 791.90 | 9.31E−11 |
| | | | hIgG4$^P$ | 711.60 | 5.04E−11 |
| | | Non-TAA × CD28 | Cemiplimab | 489.70 | NC |
| | | | hIgG4$^P$ | 370.00 | NC |
| | RAJI/CD80$^-$ CD86$^-$/PD-L1 | REGN5837 | Cemiplimab | 664.30 | 6.15E−11 |
| | | | hIgG4$^P$ | 182.10 | 5.24E−11 |
| | | Non-TAA × CD28 | Cemiplimab | 426.80 | NC |
| | | | hIgG4$^P$ | 85.29 | 7.24E−08 |
| Donor 555131 T-Cells | RAJI/CD80$^-$ CD86$^-$ | REGN5837 | Cemiplimab | 437.40 | 1.28E−10 |
| | | | hIgGA$^P$ | 426.10 | 9.31E−11 |
| | | Non-TAA × CD28 | Cemiplimab | 162.20 | 5.97E−08 |
| | | | hIgG4$^P$ | 156.60 | 7.92E−08 |
| | RAJI/CD80$^-$ CD86$^-$/PD-L1 | REGN5837 | Cemiplimab | 406.00 | 3.16E−10 |
| | | | hIgG4$^P$ | 132.40 | 2.58E−10 |
| | | Non-TAA × CD28 | Cemiplimab | 94.94 | NC |
| | | | hIgG4$^P$ | 37.24 | NC |

NC: Not calculated because the data did not fit a 4-parameter logistic equation.

TABLE 24

Combination of REGN5837 with Cemiplimab Enhances IL-2 Release Above REGN5837 Treatment Alone in WSU-DLCL2 Cells Expressing PD-L1

| | Primary T-Cells + WSU-DLCL2 (+/−PD-L1) | | | IL-2 at 100 nM [pg/ml] | IL-2 at 0 nM [pg/ml] | $EC_{50}$ [M] | $IC_{50}$ [M] |
|---|---|---|---|---|---|---|---|
| Donor 555175 T-Cells | WSU-DLCL2 | REGN5837 | Cemiplimab | 2276.35 | 3217.69 | | ND |
| | | | hIgG4$^P$ | 2284.28 | 2482.54 | | ND |
| | | Non-TAA × CD28 | Cemiplimab | 609.01 | 3299.38 | | 4.81E−09 |
| | | | hIgG4$^P$ | 616.95 | 3552.86 | | 8.54E−09 |

TABLE 24-continued

Combination of REGN5837 with Cemiplimab Enhances IL-2 Release Above
REGN5837 Treatment Alone in WSU-DLCL2 Cells Expressing PD-L1

| Primary T-Cells + WSU-DLCL2 (+/−PD-L1) | | | IL-2 at 100 nM [pg/ml] | IL-2 at 0 nM [pg/ml] | $EC_{50}$ [M] | $IC_{50}$ [M] |
|---|---|---|---|---|---|---|
| | WSU-DLCL2/PD-L1 | REGN5837 | Cemiplimab | 723.06 | 642.64 | NC | |
| | | | $hIgG4^P$ | 209.84 | 124.81 | 1.39E−12 | |
| | | Non-TAA × CD28 | Cemiplimab | 66.17 | 444.51 | | 2.87E−09 |
| | | | $hIgG4^P$ | 15.47 | 82.91 | | NC |
| Donor 555175 T-Cells + 50 nM Belatacept | RAJI/CD80⁻CD86⁻ | REGN5837 | Cemiplimab | 2061.29 | 112.64 | 6.95E−13 | |
| | | | $hIgG4^P$ | 1809.89 | 71.65 | 1.45E−12 | |
| | | Non-TAA × CD28 | Cemiplimab | 502.33 | 164.55 | NC | |
| | | | $hIgG4^P$ | 402.66 | 109.02 | NC | |
| | RAJI/CD80⁻CD86⁻/PD-L1 | REGN5837 | Cemiplimab | 792.06 | 22.40 | 1.59E−12 | |
| | | | $hIgG4^P$ | 238.23 | 5.19 | 3.39E−12 | |
| | | Non-TAA × CD28 | Cemiplimab | 128.69 | 24.44 | NC | |
| | | | $hIgG4^P$ | 14.49 | 1.72 | NC | |

ND: Not determined because a concentration-dependent response was not observed.
NC: Not calculated because the data did not fit a 4-parameter logistic equation.

Example 11: Anti-Tumor Efficacy of Administration of REGN5837 in the Presence and Absence of REGN1979

Introduction

REGN5837 is a human IgG4-based bispecific antibody (bsAb) designed to target B cell NHLs (e.g., DLBCL) by bridging CD22+ B cells with CD28+ T cells. The "signal 2" provided by REGN5837, in combination with other agents providing "signal 1" (e.g., delivering a signal via primary T-cell stimulation via the TCR or CD3 clustering), such as the CD20×CD3 bispecific antibody (bsAb) REGN1979, may provide amplified T cell activation and T cell-mediated killing of B cell NHLs, deepening the response to CD20×CD3. Furthermore, REGN5837 may provide increased efficacy in patients unresponsive to CD20×CD3 monotherapy.

The studies described below evaluated the anti-tumor efficacy of the CD22×CD28 bsAb REGN5837, in the presence or absence of a sub-efficacious dose of CD20×CD3 bsAb (REGN1979), administered to immunodeficient NSG mice bearing 8-day, established B-cell leukemia tumors.

Briefly, mice (n=6 to 9 per group) were intraperitoneally (IP) engrafted with human peripheral blood mononuclear cells (PBMC) and intravenously (IV) implanted 12 days later with human NALM-6 B-cell leukemia cells, which were engineered to express luciferase to enable bioluminescence imaging (NALM-6-luc). The anti-tumor efficacy of REGN5837 at 0.04, 0.4, and 4 mg/kg, in combination with a fixed 0.04 mg/kg dose of REGN1979, was compared to REGN5837 and REGN1979 monotherapies and to non-bridging $IgG4^{P-PVA}$ control bsAbs. Mice received doses of antibodies by intraperitoneal (IP) injection 8, 15, and 22 days after implantation of NALM-6-luc cells. Tumor burden was assessed twice a week throughout the duration of the experiment.

Materials and Methods

Human-Derived Cell Lines

NALM-6-luc: The NALM-6 cell line is an acute lymphoblastic leukemia cell line isolated from a 19-year old male patient (DSMZ, cat #ACC 128); this line was modified with the EF1a-Luciferase-2A-GFP-Puro lentivirus (GenTarget) to facilitate imaging of tumor cell growth in vivo.

PBMC: Human PBMC were obtained from ReachBio, Cat. #0500-401, donor #0180905 (tumor growth experiment) and 0180621 (serum antibody experiment)

Experimental Design

Test System

Female NSG mice (age 8-9 weeks old) were used in all experiments. All mice were IP engrafted with human PBMC, and then IV implanted with NALM-6-luc B-cell leukemia cells 12 days after engraftment. The experimental design is detailed in Table 25. Tumor growth was monitored by bioluminescence imaging twice a week throughout the duration of the study. For all experiments, mice were housed in the Regeneron animal facility under standard conditions. All experiments were performed in accordance with the guidelines for the Institutional Animal Care and Use Committee at Regeneron.

Engraftment of NSG Mice

Female immunodeficient NSG mice were IP engrafted with $4 \times 10^7$ human PBMC. T cell levels were checked 11 days after engraftment by retro-orbital collection of blood and evaluation of the percent of human CD45+ cells in all live cells in whole blood by flow cytometry; the engraftment levels ranged from 0.16 to 16% $hCD45^+$ cells. PBMC-engrafted NSG mice were subsequently implanted with NALM-6-luc cells.

NALM-6-Luc Culture Conditions and Tumor Implantation

The NALM-6 cell line was modified with the EF1a-Luciferase-2A-GFP-Puro lentivirus (GenTarget) to facilitate imaging of tumor cell growth in vivo. The cell line was maintained in RPMI with 10% FBS supplemented with PSG (penicillin, streptomycin, and glutamine) and under puromycin selection.

NALM-6-luc cells were collected by centrifugation and re-suspended in PBS at $2.5 \times 10^7$ cells/mL. NSG mice were injected IV with 200 μl ($5 \times 10^6$ cells) of NALM-6-luc cells on day 12 post-engraftment with PBMC.

Antibody Dosing for Tumor Measurement

Prior to dosing with test articles or controls, mice were assigned to groups, stratified according to tumor burden and T-cell engraftment levels. Antibodies (REGN5837, REGN1979, REGN5671 [Non-TAA×CD28 non-bridging control bsAb], or H4sH17664D [Non-TAA×CD3 non-bridging control bsAb]) were administered as monotherapy or in combination by IP injection on days 8, 15, and 22 post-implantation (for in vivo efficacy) at the doses stated in Table 25.

TABLE 25

Experimental Design for Assessing Tumor Growth

| Groups | N per Group | Dose of REGN5837 or Non-TAA × CD28 | Dose of REGN1979 or Non-TAA × CD3 | Ab Dosing Schedule (IP Injection) | Days Tumor Volumes Measured |
|---|---|---|---|---|---|
| REGN5837 + REGN1979 | 8 | 4 mg/kg | 0.04 mg/kg | Days 8, 15, and 22 post-implantation of NALM-6-luc cells | Days 6, 10, 14, 17, 20, and 23 post-implantation |
| REGN5837 + REGN1979 | 8[a] | 0.4 mg/kg | | | |
| REGN5837 + REGN1979 | 9 | 0.04 mg/kg | | | |
| REGN5837 + Non-TAA × CD3 | 8[a] | 4 mg/kg | | | |
| Non-TAA × CD28 + REGN1979 | 8 | 4 mg/kg | | | |
| Non-TAA × CD28 + Non-TAA × CD3 | 9[a] | 4 mg/kg | | | |

[a]One mouse from this group died early during the experiment and was excluded. These deaths were not due to tumor burdon and were unlikely to be related to dosing with test articles as one mouse died in the control group Tumor Measurement and Designated Endpoint Mice implanted with NALM-6-luc tumors were imaged twice a week using an IVIS Spectrum instrument, and the data were analyzed using Living Image software. Prior to imaging, mice were IP injected with luciferin substrate. After ten minutes, mice were anesthetized with isoflurane and the bioluminescence (total flux, expressed as photons per second [p/s]) quantified. The experiment was ended when mice began exhibiting signs of graft versus host disease (GVHD) (assessed as weight loss >20%) in accordance with IACUC standards.

Statistical Analysis of Tumor Growth

Results of tumor volume over time were analyzed using a 2-way analysis of variance (ANOVA) followed by Tukey's post hoc test for multiple comparisons. Differences were considered statistically significant when p<0.05. Statistical analyses were performed using GraphPad Prism software (Version 8).

Results

Anti-Tumor Efficacy of Administration of REGN5837 in the Presence and Absence of REGN1979

Immunodeficient NSG Mice Bearing NALM-6-Luc Tumors Received IP Injections of Antibodies or Non-Bridging Controls as Described Above.

Figure 6:
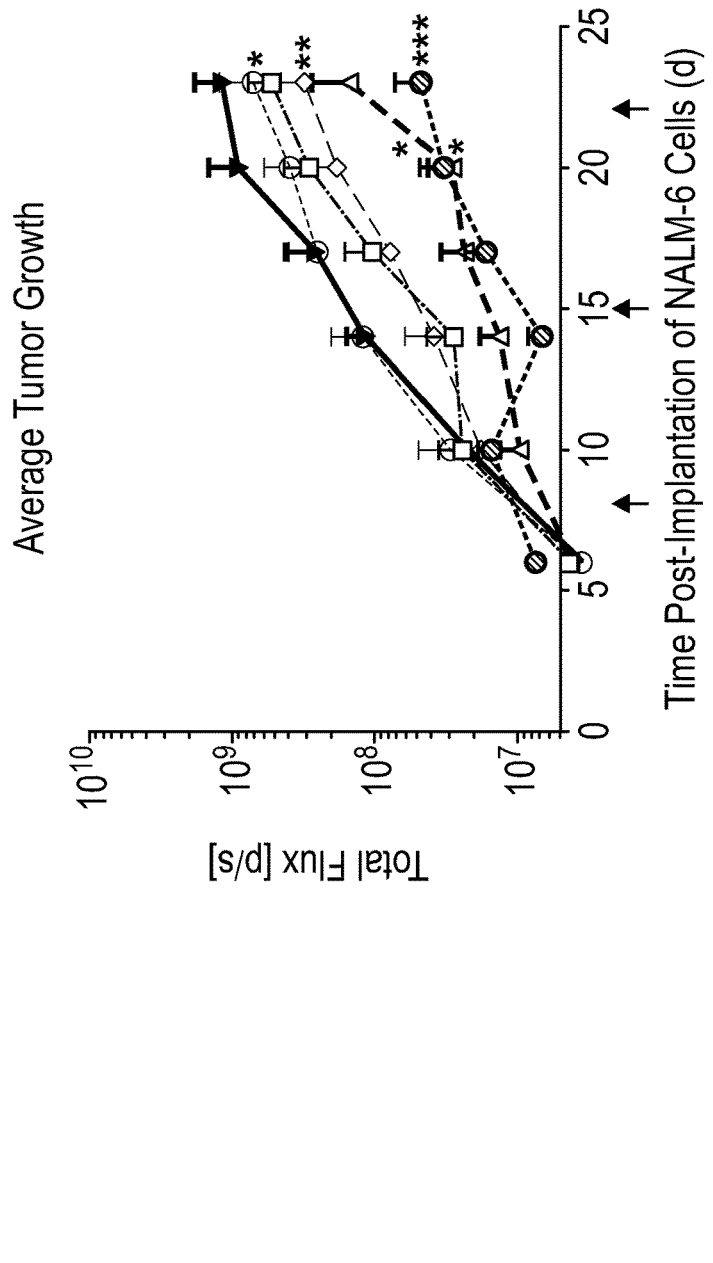
FIG. 6 is a graph showing that treatment of NSG mice bearing NALM-6-Luc tumors with REGN5837 in the presence of REGN1979 (anti-CD20×anti-CD3) is associated with significant tumor suppression. Briefly, NSG mice (n=6 to 9 per group) were engrafted with human PBMC, then implanted with NALM-6-luc B-cell leukemia cells 12 days post-engraftment (day 0). Mice were administered 4 mg/kg REGN5837+0.04 mg/kg REGN1979 (hashed circles), 0.4 mg/kg REGN5837+0.04 mg/kg REGN1979 (closed upright triangles), 0.04 mg/kg REGN5837+0.04 mg/kg REGN1979 (diamonds), 4 mg/kg non-TAA×CD28+0.04 mg/kg REGN1979 (squares), 4 mg/kg REGN5837+0.4 mg/kg non-TAA×CD3 (open circles), or 4 mg/kg non-TAA×CD28+0.4 mg/kg non-TAA×CD3 (closed inverted triangles) on days 8, 15, and 22 post-implantation (arrows). Tumor growth was monitored by bioluminescent imaging of tumor volume on days 6, 10, 14, 17, 20, and 23 post-implantation. Combined data are expressed as the group mean±SEM. Statistical significance was determined using two-way ANOVA with Tukey's post hoc test. The following symbols were used to indicate statistically significant differences relative to non-TAA×CD28+non-TAA×CD3 control: *, $p<0.05$; , $p<0.01$; *, $p<0.001$.

In tumor-bearing mice, treatment with 0.04, 0.4, and 4 mg/kg REGN5837 in the presence of 0.04 mg/kg REGN1979 resulted in statistically significant suppression of tumor growth compared with non-bridging control bsAbs (non-TAA×CD28 and non-TAA×CD3 bsAbs) at day 23 post-implantation (p<0.05, p<0.01, and p<0.001, respectively) (FIG. 6). On day 20 post-implantation, significant suppression of tumor growth was observed for the 0.4 and 4 mg/kg groups (p<0.05 for both groups). Neither REGN5837 (4 mg/kg) nor REGN1979 (0.04 mg/kg) monotherapy significantly reduced tumor growth compared with non-bridging control bsAbs. No difference between any REGN5837+REGN1979 combination dose and either bsAb monotherapy reached statistical significance. Rapid tumor growth was observed upon dosing with non-bridging control bsAbs throughout the dosing period, and all mice were euthanized on day 23. In all groups, GVHD was observed in at least one mouse at the end of the experiment (assessed as >20% reduction in weight).

In an independent experiment using a different set of mice, blood was collected at the following timepoints to determine serum antibody concentrations: 1 and 4 hours post-dose on day 7, 1 hour pre-dose and 4 hours post-dose on days 14 and 21, and once on day 29. Trough concentrations of antibodies in serum during the dosing period were determined 1 hour prior to dosing on days 14 and 21. Administration of REGN5837 doses of 0.04, 0.4, and 4 mg/kg in the presence of 0.04 mg/kg REGN1979 was associated with trough concentrations of REGN5837 in serum ranging from below the limit of quantitation (BLQ) to 0.1, 1.6 to 2.3, and 16.5 to 21.1 µg/mL, respectively. Trough concentrations of REGN1979 in serum were BLQ in all cases (Data not shown).

Conclusions

Doses of 0.04, 0.4, and 4 mg/kg REGN5837 in the presence of 0.04 mg/kg REGN1979 were effective at suppressing NALM-6 B-cell leukemia tumor growth in mice. No significant tumor suppression was observed with either 4 mg/kg REGN5837 or 0.04 mg/kg REGN1979 monotherapy relative to control.

Example 12: FACS Based Cytotoxicity on CD22 Cells+Human PBMC+/−CD22×CD28 Costimulatory Bispecific Antibody (Fixed CD22×CD28, Titrated CD20×CD3)

Materials and Methods

CD22×CD28 enhancement of CD20×CD3 targeted killing was evaluated in a 96-hour cytotoxicity assay targeting Nalm6 or WSU-DLCL2 cells. Briefly, human PBMCs were plated in supplemented RPMI media at $1 \times 10^6$ cells/mL and incubated overnight at 37° C. in order to enrich for lymphocytes by depleting adherent macrophages, dendritic cells, and some monocytes. The following day, Nalm6 or WSU-DLCL2 cells were labeled with 1 uM of the fluorescent tracking dye CFDA-SE and the adherent cell-depleted naïve PBMC were labeled with 1 uM of the fluorescent tracking dye CellTrace Violet. Labeled target cells and PBMC (Effector/Target cell 4:1 ratio for Nalm6, 5:1 for WSU-DLCL2) were co-incubated a serial dilution of CD20×CD3 bispecific antibody REGN1979 (concentration range: 5 nM to 0.64 pM) with or without a fixed concentration of CD22×CD28 REGN5837 at 2.5 ug/ml (16.7 nM). In the assay targeting Nalm6 cells, a constant amount of CD22× CD28 REGN5838, 1-arm control CD28 bispecific (REGN5678) or IgG4s isotype control (H4sH10154P3) at 2.5 ug/ml (16.7 nM) was added. After incubation for 96 hours at 37° C., cells were harvested from the plates and analyzed by FACS on a FACS BD LSRFortessa-X20. For FACS analysis, cells were stained with a Fixable Live/Dead Far Red reactive (Invitrogen) dye. 20,000 counting beads were added to each well immediately before FACS analysis and 10,000 beads were collected for each sample. For the assessment of specificity of killing, cells were gated on live CFDA-SE labeled populations. The percent or number of live target cells was recorded and used for the calculation of survival.

T cell activation was assessed by incubating cells with directly conjugated antibodies to CD2, CD4, CD8, and CD25. The percentage of CD8+ cells expressing CD25 was reported as the measure of T cell activation. Additionally, as T cells proliferate, CellTraceViolet is diluted, leading to lower MFI as measured by FACS. T cell proliferation was thus reported as a decrease in the MFI of CellTraceViolet on CD8+ T cells, or as the percentage of CD8+ cells that had decreased CellTraceViolet MFI.

Supernatants from this assay were collected for analysis of cytokine levels. Concentrations of IL 17a, IFNγ, TNFα, IL-10, IL-6, IL-4, and IL-2 were analyzed using a Cytometric Bead Array (CBA) kit following the manufacturer's instructions. Cytokine levels were interpolated from the curves generated by the kit standards and reported as pg/mL. EC50 values for target cell killing, T cell activation, proliferation, and cytokine levels, and maximum cytokine levels were calculated using 4-parameter non-linear regression analysis in Prism software.

Results, Summary and Conclusions:

The anti-CD20×CD3 bispecific antibody REGN1979 was tested for its ability to induce naïve human T cells to kill target cells expressing human CD20 and CD22 in combination with a costimulatory CD22×CD28 antibody or 1-arm CD28 or isotype control antibodies.

REGN1979 activated and directed human T cells to kill Nalm6 (FIG. 7) or WSU-DLCL2 (FIG. 8) cells in a dose-dependent manner. The addition of a fixed concentration of CD22×CD28 bispecific antibodies to REGN1979 enhanced the cytotoxic efficacy (EC50) of REGN1979 against Nalm6 cells 4.7-5.2 fold when compared to REGN1979 with 1-arm CD28 or isotype control antibodies (Table 26) or 17.5 fold against WSU-DLCL2 cells when compared to REGN1979 alone (Table 27).

Figure 7A:
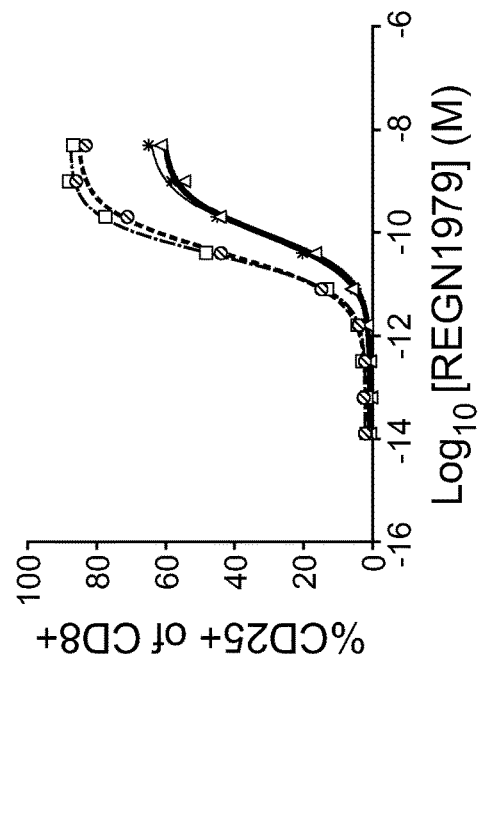
FIGS. 7A-7C are graphs showing that REGN1979 activated and directed human T cells to kill Nalm6 cells in a dose dependent manner. More specifically.
Figure 7B:
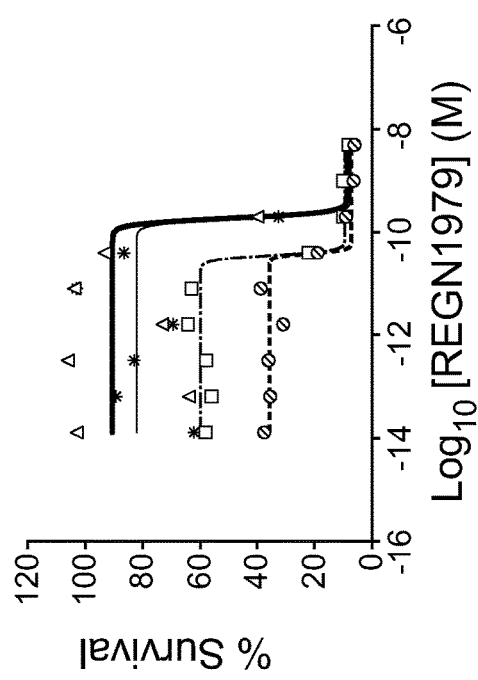
Figure 7C:
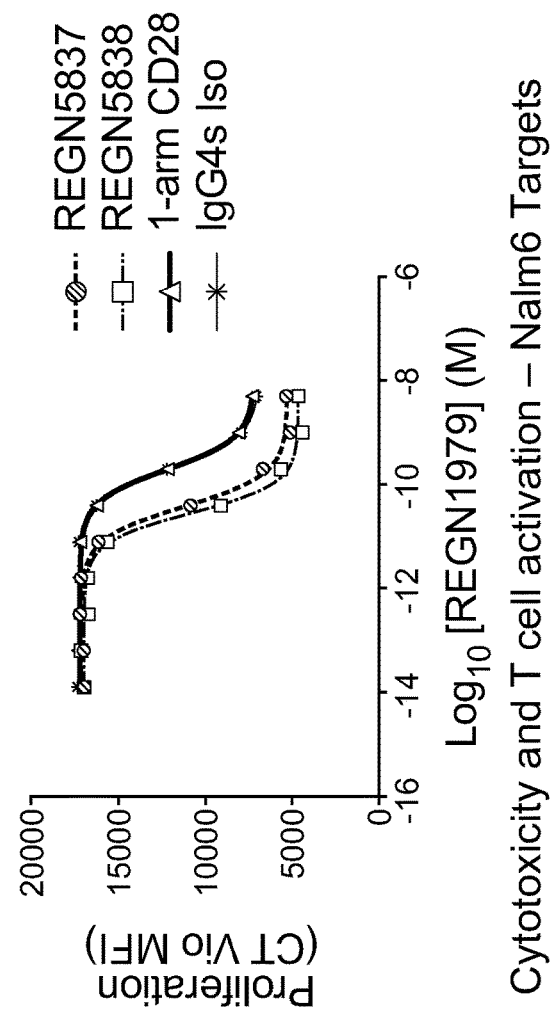

The observed target-cell lysis mediated by REGN1979 was associated with T cell activation and proliferation, as measured by CD25 upregulation on CD8+ cells or CellTrace violet dilution respectively (FIG. 7, FIG. 8). The addition of a fixed concentration of CD22×CD28 bispecific antibodies to REGN1979 enhanced the potency of REGN1979 induced T cell activation and proliferation in the presence of Nalm6 cells 2.3-2.6 fold and 5.4-7.1 fold respectively when compared to REGN1979 with 1-arm CD28 or isotype control antibodies (Table 26), or 8.2 and 16.1 fold in the presence of WSU-DLCL2 cells when compared to REGN1979 alone (Table 27).

Figure 9:
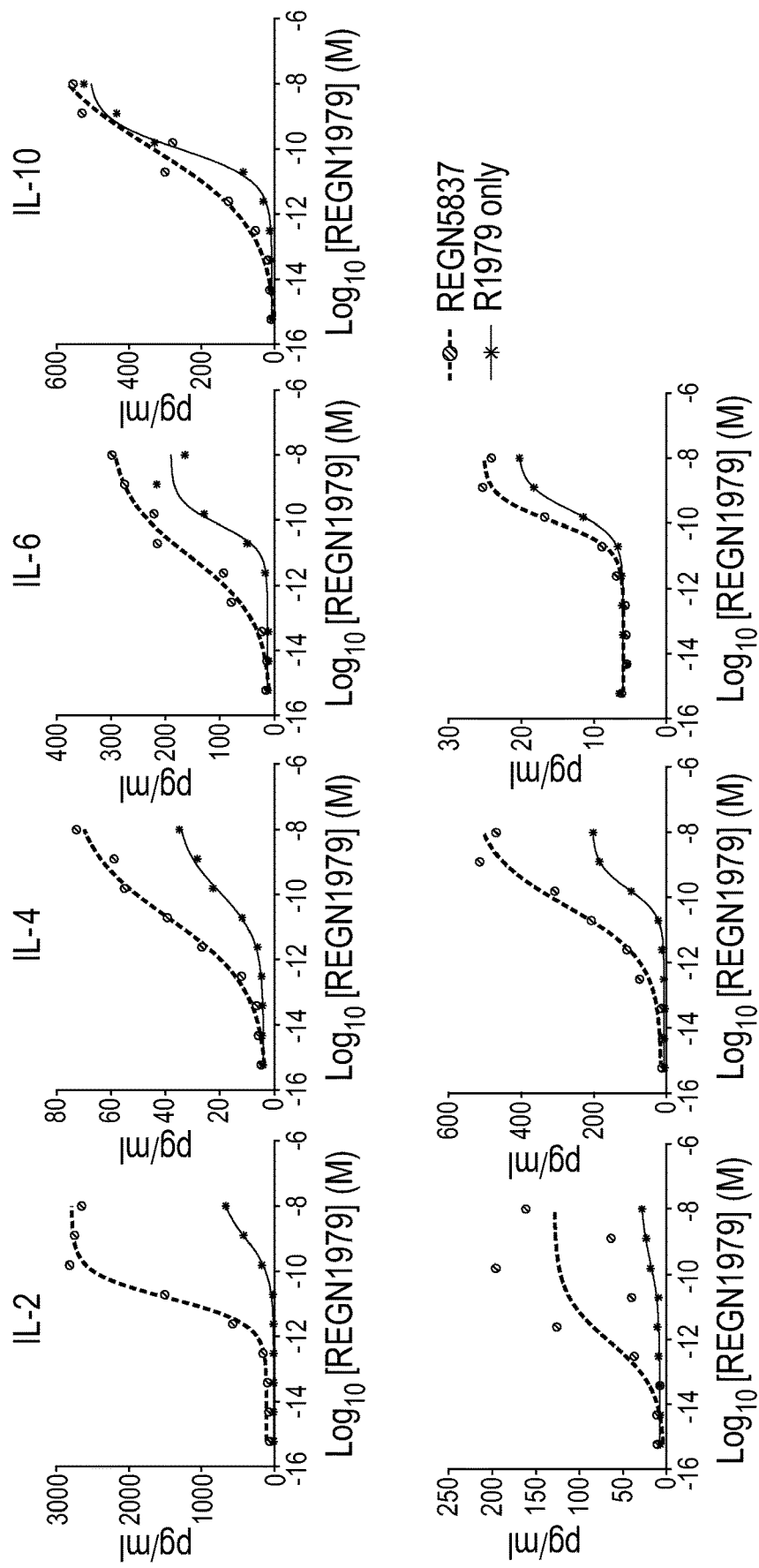
FIG. 9 is a set of graphs showing that in assays with human PBMC and WSU-DLCL2 cells, REGN1979 induced the release of human cytokines, IL-2, IL-4, IL-6, and IL-10. Cytokine release observed with REGN1979 was enhanced in the presence of a fixed concentration of CD22×CD28 compared to cytokine release induced by REGN1979 alone.

In assays with human PBMC and WSU-DLCL2 cells, REGN1979 induced the release of human cytokines. Cytokine released observed with REGN1979 was enhanced in the presence of a fixed concentration of a CD22×CD28 compared to cytokine release induced by REGN1979 alone (Table 28, FIG. 9).

In summary, co-stimulation increased the potency of targeted cytotoxicity, T cell activation, and cytokine release when compared to what was observed with CD20×CD3 in combination with control antibodies or alone.

Tabulated Data Summary:

TABLE 26

EC50 values for cytotoxicity and T cell activation with Nalm6 targets (1 experiment)

| Ab | Cell Kill | | T cell activation (CD8+/CD25+) | | T cell proliferatiom (CellTrace MFI of CD8+ cells) | |
|---|---|---|---|---|---|---|
| | EC50 [M] | Fold EC50 compared to IgG4s | EC50 [M] | Fold EC50 compared to IgG4s | EC50 [M] | Fold EC50 compared to IgG4s |
| REGN5837 | 3.89E−11 | 4.7 | 4.05E−11 | 2.3 | 3.83E−11 | 5.4 |
| REGN5838 | 3.57E−11 | 5.2 | 3.60E−11 | 2.6 | 2.87E−11 | 7.1 |
| 1-arm CD28 | 1.88E−10 | 1.0 | 9.20E−11 | 1.0 | 1.97E−10 | 1.0 |
| IgG4s Iso | 1.84E−10 | 1.0 | 9.28E−11 | 1.0 | 2.05E−10 | 1.0 |

TABLE 27

EC50 values for cytotoxicity and T cell activation with WSU-DLCL2 targets (Average of 2 experiments)

| Ab | Cell Kill | | T cell activation (CD8+/CD25+) | | T cell Proliferation (% Divided of CD8) | |
|---|---|---|---|---|---|---|
| | EC50 [M] | Fold EC50 compared to REGN1979 Only | EC50 [M] | Fold EC50 compared to REGN1979 Only | EC50 [M] | Fold EC50 compared to REGN1979 Only |
| REGN5837 | 1.39E−13 | 17.5 | 1.28E−12 | 8.2 | 7.10E−13 | 16.1 |
| No Ab | 2.33E−12 | 1.0 | 1.22E−11 | 1.0 | 1.23E−11 | 1.0 |

TABLE 28

Cytokine release from WSU-DLCL2 cytotoxicity assay (Average of 2 experiments)

|  |  | REGN5837 | No Ab |
|---|---|---|---|
| IL-2 | EC50 | 1.82E−11 | 5.85E−10 |
|  | Max (pg/ml) | 3022 | 564 |
|  | Fold (max) | 6.4 | 1.0 |
| IL-4 | EC50 | 1.24E−11 | 8.69E−11 |
|  | Max (pg/ml) | 65.035 | 34.855 |
|  | Fold (max) | 1.9 | 1.0 |
| IL-6 | EC50 | 2.31E−11 | 8.66E−11 |
|  | Max (pg/ml) | 194.36 | 116.085 |
|  | Fold (max) | 1.8 | 1.0 |
| IL-10 | EC50 | 1.35E−10 | 1.30E−10 |
|  | Max (pg/ml) | 686.15 | 520.7 |
|  | Fold (max) | 1.3 | 1.0 |
| TNFa | EC50 | 3.84E−11 | 2.09E−10 |
|  | Max (pg/ml) | 327.85 | 84.55 |
|  | Fold (max) | 4.1 | 1.0 |
| IFNg | EC50 | 1.06E−10 | 2.78E−10 |
|  | Max (pg/ml) | 470.7 | 195.5 |
|  | Fold (max) | 2.4 | 1.0 |
| IL-17a | EC50 | 2.56E−10 | 2.74E−10 |
|  | Max (pg/ml) | 19.775 | 15.091 |
|  | Fold (max) | 1.4 | 1.0 |

Example 13: FACS Based Cytotoxicity on NHL+Human PBMC+/−CD22×CD28 Stim (Fixed CD22×CD28, Titrated CD20×CD3)

Experimental Procedure

CD22×CD28 enhancement of CD20×CD3 targeted killing was evaluated in a 96-hour cytotoxicity assay targeting NHL cells isolated from primary NHL patient biopsy with autologous PBMC in the presence of human stromal cells (HS-5). Briefly, HS-5 cells were plated 5000 cells per well in a flat-bottom 96 well plate and were incubated overnight. The next day, PBMC from NHL patient were labeled with 1 uM of the fluorescent tracking dye CellTrace Violet. Bone marrow and labeled PBMC (Effector/Target cell 10:1 ratio) were plated in the wells with stromal cells and co-incubated with a serial dilution of CD20×CD3 bispecific antibody REGN1979 (concentration range: 6.7 nM to 10.7 pM) and a fixed concentration of CD22×CD28 costimulatory molecules REGN5837 or 1-arm control CD28 bispecific (REGN5678) at 2.5 ug/ml (16.7 nM) for 96 hours at 37° C. Cells were harvested from the plates and analyzed by FACS on a FACS BD LSRFortessa-X20. For FACS analysis, cells were stained with an antibody cocktail (CD45, CD19, CD4, CD8, CD25) and Fixable Live/Dead near IR reactive dye (Invitrogen). 20,000 counting beads were added to each well immediately before FACS analysis and 10,000 beads were collected for each sample. For the assessment of specificity of killing, target cells were gated on live CD45+ violet negative CD19+ population. Survival was calculated based on number of target cells in treated well normalized to number of target cells in untreated wells.

T cells were gated as live CD45+ violet labeled CD4+ or CD8+ populations. The percentage of CD8+ and CD4+ cells expressing CD25 was reported as the measure of T cell activation. Additionally, as T cells proliferate, CellTraceViolet is diluted, leading to lower MFI as measured by FACS. T cell proliferation was thus reported as a decrease in the MFI of CellTraceViolet on CD8+ and CD4+ T cells.

EC50 values for target killing and T cell activation and proliferation were calculated using 4-parameter non-linear regression analysis in Prism software.

Results Summary and Conclusions:

The anti-CD20×CD3 bispecific antibody REGN1979 was tested for its ability to induce naïve autologous T cells to kill NHL cells from patient bone marrow in combination with a costimulatory CD22×CD28 antibody or 1-arm CD28 control antibodies.

REGN1979 activated and directed human T cells to deplete NHL in a dose-dependent manner. The addition of a fixed concentration of CD22×CD28 bispecific antibodies to REGN1979 enhanced the cytotoxic efficacy (EC50) of REGN1979 2.3 and 3.5 fold when compared to REGN1979 with 1-arm CD28 control antibody or no costim control (Table 29).

The observed target-cell lysis mediated by REGN1979 was associated with T cell activation and proliferation, as measured by CD25 upregulation on CD8+ and CD4+ cells or CellTrace violet dilution respectively. The addition of a fixed concentration of CD22×CD28 bispecific antibodies to REGN1979 enhanced the potency of REGN1979 induced T cell activation and proliferation 2.8 to 4.2 fold and 2.8-4.8 fold respectively when compared to REGN1979 with 1-arm CD28 or no costim control (Table 29 and FIG. 10).

In summary, co-stimulation increased the potency of targeted cytotoxicity and T cell activation when compared to what was observed with CD20×CD3 in combination with control antibodies.

Tabulated Data Summary:

TABLE 29

EC50 values for cytotoxicity and T cell activation

| Ab | Cell Kill EC50 [M] | T cell activation (CD25+) EC50 [M] | | T cell division (CellTrace MFI of T cells) EC50 [M] | |
|---|---|---|---|---|---|
|  |  | CD8 T cells | CD4 T cells | CD8 T cells | CD4 T cells |
| REGN5837 | 7.81E−12 | 1.35E−11 | 6.96E−12 | 1.52E−11 | 8.54E−12 |
| 1-arm CD28 | 1.80E−11 | 4.01E−11 | 2.95E−11 | 4.71E−11 | 4.13E−11 |
| no costim | 2.72E−11 | 3.77E−11 | 2.74E−11 | 4.27E−11 | 3.93E−11 |

Example 14: In Vitro Characterization and In Vivo Evaluation of the Anti-Tumor Efficacy of REGN5837 Alone and in Combination with REGN1979 in a Model of Diffuse Large B-Cell Lymphoma (DLBCL)

Materials and Methods-Introduction to Studies and Summary of Results

In Vitro and In Vivo Studies were Conducted to Evaluate:

(1) the ability of REGN5837 to enhance activation of primary T cells by bridging CD28+ T cells with CD22+ target cells. T-cell activation was assessed using cytotoxicity against target cells, expression of cell-surface markers of T-cell activation, T-cell proliferation, and levels of cytokine release as readouts. Experiments were performed in the presence or absence of REGN1979, a CD20×CD3 bsAb that bridges CD3 molecules on T cells and CD20 target cells and leads to T-cell activation.

(2) the anti-tumor efficacy of the CD22×CD28 bsAb REGN5837, in the presence or absence of 0.4 or 4 mg/kg of REGN1979, administered to immunodeficient NSG mice bearing DLBCL tumors.

REGN5837 and REGN1979 were tested in combination at a range of concentrations to evaluate the effect of REGN5837 on REGN1979-mediated T-cell cytotoxicity against a human DLBCL cell line (WSU-DLCL2), upregulation of a marker of late T-cell activation (CD25), T-cell proliferation, and cytokine release from primary human T cells. REGN5837 enhanced the potency of REGN1979 to mediate T-cell cytotoxicity, CD25 cell-surface expression on $CD4^+$ and $CD8^+$ T cells, and proliferation of $CD4^+$ and $CD8^+$ T cells in a concentration-dependent manner. Similarly, REGN5837 enhanced the potency of REGN1979 to mediate cytokine release in a concentration-dependent manner. At concentrations ranging from 77.2 pM to 100 nM, REGN5837 increased the potency of REGN1979-mediated T-cell cytotoxicity against target cells; at concentrations ranging from 77.2 pM to 2.78 nM, REGN5837 increased the potency of REGN1979-mediated T-cell activation and proliferation, but higher concentrations of REGN5837 did not further increase the potency of REGN1979 (Table 30). The maximal amount of REGN1979-mediated target cell killing and T-cell proliferation was not substantially increased upon addition of REGN5837, whereas REGN5837 enhanced the maximal levels of REGN1979-mediated release of IL-2, IL-4, IL-6, IL-10, TNF-α, IFN-γ, and IL-17α in a concentration-dependent manner.

Immunodeficient NSG mice (n=6 to 7 per group) were subcutaneously (SC) implanted with a 1:1 ratio of WSU-DLCL2 cells and human PBMC. The anti-tumor efficacy of REGN5837 at 1 mg/kg, in combination with a 0.4 or 4 mg/kg dose of REGN1979, was compared to REGN5837 and REGN1979 monotherapies and to non-bridging $IgG4^{P-PVA}$ control bsAbs. Mice received doses of antibodies by intraperitoneal (IP) injection 1, 8, and 15 days after implantation of WSU-DLCL2 cells. Treatment with 1 mg/kg REGN5837 in the presence of 0.4 or 4 mg/kg REGN1979 resulted in statistically significant suppression of WSU-DLCL2 tumor growth compared with REGN5837 or REGN1979 monotherapies and non-bridging control bsAbs by day 28 post-implantation. REGN1979 monotherapy resulted in modest suppression of tumor growth, whereas REGN5837 monotherapy had no effect relative to non-bridging control.

In summary, when REGN5837 and REGN1979 were tested in combination at a range of concentrations in vitro, REGN5837 enhanced the potency of REGN1979 to mediate human T-cell activation in the presence of $CD22^+$ WSU-DLCL2 cells. The maximal levels of REGN1979-mediated cytokine release, but not cytotoxicity, T-cell activation, or proliferation, were increased in the presence of REGN5837. In vivo, 1 mg/kg REGN5837 in the presence of either 0.4 or 4 mg/kg REGN1979 was effective at suppressing WSU-DLCL2 B-cell lymphoma tumor growth in mice relative to either REGN5837 or REGN1979 monotherapy alone.

TABLE 30

Summary of the Effect of REGN5837 on REGN1979-Mediated T-cell Activation (Measured by Cytotoxicity Against Target Cells, CD25 Expression, and T-Cell Proliferation) Using Human PBMC

| | | Fixed Concentration of REGN5837 | | | | | |
|---|---|---|---|---|---|---|---|
| | | $1.00 \times 10^{-7}$ | $1.67 \times 10^{-8}$ | $2.78 \times 10^{-9}$ | $4.63 \times 10^{-10}$ | $7.72 \times 10^{-11}$ | 0 |
| WSU-DLCL2 Cell Killing | REGN1979 $EC_{50}$ (M)[a] | $8.53 \times 10^{-14}$ | $1.85 \times 10^{-13}$ | $3.98 \times 10^{-13}$ | $3.46 \times 10^{-13}$ | $8.37 \times 10^{-13}$ | $2.89 \times 10^{-12}$ |
| | Max % Toxicity | 81.5 | 79.8 | 80.6 | 87.5 | 82.1 | 83.2 |
| | Fold Change $(EC_{50})$[b] | 33.9 | 15.7 | 7.3 | 8.3 | 3.5 | 1.0 |
| $CD4^+$ T cell activation (% $CD25^+$) | REGN1979 $EC_{50}$ (M) | $1.16 \times 10^{-13}$ | $8.70 \times 10^{-14}$ | $7.11 \times 10^{-14}$ | $1.46 \times 10^{-13}$ | $2.08 \times 10^{-13}$ | $9.17 \times 10^{-13}$ |
| | Max % $CD25^+$ Cells | 94.1 | 95.6 | 94.2 | 91.9 | 91.7 | 92.4 |
| | Fold Change $(EC_{50})$ | | 7.9 | 10.5 | 12.9 | 6.3 | 4.4 | 1.0 |
| $CD8^+$ T cell activation (% $CD25^+$) | REGN1979 $EC_{50}$ (M) | | $6.32 \times 10^{-13}$ | $5.88 \times 10^{-13}$ | $2.68 \times 10^{-13}$ | $9.01 \times 10^{-13}$ | $1.64 \times 10^{-12}$ | $3.38 \times 10^{-12}$ |
| | Max % $CD25^+$ Cells | 89 | 90.9 | 89.7 | 86.2 | 88.4 | 87.1 |
| | Fold Change $(EC_{50})$ | 5.3 | 5.7 | 12.6 | 3.8 | 2.1 | 1.0 |
| $CD4^+$ T-cell Proliferation | REGN1979 $EC_{50}$ (M) | $8.42 \times 10^{-13}$ | $9.31 \times 10^{-13}$ | $4.25 \times 10^{-13}$ | $1.25 \times 10^{-12}$ | $2.36 \times 10^{-12}$ | $1.63 \times 10^{-11}$ |
| | Max % Proliferation | 54.72 | 54.09 | 54.79 | 52.06 | 44.73 | 38.67 |
| | Fold Change $(EC_{50})$[a] | 19.3 | 17.5 | 38.3 | 13.1 | 6.9 | 1.0 |
| $CD8^+$ T-cell Proliferation | REGN1979 $EC_{50}$ (M) | $1.55 \times 10^{-12}$ | $8.31 \times 10^{-13}$ | $7.09 \times 10^{-13}$ | $3.43 \times 10^{-12}$ | $8.36 \times 10^{-12}$ | $1.97 \times 10^{-11}$ |
| | Max % Proliferation | 59.1 | 58.9 | 60.2 | 56.4 | 53.2 | 51.1 |
| | Fold Change $(EC_{50})$[a] | 12.7 | 23.7 | 27.8 | 5.7 | 2.4 | 1.0 |

[a]REGN1979 was tested at a concentration range of 4.8 fM to 10 nM
[b]Fold change in $EC_{50}$ was calculated as the $EC_{50}$(no REGN5837)/$EC_{50}$([M] REGN5837)

Example 15: Evaluation of the Effect of REGN5837 on REGN1979-Mediated Human T-Cell Activation and Testing REGN5837 and REGN1979 in Combination at a Range of Concentrations in the Presence of WSU-DLCL2 Cells Both in vitro and in vivo studies were done to evaluate the anti-tumor efficacy of the human CD22×CD28 bsAb REGN5837, in the presence or absence of a sub-efficacious dose of a human CD20×CD3 bsAb (REGN1979), in NSG mice after implantation with human PBMC and WSU-DLCL2 cells by measuring the following parameters: a) T-cell cytotoxicity against CD22$^+$ target cells; b) upregulation of CD25 on the cell surface of CD4$^+$ and CD8$^+$ T cells, a marker of T-cell activation; c) T-cell proliferation; d) cytokine release (IL-4, IL-2, IL-6, IL-10, TNF-α, IFN-γ, and IL-17A)

Materials and Methods
Cell Lines

WSU-DLCL2: WSU-DLCL2 is a human DLBCL cell line isolated from the pleural effusion of a 41-year-old Caucasian male (Leibnitz Institute-DSMZ, Cat. #ACC 575).

Human PBMC

For cytotoxicity, T-cell activation, T-cell proliferation, and cytokine release assays leukopaks from human donors were obtained from the New York Blood Center (donor #1500A).

For in vivo mouse experiments Human PBMC were obtained from ReachBio (Cat. #0500-401).

Experimental Design

REGN5837 and REGN1979 were tested in combination at a range of concentrations to evaluate the effect of REGN5837 on REGN1979-mediated T-cell cytotoxicity against WSU-DLCL2 cells, T-cell proliferation, cell-surface expression of a marker of late T-cell activation (CD25), and cytokine release from human T cells. The percentage of target cell killing, T-cell activation, and T-cell proliferation were determined as described herein.

The anti-tumor efficacy of REGN5837 alone and in combination with REGN1979 in a model of DLBCL using WSU-DLCL2 cells and PBMC was evaluated as described herein. See Table 31.

In Vitro Assessment of the Effect of REGN5837 on the Potency of REGN1979 to Mediate T-Cell Activation Human Primary T Cell Isolation Human peripheral blood mononuclear cells (PBMC) were isolated from a healthy donor leukocyte pack via density gradient centrifugation using 50 mL SepMate™ tubes following the manufacturer's recommended protocol. Briefly, 15 mL of FicollPaque PLUS was layered into 50 mL SepMate tubes, followed by addition of 30 mL of whole blood diluted 1:2 with D-PBS. Tubes were centrifuged at room temperature at 1200×g for 10 minutes with the brake off. The top layer, containing plasma and PBMC was decanted into a fresh tube. Subsequent steps were followed according to SepMate manufacturer's protocol. Isolated PBMC were frozen in FBS containing 10% DMSO at a concentration of 250×10$^6$ cells/mL in 5 mL cryovials. PBMC were thawed in a 37° water bath and resuspended in stimulation media (X-VIVO 15 cell culture media supplemented with 10% FBS, HEPES, NaPyr, NEAA, and 0.01 mM BME) containing 50 U/mL benzonase nuclease at 10 mL per 100 million PBMC and centrifuged at 300×g for 10 minutes. CD3+ T cells were isolated from pelleted PBMC's using an EasySep™ Human CD3+ T Cell Isolation Kit from StemCell Technologies following the manufacturer's recommended instructions.

Flow Cytometry-Based T-Cell Activation Assays Using PBMC

The capacity of REGN5837 to enhance T-cell activation mediated by either allogeneic primary stimulus, or with "signal 1" provided by REGN1979, was evaluated using WSU-DLCL2 target cells and human PBMC as effector cells. PBMC were enriched for lymphocytes as described herein. Target and effector cells were incubated with test article and control antibodies as described herein. Flow cytometry was performed to assess T-cell cytotoxicity, proliferation, and upregulation of markers of T-cell activation as described herein. Additionally, the effect of REGN5837 on REGN1979-mediated cytokine release was evaluated as described herein. A non-TAA×CD28 bsAb (containing a CD28-binding arm identical to REGN5837, and a non-binding arm) was tested as a non-bridging control for REGN5837.

Lymphocyte Enrichment of PBMC

Human PBMC were plated in complete media (RPMI cell culture media supplemented with 10% FBS, penicillin-streptomycin-glutamine) at 1×10$^6$ cells/mL and incubated overnight at 37° C. to enrich for lymphocytes by depleting adherent cells such as macrophages, dendritic cells, and some monocytes.

Incubation of PBMC and Target Cells with Test Articles

Lymphocyte-enriched PBMC were harvested and labeled with 1 μM of Violet Cell Tracker fluorescent tracking dye. WSU-DLCL2 target cells were labeled with 1 μM of the fluorescent dye Vybrant CFDA-SE.

Subsequently, dye-labeled PBMC were plated in round-bottom 96-well plates with dye-labeled target cells at a ratio of 5:1 (WSU-DLCL2 at 5×10$^3$ target cells/well).

Plated PBMC and target cells were incubated for 72 hours at 37° C. with test articles or their respective controls at final concentrations ranging from 12.9 pM to 100 nM (REGN5837 or non-TAA×CD28) and 4.8 fM to 10 nM (REGN1979 or non-TAA×CD3).

Flow Cytometry Analysis

Following incubation with test articles and controls, dye-labeled cells were stained with LIVE/DEAD stain and with a cocktail of fluorophore-labeled antibodies to CD2, CD4, CD8, and CD25. Counting beads (20 μL per well) were added immediately before sample analysis on a BD Celesta flow cytometer. Flow cytometry data were used to determine target cell survival, T-cell proliferation, and upregulation of markers of T-cell activation. EC$_{50}$ values were determined from a four-parameter logistic equation over a 9-point dose-response curve using GraphPad Prism software. Maximum responses for cytotoxicity, T-cell activation (CD25 upregulation), and proliferation were determined as the maximum response plateau generated by the Prism curve fit. The relative change in EC$_{50}$ compared with control was calculated as EC50$_{No\ REGN5837}$/EC50$_{[M]\ REGN5837}$, and the relative change in maximum cytokine release was calculated as Max$_{[M]\ REGN5837}$/Max$_{No\ REGN5837}$.

Target Cell Survival

The percentage of viable target cells in each experimental condition was calculated as the number of live, CFDA-SE-labeled target cells/well normalized to the number of beads collected/well. The percentage of target cell survival was determined as the ratio of the number of viable target cells in any experimental condition over the number of viable target cells in the no antibody control condition (target cells in the presence of PBMC only).

The percentage of cytotoxicity against target cells in each experimental condition, where reported in this manner, was determined as 100 minus the percent survival (calculated as described above).

CD25 Expression on CD4+ and CD8+ T Cells

Upregulation of CD25 (a marker of late-activated T cells) was assessed by gating on live, CD2+, and either CD4+ or CD8+ cells. The percentage of activated T cells expressing CD25 out of total T cells expressing either CD4 or CD8 was reported.

Proliferation of CD4+ and CD8+ T Cells

Primary CD4+ and CD8+ T-cell proliferation was assessed using flow cytometry by calculating the percentage of divided cells out of total CD4+ and CD8+ T cells. The fluorescence intensity of Violet Cell Tracker-stained cells was used as a readout of cell division, as the fluorescence intensity of each cell decreases by a factor of 2 with each round of division.

Cytokine Release Analysis

The levels of cytokines (IL-4, IL-2, IL-6, IL-10, TNF-$\alpha$, IFN-$\gamma$, and IL-17A) in cell-culture supernatants were quantified using a BD Cytometric Bead Array Human Th1/Th2/Th17 Cytokine Kit according to manufacturer's instructions.

In Vivo Model of DLBCL Using WSU-DLCL2 Cell Xenografts

Female NSG mice were used in all experiments. All mice were SC implanted with WSU-DLCL2 B-cell lymphoma cells and dosed IP with antibodies. Tumor growth was measured using calipers several times per week throughout the duration of the study. For all experiments, mice were housed in the Regeneron animal facility under standard conditions. All experiments were performed in accordance with the guidelines for the Institutional Animal Care and Use Committee (IACUC) at Regeneron.

WSU-DLCL2 Cell Culture Conditions and Tumor Implantation

The WSU-DLCL2 cell line was obtained from the Leibnitz Institute-DSMZ and maintained in RPMI-1640 media with 10% FBS supplemented with penicillin, streptomycin, glutamine, and 1 mM HEPES.

WSU-DLCL2 cells ($3 \times 10^6$ cells) were collected and mixed with $5 \times 10^5$ PBMCs and resuspended in a 1:1 mixture of PBS and GFR Matrigel. Female NSG mice were injected SC with 100 µL of the cell mixture in the right flank.

Antibody Dosing for Tumor Measurement

Prior to dosing with test articles or controls, mice were assigned to groups, stratified according to tumor burden.

Antibodies (REGN5837, REGN1979, REGN5671 [Non-TAA×CD28 non-bridging control bsAb], or H4sH17664D [Non-TAA×CD3 non-bridging control bsAb]) were administered as monotherapy or in combination by IP injection on days 1, 8, and 15 post-implantation at the doses stated in Table 31.

TABLE 31

Experimental Design for Assessing Tumor Growth and Survival

| Groups | N per Group | Dose of REGN5837 or Non-TAA × CD28 | Dose of REGN1979 or Non-TAA × CD3 | BsAb Dosing Schedule (IP Injection) | Days Tumor Volumes Measured |
|---|---|---|---|---|---|
| REGN5837 + REGN1979 | 7 | 1 mg/kg | 0.4 mg/kg | Days 1, 8, and 15 post-implantation of WSU-DLCL2 cells | Days 7, 10, 14, 16, 28, 31, 35, 38, 43, 46, 49, 53, 57, and 63 post-implantation |
| REGN5837 + REGN1979 | 7 | | 4 mg/kg | | |
| REGN5837 + Non-TAA × CD3 | 7 | | 4 mg/kg | | |
| Non-TAA × CD28 + REGN1979 | 6 | | 0.4 mg/kg | | |
| Non-TAA × CD28 + REGN1979 | 6[a] | | 4 mg/kg | | |
| Non-TAA × CD28 + Non-TAA × CD3 | 7 | | 4 mg/kg | | |

[a]One mouse died during the experiment and were excluded.

Tumor Measurement and Designated Endpoint

Tumor growth was monitored over time using caliper measurements of the tumor X and Y diameter (perpendicular measurements of length and width). Tumor volume was calculated (X*Y*[X/2], where X is the shorter diameter). Mice were euthanized when the tumor reached the designated tumor endpoint (tumor diameter >20 mm or tumor ulceration). This endpoint was in accordance with IACUC standards.

Statistical Analysis of Tumor Growth and Survival

Results of tumor volume over time were analyzed using a 2-way analysis of variance (ANOVA) followed by Tukey's post hoc test for multiple comparisons. Results of survival over time were analyzed using a Mantel-Cox test across all groups, and further Mantel-Cox tests were run for individual group-wise comparisons. Differences were considered statistically significant when p<0.05. Statistical analyses were performed using GraphPad Prism 8 software.

Results

Effect of REGN5837 on the Capacity of REGN1979 to Mediate T-Cell Cytotoxicity Against WSU-DLCL2 Target Cells and Cytokine Release from Human PBMC REGN5837 and REGN1979 were tested in combination at a range of concentrations to evaluate the effect of REGN5837 on REGN1979-mediated cytotoxicity against WSU-DLCL2 cells, T-cell activation, T-cell proliferation, and cytokine release from T cells from human PBMC as described previously. Table 30 shows the effect of REGN5837 on REGN1979-mediated cytotoxicity against WSU-DLCL2 cells, T-cell activation, and T-cell proliferation. Numerical results from 2 human donors demonstrating the effect of REGN5837 on cytokine release are summarized in Table 32.

Effect of REGN5837 on REGN1979-Mediated Cytotoxicity and Human T-Cell Proliferation The effect of increasing concentrations of REGN5837 on the potency ($EC_{50}$) and efficacy (maximal response) of REGN1979 was assessed by evaluating REGN1979-mediated cytotoxicity against WSU-DLCL2 target cells, REGN1979-mediated T-cell activation, and REGN1979-mediated proliferation of human CD4+ and CD8+ T cells from human PBMC. REGN5837 enhanced the potency of REGN1979 to mediate cytotoxicity against WSU-DLCL2 cells, T-cell activation (measured as CD25 expression on CD4+ and CD8+ T cells), and CD4+ and CD8+ T-cell proliferation in a concentration-dependent manner. At concentrations ranging from 77.2 pM to 100 nM, REGN5837 increased the potency of REGN1979-mediated T-cell cytotoxicity against target cells; at concentrations ranging from 77.2 pM to 2.78 nM, REGN5837 increased the potency of REGN1979-mediated T-cell activation and proliferation, but higher concentrations of REGN5837 did not further increase the potency of REGN1979. These data are represented graphically in FIG. 11 and in Table 30.

REGN1979-Mediated Cytokine Release from Human PBMC in the Presence of REGN5837

The effect of increasing concentrations of REGN5837 on the potency and maximal response of REGN1979-mediated cytokine release from human PBMC was assessed. In the presence of human PBMC and WSU-DLCL2 cells, increasing concentrations of REGN5837 enhanced the maximal levels of REGN1979-mediated release of IL-2, IL-4, IL-6, IL-10, TNF-α, IFN-γ, and IL-17A in a concentration-dependent manner (FIG. 12). Furthermore, increasing concentrations of REGN5837 showed a trend of enhancing the potency of REGN1979 to mediate cytokine release. The $EC_{50}$ values, maximum cytokine levels, and relative increase above background cytokine levels (without REGN5837) mediated by REGN1979 are summarized in FIG. 12 and Table 32.

TABLE 32

|  |  | Fixed Concentration of REGN5387 | | | | | |
|---|---|---|---|---|---|---|---|
|  |  | $1.0 \times 10^{-7}$ | $1.67 \times 10^{-8}$ | $2.78 \times 10^{-9}$ | $4.63 \times 10^{-10}$ | $7.72 \times 10^{-11}$ | 0 |
| IL-4 | REGN1979 $EC_{50}$ (M)[a] | $1.66 \times 10^{-11}$ | $1.53 \times 10^{-11}$ | $1.28 \times 10^{-11}$ | $1.89 \times 10^{-11}$ | $3.77 \times 10^{-10}$ | $9.99 \times 10^{-10}$ |
|  | Max CKR (pg/mL)[b] | 2,637 | 2,793 | 2,705 | 1,560 | 935 | 775 |
|  | Fold change (CKR)[c] | 3.4 | 3.6 | 3.5 | 2.0 | 1.2 | 1.0 |
| IL-2 | REGN1979 $EC_{50}$ (M) | $2.81 \times 10^{-11}$ | $1.96 \times 10^{-11}$ | $5.18 \times 10^{-12}$ | $5.36 \times 10^{-11}$ | $3.89 \times 10^{-10}$ | $1.25 \times 10^{-10}$ |
|  | Max CKR (pg/mL) | 79.3 | 75.4 | 63.2 | 70.3 | 116 | 36.2 |
|  | Fold change (CKR) | 2.2 | 2.1 | 1.7 | 1.9 | 3.2 | 1.0 |
| IL-6 | REGN1979 $EC_{50}$ (M) | $5.13 \times 10^{-11}$ | $7.89 \times 10^{-12}$ | $2.68 \times 10^{-11}$ | $1.45 \times 10^{-12}$ | $1.61 \times 10^{-10}$ | $7.42 \times 10^{-11}$ |
|  | Max CKR (pg/mL) | 366 | 304 | 367 | 246 | 210 | 190 |
|  | Fold change (CKR) | 1.9 | 1.6 | 1.9 | 1.3 | 1.1 | 1.0 |
| IL-10 | REGN1979 $EC_{50}$ (M) | $3.54 \times 10^{-11}$ | $1.04 \times 10^{-10}$ | $2.43 \times 10^{-10}$ | $5.29 \times 10^{-11}$ | $3.34 \times 10^{-11}$ | $9.95 \times 10^{-11}$ |
|  | Max CKR (pg/mL) | 528 | 683 | 835 | 633 | 450 | 512 |
|  | Fold change (CKR) | 1.0 | 1.3 | 1.6 | 1.2 | 0.9 | 1.0 |
| TNF alpha | REGN1979 $EC_{50}$ (M) | $5.03 \times 10^{-12}$ | $8.69 \times 10^{-13}$ | $3.45 \times 10^{-12}$ | $2.08 \times 10^{-03}$ | $1.62 \times 10^{-10}$ | $2.43 \times 10^{-10}$ |
|  | Max CKR (pg/mL) | 236 | 129 | 170 | NC | 35.4 | 29.6 |
|  | Fold change (CKR) | 8.0 | 4.4 | 5.8 | NC | 1.2 | 1.0 |
| IFN-gamma | REGN1979 $EC_{50}$ (M) | $1.17 \times 10^{-10}$ | $5.34 \times 10^{-11}$ | $2.00 \times 10^{-10}$ | $6.72 \times 10^{-11}$ | $6.57 \times 10^{-11}$ | $1.82 \times 10^{-10}$ |
|  | Max CKR (pg/mL) | 525 | 537 | 693 | 348 | 167 | 2.06 |
|  | Fold change (CKR) | 2.6 | 2.6 | 3.4 | 1.7 | 0.8 | 1.0 |
| IL-17A | REGN1979 $EC_{50}$ (M) | $3.22 \times 10^{-10}$ | $1.11 \times 10^{-10}$ | $7.60 \times 10^{-11}$ | $4.63 \times 10^{-10}$ | $1.86 \times 10^{-10}$ | $2.50 \times 10^{-10}$ |
|  | Max CKR (pg/mL) | 26.6 | 25.2 | 20.6 | 33.3 | 21.9 | 20.5 |
|  | Fold change (CKR) | 1.3 | 1.2 | 1.0 | 1.6 | 1.1 | 1.0 |

[a]REGN1979 was tested at a concentration ange of 4.8 fM to 10 nM.
[b]Maximum CKR was reported as the maximum plateau determined by the PRISM curve fit.
[c]Fold changes in maximum cytokine level in serum was calculated as the Max CKR([M] REGN5837)/MAX CKR(no REGN5837)
Abbrev:
CKR, cytokine release; NC, Not Calculated because the cytokine release levels did not reach saturation at the range of REGN1979 concentrations tested, or a dose-response curve could not be fitted.

Anti-Tumor Efficacy of Administration of REGN5837 in the Presence and Absence of Sub-Efficacious Doses of REGN1979

Immunodeficient NSG mice bearing WSU-DLCL2 tumors received IP injections of antibodies or non-bridging controls as described previously herein.

Figure 13A:
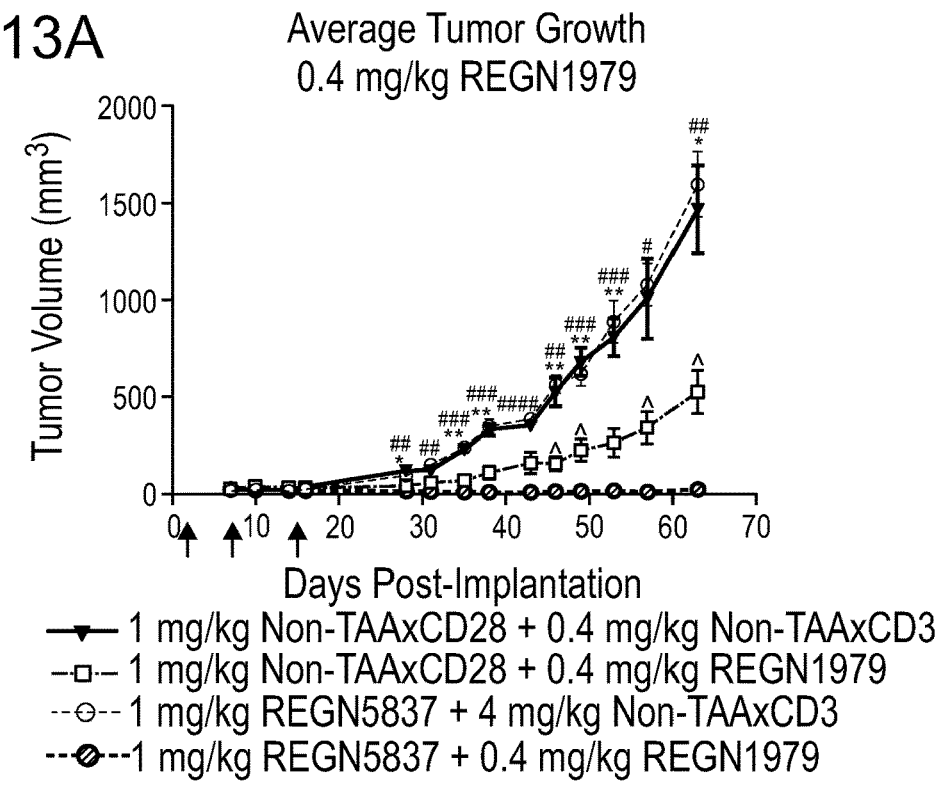
FIGS. 13A and 13B are graphs showing that treatment of NSG mice bearing WSU-DLCL2 tumors with REGN5837 in the presence of 0.4 or 4 mg/kg of REGN1979 is associated with significant tumor suppression. Briefly, Female NSG mice (n=6 to 7 per group) were implanted with a 1:1 mixture of WSU-DLCL2 B-cell lymphoma cells and human PBMC (day 0). Mice were administered combinations of 1 mg/kg REGN5837 and 0.4 mg/kg (13A) or 4 mg/kg (13B) REGN1979 (or non-bridging controls) on days 1, 8, and 15 post-implantation (arrows). Tumor growth was monitored by caliper measurement on days 7, 10, 14, 16, 28, 31, 35, 38, 43, 46, 49, 53, 57, and 63 post-implantation. Combined data are expressed as the group mean±SEM. Statistical significance was determined using two-way ANOVA with Tukey's post hoc test. The following symbols were used to indicate statistically significant differences between groups: $p<0.05$; , $p<0.01$; *, $p<0.001$; ****, $p<0.0001$. Asterisks indicate statistical significance between REGN1979 monotherapy and isotype control, hash marks indicate significance between the combination of REGN5837 with REGN1979 and isotype control, and carets indicate significance between REGN1979 monotherapy and the combination of REGN5837 with REGN1979.
Figure 13B:
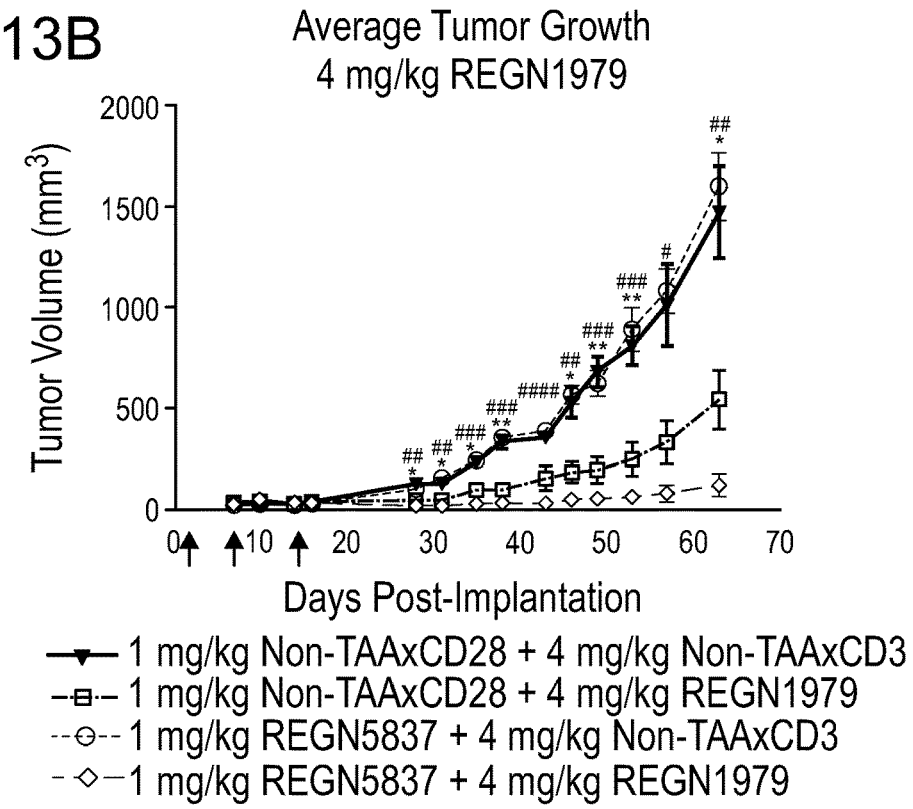

In tumor-bearing mice, treatment with 1 mg/kg REGN5837 in the presence of either 0.4 or 4 mg/kg REGN1979 resulted in statistically significant suppression of tumor growth compared with non-bridging control bsAbs (non-TAA×CD28 and non-TAA×CD3 bsAbs) by day 28 (6 days following the final antibody dose (FIGS. 13A and 13B). The combination of 1 mg/kg REGN5837 and 0.4 mg/kg REGN1979 resulted in a significant reduction in tumor volume relative to REGN1979 monotherapy by day 46.

Both 0.4 and 4 mg/kg REGN1979 monotherapy resulted in modest tumor suppression relative to non-bridging controls by day 28, whereas REGN5837 monotherapy had no effect. Rapid tumor growth was observed upon dosing with non-bridging control bsAbs throughout the dosing period, and all mice were euthanized on day 125.

Figure 14:
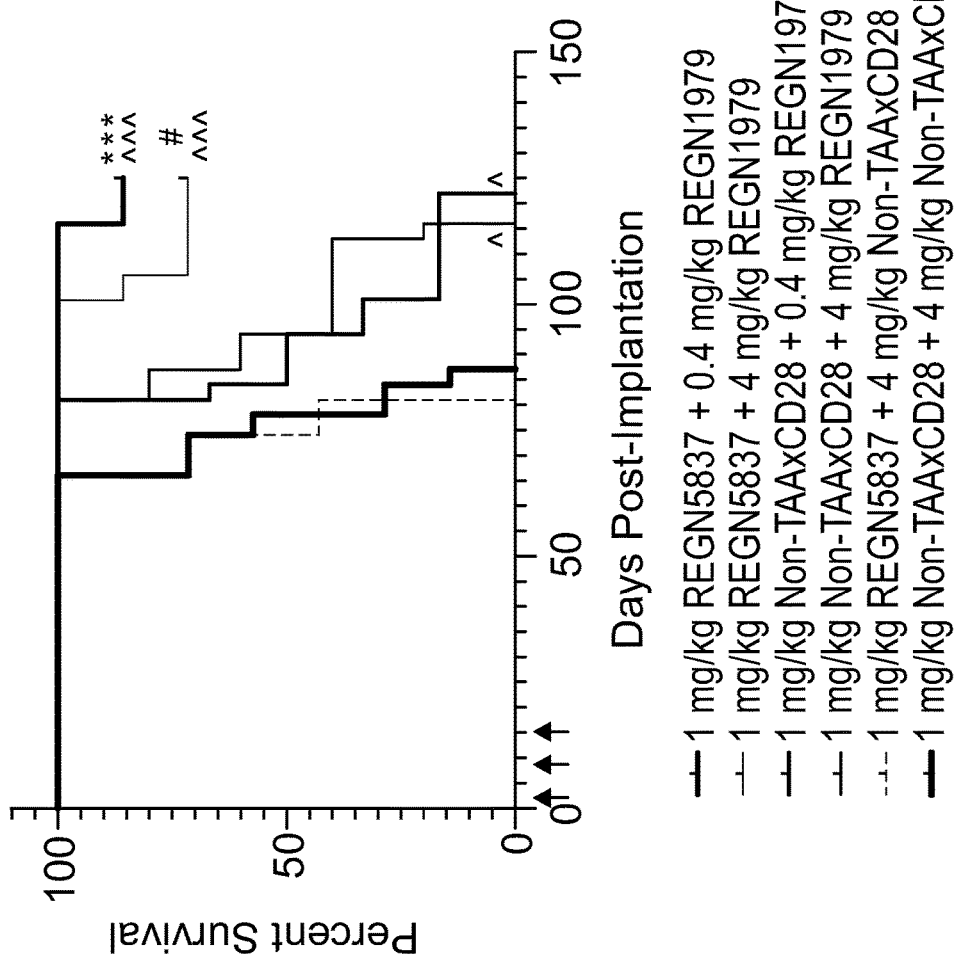
FIG. 14 is a graph showing that treatment of NSG mice bearing WSU-DLCL2 tumors with REGN5837 in the presence of sub-efficacious doses of REGN1979 is associated with significantly greater survival than REGN5837 or REGN1979 monotherapy. Briefly, female NSG mice (n=6 to 7 per group) were implanted with a 1:1 mixture of WSU-DLCL2 B-cell lymphoma cells and human PBMC (day 0). Mice were administered combinations of REGN5837 and REGN1979 or controls on days 1, 8, and 15 post-implantation (arrows). Statistical significance was determined using a Mantel-Cox test. The following symbols were used to indicate statistically significant differences between groups: *, $p<0.05$; ***, $p<0.001$. Carets indicate statistical significance compared with isotype control, asterisks indicate significance compared with 0.4 mg/kg REGN1979 monotherapy, and hash marks indicate significance compared with 4 mg/kg REGN1979 monotherapy.

A Mantel-Cox test detected statistically significant differences in survival across all groups (p=0.0001), and additional Mantel-Cox tests were performed for group-wise comparisons. A significant increase in survival was observed for mice dosed with 1 mg/kg REGN5837 in combination with either 0.4 or 4 mg/kg REGN1979 (85% and 70% survival, respectively) compared with mice dosed with non-bridging control antibodies (no survival) (FIG. 14).

Furthermore, a significant increase in survival was observed for mice dosed with 1 mg/kg REGN5837 in combination with either 0.4 or 4 mg/kg REGN1979 compared with mice dosed with either REGN5837 or REGN1979 monotherapy.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated bispecific antigen binding molecule comprising:
   a) a first antigen-binding domain (D1) that binds human CD28 and comprises a heavy chain variable region (HCVR) comprising three heavy chain complementarity determining regions (HCDR1, HCDR2 and HCDR3) comprising amino acid sequences of SEQ ID NOs: 28, 30, 32, and a light chain variable region (LCVR) comprising three light chain complementarity determining regions (LCDR1, LCDR2 and LCDR3) comprising amino acid sequences of SEQ ID NOs: 12, 14, 16; and
   b) a second antigen-binding domain (D2) that specifically binds human CD22 on a target tumor cell and comprises HCVR CDRs comprising amino acid sequences of SEQ ID NOs: 4, 6, 8, and LCVR CDRs comprising amino acid sequences of SEQ ID NOs: 12, 14, 16.

2. The isolated bispecific antigen binding molecule of claim 1, wherein the second antigen-binding domain (D2) binds an epitope on human CD22 comprising one or more amino acids of SEQ ID NO:57, SEQ ID NO:58, and/or SEQ ID NO:59.

3. The isolated bispecific antigen binding molecule of claim 1, wherein the bispecific antigen binding molecule has a property selected from the group consisting of:
   (a) binds human CD22 with a $K_D$ of less than about 15 nM as measured by surface plasmon resonance at 25° C.;
   (b) binds Macaca fascicularis CD22 with a $K_D$ of less than about 60 μM as measured by surface plasmon resonance at 25° C.;
   (c) binds human CD28 with a $K_D$ of less than about 45 μM as measured by surface plasmon resonance at 25° C.;
   (d) binds to the surface of cells expressing human CD28 with an $EC_{50}$ of less than about $1 \times 10^{-8}$ M as measured by an in vitro FACS binding assay;
   (e) binds to the surface of cells expressing human CD22 with an $EC_{50}$ of less than about $1 \times 10^{-8}$ M as measured by an in vitro FACS binding assay; and
   (f) demonstrates a costimulatory effect when used in conjunction with an anti-CD20×CD3 bispecific antibody.

4. The isolated bispecific antigen-binding molecule of claim 1, wherein the first antigen-binding domain comprises a HCVR/LCVR pair comprising the amino acid sequences of SEQ ID NOs: 26/10.

5. The isolated bispecific antigen-binding molecule of claim 1, wherein the second antigen-binding domain comprises a HCVR/LCVR pair comprising the amino acid sequences of SEQ ID NO: 2/10.

6. The isolated bispecific antigen-binding molecule of claim 1, comprising:
   a) a first antigen binding domain that comprises a HCVR/LCVR pair comprising amino acid sequences of SEQ ID NOs:26/10; and
   b) a second antigen binding domain that comprises a HCVR/LCVR pair comprising amino acid sequences of SEQ ID NOs: 2/10.

7. A pharmaceutical composition comprising the bispecific antigen-binding molecule of claim 1, and a pharmaceutically acceptable carrier or diluent.

8. A nucleic acid molecule comprising a nucleotide sequence encoding the bispecific antigen binding molecule of claim 1.

9. An expression vector comprising the nucleic acid of claim 8.

10. A host cell comprising the expression vector of claim 9.

* * * * *